US010945955B2

(12) United States Patent
Haraszti et al.

(10) Patent No.: US 10,945,955 B2
(45) Date of Patent: Mar. 16, 2021

(54) ARTIFICIAL EXOSOME COMPOSITION AND RELATED METHODS

(71) Applicant: UNIVERSITY OF MASSACHUSETTS, Boston, MA (US)

(72) Inventors: Reka Agnes Haraszti, Shrewsbury, MA (US); Anastasia Khvorova, Westborough, MA (US); Neil Aronin, Newtonville, MA (US)

(73) Assignee: UNIVERSITY OF MASSACHUSETTS, Boston, MA (US)

(*) Notice: Subject to any disclaimer, the term of this patent is extended or adjusted under 35 U.S.C. 154(b) by 0 days.

(21) Appl. No.: 16/393,582

(22) Filed: Apr. 24, 2019

(65) Prior Publication Data

US 2019/0343767 A1 Nov. 14, 2019

Related U.S. Application Data

(60) Provisional application No. 62/662,570, filed on Apr. 25, 2018.

(51) Int. Cl.
| | |
|---|---|
| *A61K 9/127* | (2006.01) |
| *A61K 31/7115* | (2006.01) |
| *A61K 31/7125* | (2006.01) |
| *A61K 35/17* | (2015.01) |
| *A61K 38/17* | (2006.01) |
| *A61K 47/28* | (2006.01) |
| *A61K 47/62* | (2017.01) |
| *A61K 47/69* | (2017.01) |
| *C12N 15/113* | (2010.01) |
| *C12N 15/86* | (2006.01) |

(52) U.S. Cl.
CPC ........ *A61K 9/1272* (2013.01); *A61K 31/7115* (2013.01); *A61K 31/7125* (2013.01); *A61K 35/17* (2013.01); *A61K 38/1719* (2013.01); *A61K 38/1741* (2013.01); *A61K 47/28* (2013.01); *A61K 47/62* (2017.08); *A61K 47/6917* (2017.08); *C12N 15/113* (2013.01); *C12N 15/86* (2013.01); *C12N 2310/20* (2017.05); *C12N 2310/313* (2013.01); *C12N 2310/3183* (2013.01); *C12N 2310/321* (2013.01); *C12N 2310/3231* (2013.01)

(58) Field of Classification Search
None
See application file for complete search history.

(56) References Cited

U.S. PATENT DOCUMENTS

| | | |
|---|---|---|
| 4,186,183 A | 1/1980 | Steck et al. |
| 4,217,344 A | 8/1980 | Vanlerberghe et al. |
| 4,261,975 A | 4/1981 | Wardle et al. |
| 4,485,054 A | 11/1984 | Mezei et al. |
| 4,774,085 A | 9/1988 | Fidler |
| 4,946,787 A | 8/1990 | Eppstein et al. |
| 2019/0343767 A1 | 11/2019 | Haraszti |

FOREIGN PATENT DOCUMENTS

| | | |
|---|---|---|
| WO | WO 91/17424 A1 | 11/1991 |
| WO | WO 2010/056337 A2 | 5/2010 |
| WO | WO 2019/209956 A1 | 10/2019 |

OTHER PUBLICATIONS

Haraszti, et al. (Jun. 28, 2019) "Serum Deprivation of Mesenchymal Stem Cells Improves Exosome Activity and Alters Lipid and Protein Composition", iScience, 16: 230-41 and Supplementary Material, 27 pages. (Year: 2019).*
Zhang, et al. (2016) "Exosomes from Human Umbilical Cord Mesenchymal Stem Cells: Identification, Purification, and Biological Characteristics", Stem Cells International, vol. 2016, Article ID 1929536, 11 pages long. (Year: 2016).*
Konstantin (2015) "Exosomes: Isolation and Characterization Methods and Specific Markers", Mater Methods, 5: 1450 (https://www.labome.com/method/Exosomes-Isolation-and-Characterization-Methods-and-Specific-Markers.html#ref52), 18 pages as printed. (Year: 2015).*
PCT/US2019/028919 / WO 2019/209956 A1, Apr. 24, 2019 / Oct. 31, 2019, Reka Agnes Haraszti.
Haney, et al. (Jun. 10, 2015) "Exosomes as drug delivery vehicles for Parkinson's disease therapy", Journal of Controlled release, vol. 207, pp. 18-30.
Haraszti, et al. (May 15, 2018) "Engineered Exosomes for Delivery of Therapeutic siRNAS to Neurons", University of Massachusetts Graduate School of Biomedical Sciences, 214 Pages.
Martinez-Lostao, et al. (Aug. 2010) "Liposome-Bound APO2L/Trail Is an Effective Treatment in a Rabbit Model of Rheumatoid Arthritis", Arthritis and Rheumatism, vol. 62, No. 8, pp. 2272-2282.
Ordonez-Gutierrez, et al. (Feb. 2015) "Repeated intraperitoneal injections of liposomes containing phosphatidic acid and cardiolipin reduce amyloid-β levels in APP/PS1 transgenic mice", Nanomedicine, vol. 11, No. 2, pp. 421-430.
Simondazeh, et al. (Apr. 2009) "An Isocratic HPLC Method for the Simultaneous Determination of Cholesterol, Cardiolipin, and DOPC in Lyophilized Lipids and Liposomal Formulations", Journal of Chromatographic Science, vol. 47, No. 4, pp. 304-308.
Suga, et al. (Nov. 12, 2015) "Liposomes modified with cardiolipin can act as a platform to regulate the potential flux of NADP plus-dependent isocitrate dehydrogenase", Metabolic Engineering Communications, vol. 3, pp. 8-14.
Aicart-Ramos et al., "Protein palmitoylation and subcellular trafficking", Biochimica et Biophysica Acta 1808 (2011) pp. 2981-2994.
Akbarzadeh et al., "Liposome: classification, preparatkion, and application", Nanoscale Research Letters (2013) 8:102.

(Continued)

*Primary Examiner* — Robert M Kelly
(74) *Attorney, Agent, or Firm* — Lathrop GPM LLP; James H. Velema, Esq.

(57) ABSTRACT

Novel artificial exosomes and methods for producing novel artificial exosomes are provided. Methods of delivering cargo molecules to a cell using artificial exosomes are also provided.

20 Claims, 18 Drawing Sheets
(16 of 18 Drawing Sheet(s) Filed in Color)

(56) References Cited

OTHER PUBLICATIONS

Alterman et al., "Hydrophobically Modified siRNAs Silence Huntingtin mRNA in Primary Neurons and Mouse Brain", Molecular Therapy Nucleic Acids (2015) 4, e266.

Baumann et al., Biochemistry of Lipids, Lipoproteins, and Membranes, Chapter 2 (2002).

Cao et al., "A novel Cardiolipin-remodeling Pathway Revealed by a Gene Encoding an Endoplasmic Reticulum-associated Acyl-Col: Lysocardiolipin Acyltransferase (ALCAT1) in Mouse", Journal of Biological Chemistry 279, May 19, 2004, pp. 31727-31734.

Deamer et al., "Large Volume Liposomes by an Ether Vaporization Method", Biochimica et Biophysica Acta 448 (1976) pp. 629-634.

Delva et al., "The Desmosome", Cold Spring Harbor Perspectives in Biology, Aug. 2009 1(2): a002543.

Didiot et al., "Exosome-mediated Delivery of Hydrophobically Modified siRNA for Huntingtin mRNA Silencing", Molecular Therapy, 24(10), pp. 1836-1847.

Fraley et al., "Entrapment of a bacterial plasmid in phospholipid vesicles: Potential for gene transfer", Proc. Natl. Acad. Sci. USA, vol. 79, No. 7, pp. 3348-3352, Jul. 1979.

Garcia-Manrique et al., "Therapeutic biomaterials based on extracellular vesicles: classification of bio-engineering and mimetic preparation routes", Journal of Extracellular Vesicles, Jan. 17, 2018, vol. 7, No. 1.

Haraszti et al., "High-resolution proteomic and lipidomic analysis of exosomes and microvesicles from different cell sources", Journal of Extracellular Vesicles, Nov. 17, 2016, vol. 5, No. 1.

Haraszti et al., "5'-Vinylphosphonate improves tissue accumulation and efficacy of conjugated siRNAs in vivo", Nucleic Acids Research, 2017, vol. 45, No. 13, Jun. 7, 2017, pp. 7581-7592.

Hope et al., "Production of large unilamellar vesicles by a rapid extrusion procedure", Biochimica et Biophysica Acta 812 (1985) pp. 55-65.

Huijbregts et al., Lipid Metabolism and Regulation of Membrane Trafficking, Traffic 2000 1: 195-202 (2002).

Ikonen, "Roles of lipid rafts in membrane transport", Current Opinion in Cell Biology (2001), 13: 470-477.

Kiebish et al., "Dynamic simulation of cardiolipin remodeling" greasing the wheels for an interpretative approach to lipidomics, Journal of Lipid Research, (2010) 51: 2153-2170.

Kowal et al., "Proteomic comparison defines novel markers to characterize heterogeneous populations of extracellular vesicle subtypes", Proceedings of the National Academy of Sciences of Untied States of America, Epub Feb. 8, 2016, vol. 113, No. 8 pp. E968-E977.

Kümmel et al., Principles of membrane tethering and fusion in endosome and lysosome biogenesis, Current Opinion in Cell Biology (2014) 29: 61-66.

Lai et al., "Visualization and tracking of tumour extracellular vesicle delivery and RNA translation using multiplexed reporters", Nature Communications, 6: 7029 (2015).

Marcus et al., "FedExosomes: Engineering Therapeutic Biological nanoparticles that Truly Deliver", Pharmaceuticals 2013, 6, pp. 659-680.

Mayer et al., "Vesicles of variable sizes produced by a rapid extrusion procedure", Biochimica et Biophysica Acta 858 (1986) pp. 161-168.

Nabhan et al., "Formation and release of arrestin domain-containing protein 1-mediated microvesicles (ARMMs) at plasma membrane by recruitment of TSG101 protein", PNAS, Mar. 13, 2012, vol. 109, No. 11, pp. 4146-4151.

Nikan et al., "Docosahexaenoic Acid Conjugation Enhances Distribution and Safety of siRNA upon Local Administration in Mouse Brain", Molecular Therapy Nucleic Acids (2016)5, e344.

Paulmann et al., "Structure-Activity Analysis of the Dermcidin-derived Peptide DCD-1 L, an Anionic Antimicrobial Peptide Present in Human Sweat", Journal of Biological Chemistry, 287: 8434-8443 (2012).

Quah et al., "The immunogenicity of dendritic cell-derived exosomes", Blood Cells, Molecules, and Diseases 35 (2005) pp. 94-110.

Schlame et al., "The physical state of lipid substrates provides transacylation specificity for tafassin", Nature Chemical Biology, vol. 8, (2012) pp. 862-869.

Shen et al., "Protein Targeting to Exosomes/Microvesicles by Plasma Membrane Anchors", Journal of Biological Chemistry (2011), 286, pp. 14383-14395.

Watson et al., "Fetuin-A triggers the secretion of a novel set of exosomes in detached tumor cells that mediate their adhesion and spreading", FEBS Letters, 586 (2012) pp. 3458-3463.

Williams et al., "Low density lipoprotein receptor-independent hepatic uptake of a synthetic, cholesterol-scavenging lipoprotein: Implications for the treatment of receptor-deficient atherosclerosis", Proc. Natl. Acad. Sci. USA, vol. 85, pp. 242-246, Jan. 1988.

Zhu et al., "Comprehensive toxicity and immunogenicity studies reveal minimal effects in mice following sustained dosing of extracellular vesicles derived from HEK293T cells", Journal of Extracellular Vesicles, 6:1, 1324730 (2017).

International Search Report and Written Opinion in related PCT Application No. PCT/US19/28919, dated Sep. 3, 2019 (20 pages).

* cited by examiner

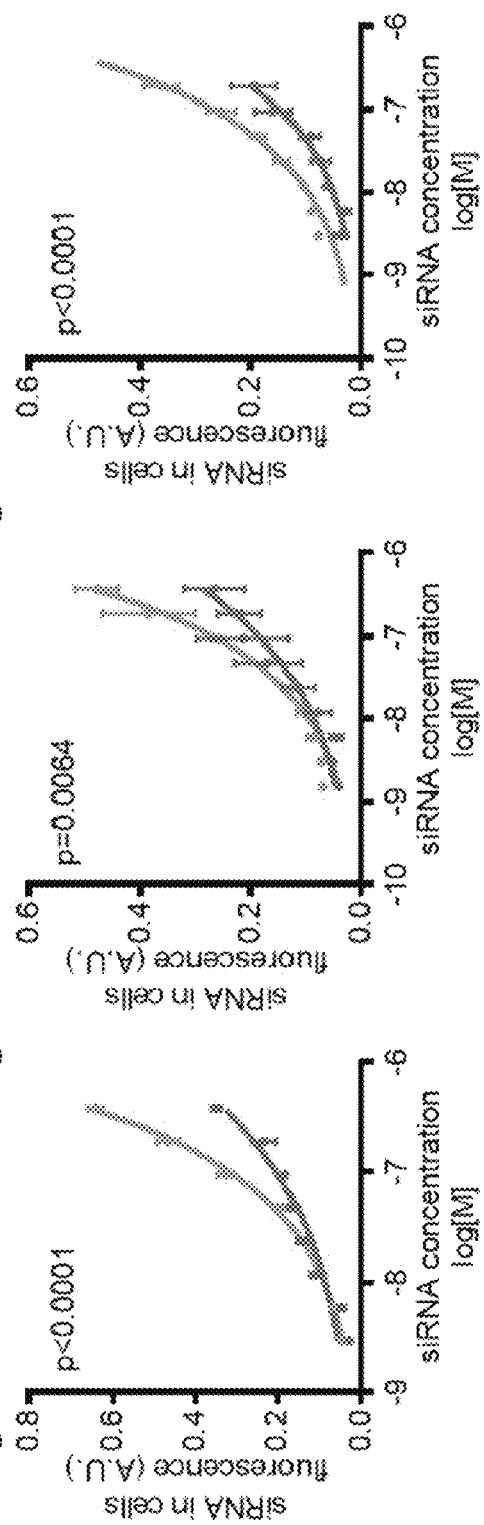
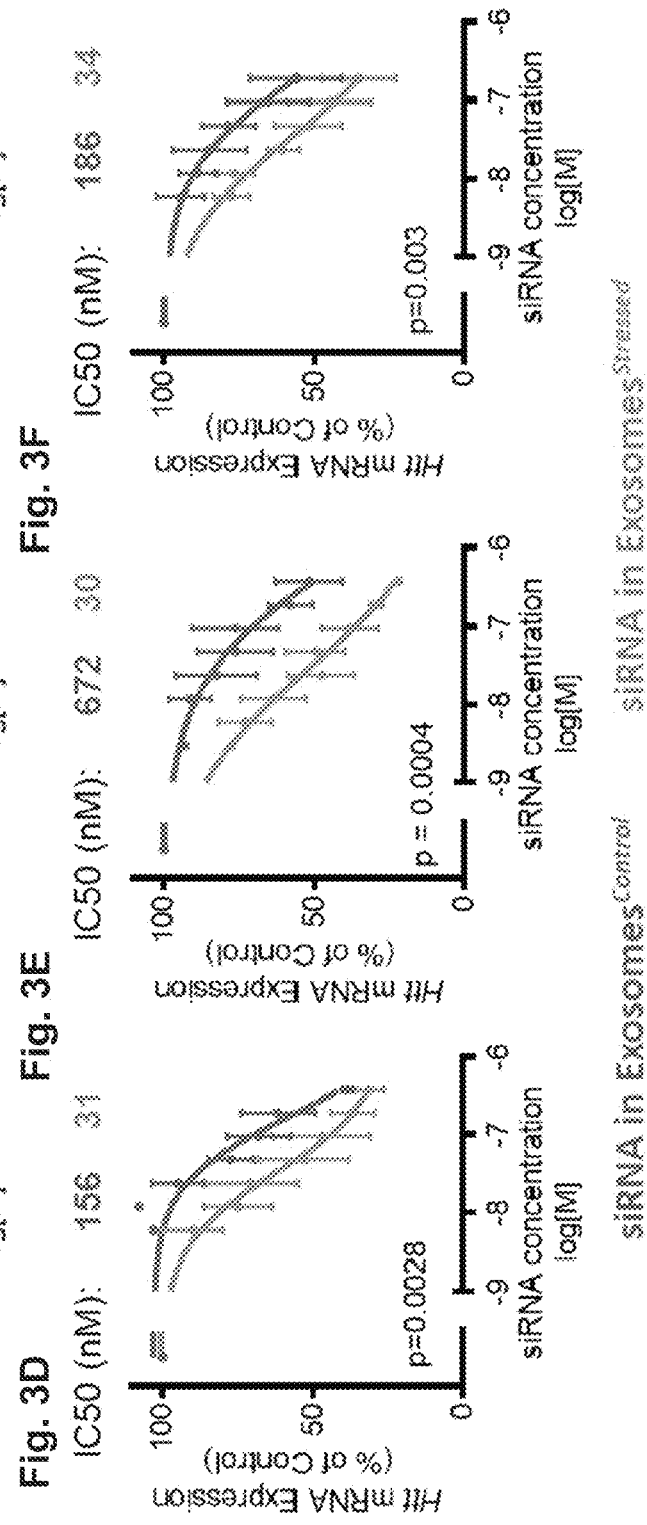
Fig. 3A, Fig. 3B, Fig. 3C, Fig. 3D, Fig. 3E, Fig. 3F

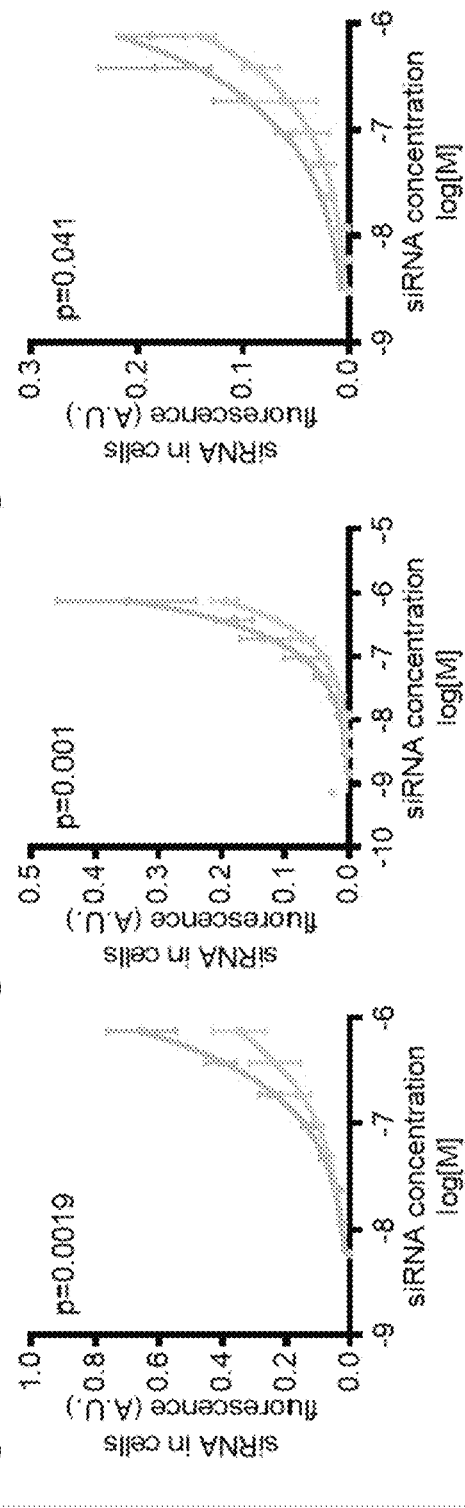
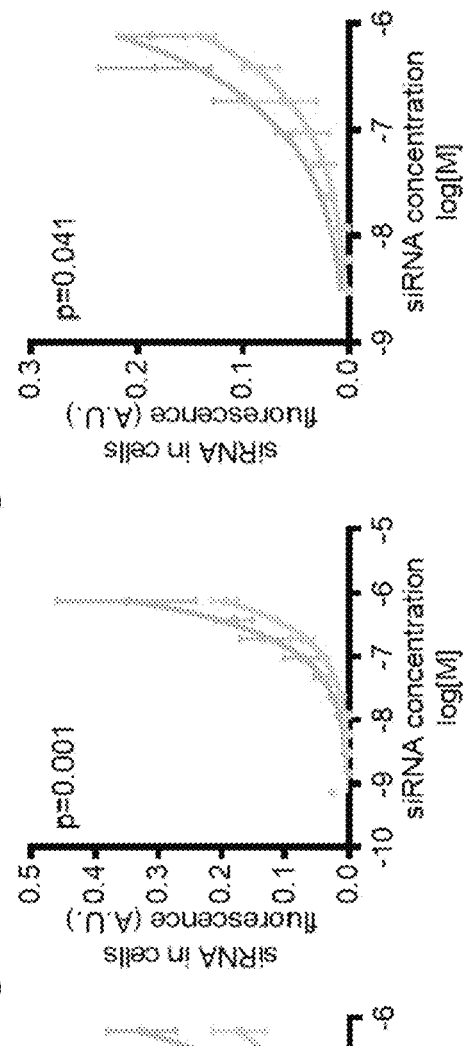
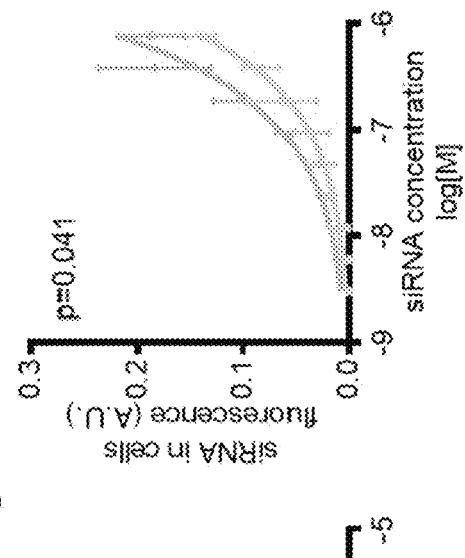
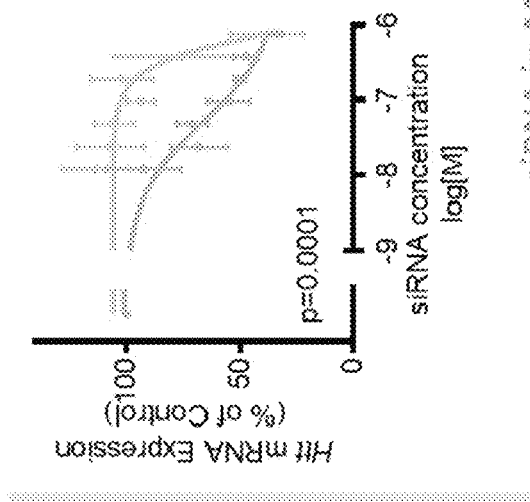
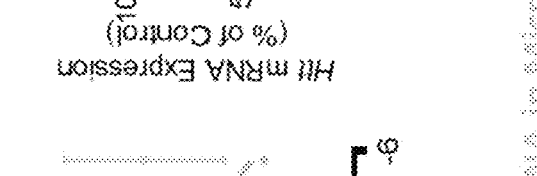
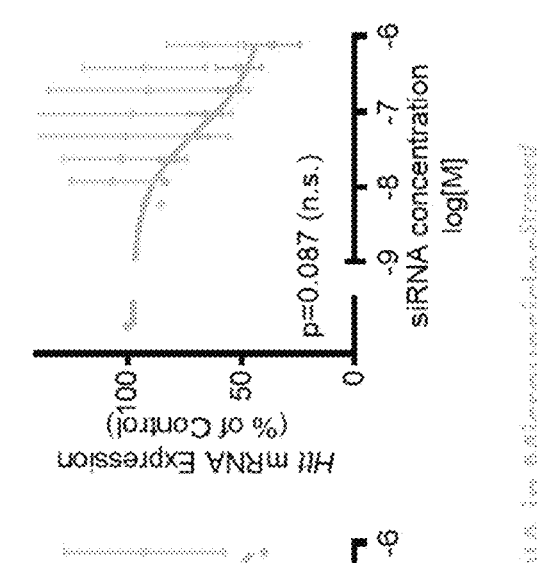

ARTIFICIAL EXOSOME COMPOSITION AND RELATED METHODS

RELATED APPLICATIONS

This application claims the benefit of priority of U.S. Provisional Application No. 62/662,570, filed on Apr. 25, 2018, the contents of which are hereby incorporated by reference in their entirety for all purposes.

STATEMENT OF FEDERALLY SPONSORED RESEARCH

This invention was made with government support under Grant No. TR000888 awarded by the National Institutes of Health. The Government has certain rights in this invention.

FIELD OF THE INVENTION

This disclosure relates to artificial exosome compositions and related methods for producing and using these compositions. Methods of delivering cargo molecules in artificial exosomes are also described.

BACKGROUND

Exosomes are small (e.g., 30-100 nm) naturally-occurring, cell-derived extracellular vesicles that are present in many, and perhaps all, biological fluids. Exosomes have received considerable attention as a mechanism to transfer exogenous molecular cargo to recipient cells (e.g., tumor cells), thereby inducing phenotypic change in the recipient cells (see, e.g., Zomer et al. *In Vivo imaging reveals extracellular vesicle-mediated phenocopying of metastatic behavior*, Cell 161: 1046-1057 (2015)). However, critical questions impede the use of exosomes for clinical applications. In particular, production of exosomes from cells is a tedious, low yield process that is often not well-controlled. Moreover, the essential components of active exosomes are not well established. Finally, fundamental mechanisms of exosomal delivery are currently unclear. Accordingly, there exists a need in the art for technologies that address these issues.

SUMMARY

The instant disclosure addresses the art-recognized deficiencies of conventional exosomes by providing novel, non-naturally occurring "artificial" exosomes that are optimized for therapeutic and non-therapeutic use. Also provided are methods for using these artificial exosomes to deliver cargo to target cells or tissues. Furthermore, the present invention describes methods for screening for components of artificial exosomes as well as methods for assaying the quality of artificial exosomes.

In one aspect of the invention, an artificial exosome comprising rab7, desmoplakin, alpha 2-HS glycoprotein (AHSG), and a cardiolipin or a variant thereof, is provided.

In an embodiment, the artificial exosome is derived from a liposome base composition.

In an embodiment, the artificial exosome further comprises dioleoylphosphatidylcholine (DOPC) and cholesterol.

In an embodiment, rab7, desmoplakin, and AHSG each comprise a lipid anchor. In an embodiment, the lipid anchor is one or more of a myristoylation, a palmitoylation, a prenylation, and a glypiation. In an embodiment, the lipid anchor is a transmembrane domain, a PIP2-binding domain, or a PIP3-binding domain. In an embodiment, the cardiolipin or variant thereof is selected from the group consisting of cardiolipin, monolysocardiolipin, and dilysocardiolipin. In an embodiment, the cardiolipin or the variant thereof is dilysocardiolipin.

In an embodiment, the cardiolipin or the variant thereof comprises about 10% to about 50% of the total lipid content of the artificial exosome. In an embodiment, the cardiolipin or variant thereof comprises about 30% of the total lipid content of the artificial exosome. In an embodiment, the artificial exosome comprises a DOPC:cholesterol:cardiolipin ratio of about 40:30:30% w/w.

In an embodiment, the artificial exosome is loaded with a cargo molecule. In an embodiment, the cargo molecule is selected from the group consisting of a peptide, a polypeptide, a nucleic acid, a virus, a small molecule, a fluorophore, and a combination thereof.

In an embodiment, the nucleic acid is an oligonucleotide. In an embodiment, the oligonucleotide comprises one or more hydrophobic modifications. In an embodiment, the oligonucleotide comprises one or more modified nucleotides selected from the group consisting of a modified ribose group, a modified phosphate group, and a modified nucleobase.

In an embodiment, the modified ribose group is selected from the group consisting of 2'-O-methyl, 2'-fluoro, 2'-deoxy, 2'-O-(2-methoxyethyl) (MOE), 2'-NH2, or a bicyclic nucleotide such as locked nucleic acid (LNA), 2'-(S)-constrained ethyl (S-cEt), constrained MOE, and 2'-O,4'-C-aminomethylene bridged nucleic acid (2',4'-BNANC).

In an embodiment, the modified phosphate group comprises a modification selected from the group consisting of phosphorothioate, phosphonoacetate (PACE), thiophosphonoacetate (thioPACE), amide, triazole, phosphonate, and phosphotriester.

In an embodiment, the modified nucleobase is selected from the group consisting of 2-thiouridine, 4-thiouridine, N6-methyladenosine, pseudouridine, 2,6-diaminopurine, inosine, thymidine, 5-methylcytosine, 5-substituted pyrimidine, isoguanine, isocytosine, and halogenated aromatic. In an embodiment, the virus is an adenovirus or adeno associated virus (AAV). In an embodiment, the small molecule is a chemotherapeutic agent.

In an embodiment, the cargo comprises one or both of an RNA-guided nuclease and a guide RNA. In an embodiment, the RNA-guided nuclease is a CRISPR nuclease.

In an embodiment, the artificial exosome is capable of targeting neuronal cells.

In another aspect of the invention, an artificial exosome comprising rab7, desmoplakin, alpha 2-HS glycoprotein (AHSG), and a cardiolipin or a variant thereof, wherein the artificial exosome is free of any one or more of CD9, CD37, CD63, CD81, CD82, Tsg101, and Alix, is provided.

In another aspect of the invention, an artificial exosome comprising rab7, desmoplakin, alpha 2-HS glycoprotein (AHSG), and a cardiolipin or a variant thereof, wherein the artificial exosome comprises one or both of 100 or fewer different polypeptides and 100 or fewer different lipids, is provided.

In another aspect of the invention, an artificial exosome comprising rab7, desmoplakin, alpha 2-HS glycoprotein (AHSG), and a cardiolipin or a variant thereof, wherein the artificial exosome is free of any immunogenic components, is provided.

In another aspect of the invention, an artificial exosome comprising rab7, desmoplakin, alpha 2-HS glycoprotein (AHSG), and a cardiolipin or a variant thereof, wherein the artificial exosome is enriched in any one or more of rab7, desmoplakin, alpha 2-HS glycoprotein (AHSG), and a cardiolipin or variant thereof relative to a non-artificial exosome, is provided.

In another aspect of the invention, an artificial exosome comprising rab7, desmoplakin, alpha 2-HS glycoprotein (AHSG), a cardiolipin or variant thereof, and exogenously-derived cargo, is provided.

In one aspect of the invention, a method of enriching exosomes, comprising incubating a population of exosomes with a binding agent that binds to one or more of rab7, desmoplakin, alpha 2-HS glycoprotein (AHSG), and a cardiolipin or a variant thereof, is provided.

In an embodiment, the binding agent is an antibody or an antigen-binding fragment thereof. In an embodiment, the binding agent is immobilized on a solid surface.

In an embodiment, the population of exosomes is contained in a buffer, a cell culture medium or a bodily fluid.

In one aspect of the invention, a method of producing an artificial exosome, comprising the steps of: a) mixing DOPC, cholesterol, and a cardiolipin or a variant thereof to form a cardiolipin-containing liposome; and b) incubating the cardiolipin-containing liposome with rab7, desmoplakin, and AHSG to form an artificial exosome, is provided.

In an embodiment, the method further comprises step c) wherein the artificial exosome is isolated. In an embodiment, the mixing step a) occurs in an organic solvent. In an embodiment, the method further comprises drying the mixture to form a dry lipid film. In an embodiment, the method further comprises rehydrating the dry lipid film in an aqueous buffer to form the cardiolipin-containing liposome.

In an embodiment, the rab7, the desmoplakin, and the AHSG each comprises a lipid anchor. In an embodiment, the lipid anchor is one or more of a myristoylation, a palmitoylation, a prenylation, and a glypiation. In an embodiment, the lipid anchor is a transmembrane domain, a PIP2-binding domain, or a PIP3-binding domain.

In an embodiment, the incubating step b) occurs for about 1 hour and at about 37° C. In an embodiment, the isolating step c) comprises centrifuging the artificial exosome. In an embodiment, the centrifuging is performed at about 100,000 g for about 30 minutes to about 2 hours. In an embodiment, the method further comprises step d) wherein the isolated artificial exosome is incubated with a cargo molecule to produce a loaded artificial exosome. In an embodiment, the mixing step a) further comprises mixing a cargo molecule to produce a loaded cardiolipin-containing liposome.

In an embodiment, the cargo molecule is selected from the group consisting of a peptide, a polypeptide, a nucleic acid, a virus, a small molecule, and a fluorophore, or a combination thereof. In an embodiment, the nucleic acid is an oligonucleotide. In an embodiment, the oligonucleotide is conjugated to a hydrophobic moiety.

In an embodiment, the oligonucleotide is incubated with the artificial exosome for about 30 minutes to about 2 hours.

In an embodiment, the method further comprises step e) wherein the loaded artificial exosome is isolated. In an embodiment, the loaded artificial exosome is isolated by centrifuging at about 100,000 g for about 30 minutes to about 2 hours.

In one aspect of the invention, a method of delivering a cargo molecule to a neuronal cell, comprising contacting the neuronal cell with an artificial exosome containing the cargo molecule, wherein the artificial exosome comprises rab7, desmoplakin, AHSG, and a cardiolipin or variant thereof, is provided.

In an embodiment, the artificial exosome is derived from a liposome base composition. In an embodiment, the artificial exosome further comprises dioleoylphosphatidylcholine (DOPC) and cholesterol.

In an embodiment, rab7, desmoplakin, and AHSG each comprise a lipid anchor. In an embodiment, the lipid anchor is one or more of a myristoylation, a palmitoylation, a prenylation, and a glypiation. In an embodiment, the lipid anchor is a transmembrane domain, a PIP2-binding domain, or a PIP3-binding domain. In an embodiment, the cardiolipin or the variant thereof is selected from the group consisting of cardiolipin, monolysocardiolipin, and dilysocardiolipin. In an embodiment, the cardiolipin or the variant thereof is dilysocardiolipin.

In an embodiment, the cardiolipin or the variant thereof is about 10% to about 50% of the total lipid content of the artificial exosome. In an embodiment, the cardiolipin or variant thereof is about 30% of the total lipid content of the artificial exosome. In an embodiment, the method comprises a DOPC:cholesterol:cardiolipin ratio of about 40:30:30% w/w.

In an embodiment, the artificial exosome is loaded with a cargo molecule. In an embodiment, the cargo molecule is selected from the group consisting of a peptide, a polypeptide, a nucleic acid, a virus, a small molecule, and a fluorophore, or a combination thereof. In an embodiment, the nucleic acid is an oligonucleotide. In an embodiment, the oligonucleotide comprises one or more hydrophobic modifications.

In an embodiment, the oligonucleotide comprises one or more modified nucleotides selected from the group consisting of a modified ribose group, a modified phosphate group, and a modified nucleobase. In an embodiment, the modified ribose group is selected from the group consisting of 2'-O-methyl, 2'-fluoro, 2'-deoxy, 2'-O-(2-methoxyethyl) (MOE), 2'-NH2, or a bicyclic nucleotide such as locked nucleic acid (LNA), 2'-(S)-constrained ethyl (S-cEt), constrained MOE, and 2'-0,4'-C-aminomethylene bridged nucleic acid (2',4'-BNANC).

In an embodiment, the modified phosphate group is selected from the group consisting of phosphorothioate, phosphonoacetate (PACE), thiophosphonoacetate (thio-PACE), amide, triazole, phosphonate, and phosphotriester. In an embodiment, the modified nucleobase is selected from the group consisting of 2-thiouridine, 4-thiouridine, N6-methyladenosine, pseudouridine, 2,6-diaminopurine, inosine, thymidine, 5-methylcytosine, 5-substituted pyrimidine, isoguanine, isocytosine, and halogenated aromatic.

In an embodiment, the virus is an adenovirus or adeno associated virus (AAV). In an embodiment, the small molecule is a chemotherapeutic agent.

In an embodiment, the cargo comprises one or both of an RNA-guided nuclease and a guide RNA. In an embodiment, the RNA-guided nuclease is a CRISPR nuclease.

In one aspect of the invention, a method of identifying components of a minimal exosome, comprising the steps of: a) subjecting a population of cells to a stress to produce a population of stress-induced exosomes; b) analyzing one or both of the polypeptide content and the lipid content of the stress-induced exosomes; c) comparing one or both of the polypeptide content and the lipid content of the stress-induced exosomes to one or both of the polypeptide content and the lipid content of non-stress-induced exosomes; d) identifying one or more polypeptides and one or more lipids that are unregulated in the stress-induced exosomes compared to the non-stress-induced exosomes, is provided.

In an embodiment, the stress is selected from the group consisting of serum deprivation, oxidation, hypoxia, heat shock, UV radiation, xenobiotic stress, infection, and endoplasmic reticulum (ER) stress.

In an embodiment, the analyzing step b) comprises one or both of performing proteomics and lipidomics.

In an embodiment, the method further comprises step e), wherein one or both of the one or more identified polypeptides and one or more lipids are incorporated into an artificial exosome.

In one aspect of the invention, an artificial exosome comprising rab7, desmoplakin, alpha 2-HS glycoprotein (AHSG), and a cardiolipin or a variant thereof, wherein the artificial exosome is free of a cargo molecule, is provided.

In one aspect of the invention, an artificial exosome comprising rab7, desmoplakin, alpha 2-HS glycoprotein (AHSG), and a cardiolipin or a variant thereof, wherein the artificial exosome is free of any one or more of CD9, CD37, CD63, CD81, CD82, Tsg101, and Alix, and wherein the artificial exosome comprises one or both of 100 or fewer different polypeptides and 100 or fewer different lipids, is provided.

BRIEF DESCRIPTION OF THE DRAWINGS

The foregoing and other features and advantages of the present invention will be more fully understood from the following detailed description of illustrative embodiments taken in conjunction with the accompanying drawings. The patent or application file contains at least one drawing executed in color. Copies of this patent or patent application publication with color drawing(s) will be provided by the Office upon request and payment of the necessary fee.

FIG. 1A depicts umbilical cord derived mesenchymal stem cells that were cultured in either the recommended stem cell medium or in RPMI for differing times. Alamar Blue® was added and incubated at 37° C. for 12 hours, and fluorescence measured at 570 nm excitation, 585 nm emission. Signal is normalized to not serum deprived samples. N=8, mean±SD, one-way ANOVA. FIG. 1B depicts representative size distribution curves of extracellular vesicles (EVs) enriched from umbilical cord-derived mesenchymal stem cells, N=3, mean, Nanoparticle Tracking Analysis. FIG. 1C depicts Western blots of cells, microvesicles and exosomes derived under control or serum deprived conditions from umbilical cord, adipose tissue or bone marrow derived mesenchymal stem cells. Negative marker: calnexin. Positive markers: CD63, Tsg101, CD81. Proteins shown to be enriched in stressed exosomes or stressed cells are Desmoplakin, AHSG, and Rab7.

FIG. 2A depicts yield, FIG. 2C depicts size, and FIG. 2E depicts protein-to-particle ratio of exosomes enriched from conditioned media of control or stressed mesenchymal stem cells via differential ultracentrifugation (100,000 g fraction). FIG. 2B depicts yield, FIG. 2D depicts size, and FIG. 2F depicts protein-to-particle ratio of microvesicles enriched from conditioned media of control or stressed mesenchymal stem cells via differential ultracentrifugation (10,000 g fraction).

FIG. 3A-FIG. 3L depict the effect of serum deprivation of mesenchymal stem cells on exosome and microvesicle activity. Primary neurons were treated with fluorescent siRNA-containing exosomes or microvesicles derived from control or stressed (serum deprived) cells. After 7 days of incubation, siRNA levels and target mRNA levels were quantified in neurons. mRNA levels were normalized to housekeeping gene and to untreated control. N=3, mean±SEM, curves were compared using two-way ANOVA. FIG. 3A-FIG. 3C depict uptake of siRNA into neurons delivered via exosomes. FIG. 3D-FIG. 3F depict mRNA silencing induced by treatment of siRNA-containing exosomes. FIG. 3G-FIG. 3I depict uptake of siRNA into neurons delivered via microvesicles. FIG. 3J-FIG. 3L depict mRNA silencing induced by treatment of siRNA-containing microvesicles. FIG. 3A, FIG. 3D, FIG. 3G, and FIG. 3J depict EVs enriched from umbilical cord derived mesenchymal stem cells. FIG. 3B, FIG. 3E, FIG. 3H, and FIG. 3K depict EVs enriched from adipose tissue derived mesenchymal stem cells. FIG. 3C, FIG. 3F, FIG. 3I, and FIG. 3L depict EVs enriched from bone marrow derived mesenchymal stem cells.

FIG. 5A-FIG. 5C depicts volcano plots of proteins detected in exosome. Orange dots represent proteins enriched at least 2-fold in stressed exosomes and blue dots represent proteins enriched at least 2-fold in control exosomes. Dashed line marks the threshold of significance (p=0.05, t-test with Benjamini-Hochberg correction for multiple comparison). Proteins above the dashed line significantly differ between stressed and control exosomes. Proteins detected in one group and absent in the other group were arbitrarily assigned the fold change of 20 or −20. FIG. 5D-FIG. 5F depict heatmaps of proteins different (p<0.1) in stressed exosomes versus control exosomes. Orange represents enrichment in stressed conditions versus control conditions, whereas blue represents enrichment in control conditions versus stress conditions. FIG. 5G-FIG. 5I depicts Gene Ontology analysis of proteins at least 2-fold enriched in stressed exosomes control exosomes (e.g., proteins labeled orange or blue in FIG. 5A-FIG. 5C.). FIG. 5A, FIG. 5D, and FIG. 5G depict umbilical cord derived mesenchymal stem cells. FIG. 5B, FIG. 5E, and FIG. 5H depict adipose tissue derived mesenchymal stem cells. FIG. 5C, FIG. 5F, and FIG. 5I depict bone marrow derived mesenchymal stem cells.

FIG. 6C depicts enrichment of selected proteins in stressed exosomes versus control exosomes (orange) or in stressed cells versus control cells (grey). Proteins detected in stressed conditions but absent in control conditions were arbitrarily assigned the fold change of 20. N=3, mean±SEM. Two-way ANOVA, ** $p<0.0001$, * $p<0.001$, ** $p<0.01$, * $p<0.05$. FIG. 6D depicts primary neurons were treated with siRNA containing liposomes alone or liposomes incorporating purified proteins from FIG. 3C. and target mRNA levels in neurons quantified after 7 days of incubation. N=4, mean±SEM, two-way ANOVA.

FIG. 7A depicts a heatmap of lipid classes in stressed conditions versus control conditions. Orange represents enrichment in stressed conditions versus control conditions, whereas blue represents enrichment in control conditions versus stress conditions. FIG. 7B depicts a scheme of cardiolipin. Length and saturation of fatty acid tails depicted is representative only and varies between natural cardiolipin species. FIG. 7C depicts a scheme of monolysocardiolipin. Differences to cardiolipin is shown in red. Length and saturation of fatty acid tails depicted is representative only and varies between natural monolysocardiolipin species. FIG. 7D depicts a scheme of dilysocardiolipin. Differences to cardiolipin is shown in red. Length and saturation of fatty acid tails depicted is representative only and varies between natural dilysocardiolipin species. FIG. 7E depicts enrichment of cardiolipin subclasses from FIG. 7B-FIG. 7D in stressed exosomes versus control exosomes. Two-way ANOVA, **** $p<0.0001$. FIG. 7F depicts primary neurons were treated with siRNA containing liposomes alone or liposomes incorporating lipids from FIG. 7E and target mRNA levels in neurons quantified after seven days of incubation. N=4, mean±SEM, two-way ANOVA.

FIG. 8A-FIG. 8C depict the effect of serum deprivation of umbilical cord derived mesenchymal stem cells on lipid composition of exosomes. FIG. 8A depicts a bar graph showing lipid classes in stressed versus control conditions for exosomes, microvesicles, and cells. FIG. 8B depicts the correlation of enrichment in stressed versus control exosomes with the cumulative number of double bonds in the fatty acid tails of a cardiolipin species. FIG. 8C depicts the correlation of enrichment in stressed versus control exosomes with the cumulative length of the fatty acid tails of a cardiolipin species. Each dot represents a cardiolipin species.

FIG. 9A depicts primary neurons that were treated with siRNA containing stressed exosomes, large-scale exosomes, or artificial exosomes and target mRNA levels in neurons quantified after seven days of incubation. Stressed exosomes and large-scale exosomes were enriched from umbilical cord derived mesenchymal stem cells via differential ultracentrifugation or tangential flow filtration, respectively. Artificial exosomes consisted of dioleoylphosphatidylcholine, cholesterol, dilysocardiolipin, Rab7, Desmoplakin, and AHSG. N=5, mean±SEM, two-way ANOVA. FIG. 9B and FIG. 9C depict Huntingtin (HTT)-targeting or non-targeting control (NTC) siRNAs that were infused into the lateral ventricle of mice either alone, or in liposomes, large-scale exosomes, or artificial exosomes. Huntingtin mRNA were quantified four weeks after infusion in striatum (FIG. 9B) and motor cortex (FIG. 9C). N=5-7, mean±SD, one-way ANOVA.

DETAILED DESCRIPTION

Figure 1A:
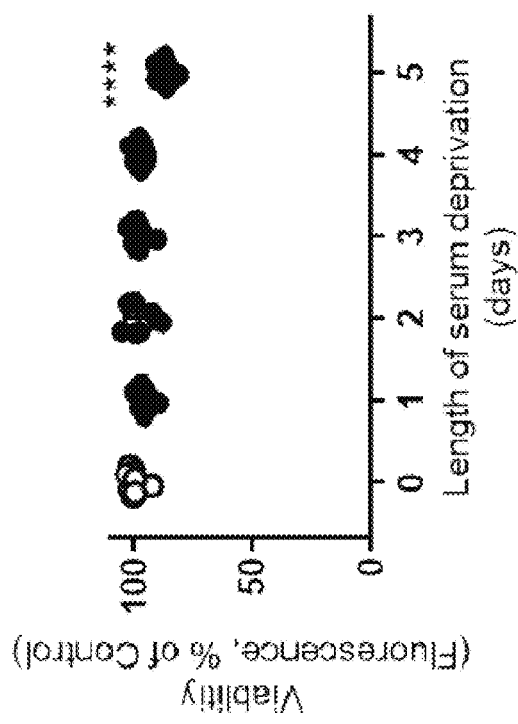
FIG. 1A-FIG. 1C depict the characterization of cell culture conditions and extracellular vesicles.

Provided herewith are novel artificial exosomes. In certain embodiments, artificial exosomes comprising rab7, desmoplakin, alpha 2-HS glycoprotein (AHSG), and a cardiolipin or variant thereof are provided. Methods of producing the artificial exosomes of the invention are also provided. Methods of delivering cargo molecules using the artificial exosomes of the invention for the treatment or prevention of a disease or disorder are also provided.

Exosomes are small vesicles that originate in eukaryotic cells, primarily in the endosomal pathway. Exosomes comprise a plasma membrane and are released from cells into the extracellular environment. Generally, these exosomes are approximately 30-100 nM in diameter, but can range in size from approximately 20 nM to approximately 200 nM. Naturally occurring exosomes are hypothesized to transport molecules from one cell to another. Exosomes are taken up by recipient cells by endocytosis or by fusion of the exosomal membrane with the plasma membrane of the recipient cell.

These and other properties of exosomes have led to their use as delivery vehicles for synthetic cargo, e.g., proteins and nucleic acids. Exosomes are an attractive alternative to liposomes for use as delivery vehicles because they readily cross major biological membranes due to their small size and the nature of their lipid bilayer. Exosomes are well-tolerated by subjects, and are highly stable in biological fluids, which protects exosomal cargo from degradation.

Generally, nomenclature used in connection with cell and tissue culture, molecular biology, immunology, microbiology, genetics and protein and nucleic acid chemistry and hybridization described herein are those well-known and commonly used in the art. The methods and techniques provided herein are generally performed according to conventional methods well known in the art and as described in various general and more specific references that are cited and discussed throughout the present specification unless otherwise indicated. Enzymatic reactions and purification techniques are performed according to manufacturer's specifications, as commonly accomplished in the art or as described herein. The nomenclature used in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

Unless otherwise defined herein, scientific and technical terms used herein have the meanings that are commonly understood by those of ordinary skill in the art. In the event of any latent ambiguity, definitions provided herein take precedent over any dictionary or extrinsic definition. Unless otherwise required by context, singular terms shall include pluralities and plural terms shall include the singular. The use of "or" means "and/or" unless stated otherwise. The use of the term "including," as well as other forms, such as "includes" and "included," is not limiting.

So that the invention may be more readily understood, certain terms are first defined.

As used herein, the term "artificial exosome," "minimal exosome," "synthetic exosome," or "exosome mimetic" refers to an exosome that may be generated synthetically, e.g., from a starting liposome base composition, into which one or more polypeptides and/or lipids may be incorporated. For example, in certain embodiments, an artificial exosome of the disclosure is not secreted, released, or otherwise produced by cells. In certain embodiments, an artificial exosome of the disclosure is not generated by extrusion of cells through filters with diminishing pore size (see, Jang et al. ACS Nano 7(9): 7698-7710 (2013)). In certain embodiments, an artificial exosome of the disclosure may be a natural exosome into which one or more polypeptides and/or lipids may be incorporated.

One advantage of the artificial exosomes of the disclosure over naturally-derived exosomes is the ability to enrich, or increase the content of, select polypeptides and/or lipids compared to what would be expected in a naturally-derived exosome. The enriched polypeptides and/or lipids may confer enhanced properties to the artificial exosomes, such as: enhanced cargo uptake; enhanced retention of cargo; maintaining stability in the plasma membrane; maintaining stability in one or more extracellular fluids of an organism; targeting specific cell types; releasing cargo into and/or around one or more target cells; and the like. An artificial exosome of the disclosure may comprise one or more polypeptides and/or lipids that are enriched relative to a non-artificial or naturally-derived exosome.

As used herein, a "non-artificial exosome" refers to a wild-type (e.g., a naturally-derived) exosome that does not have an enriched lipid and/or protein composition. Non-artificial exosomes may be derived from a variety of cells, tissues and fluids e.g., from a subject or from tissue culture. Non-artificial exosomes include stress-induced exosomes that are derived from cells, tissues or fluids that have been exposed to one or more stresses.

In certain embodiments, an artificial exosome described herein may comprise a limited number and/or type of polypeptides and/or lipids. Naturally-derived exosomes consist of thousands of different polypeptides and lipids (see, Haraszti et al. J Extracell. Vesicles 5, 32570 (2016)). In contrast, the artificial exosomes of the disclosure possess a minimal number of polypeptides and lipids necessary to perform one or more functions of an exosome. For example, in certain embodiments, an artificial exosome may contain only those polypeptides and lipids necessary to deliver cargo to a cell, e.g., to a neuronal cell. Thus, an artificial exosome may also be considered a "minimal exosome."

As used herein, "an artificial exosome function" or "a function of an artificial exosome" refers to a function of a naturally-derived exosome, including, but not limited to, any combination of the following: taking up cargo; retaining cargo; maintaining stability in the plasma membrane; maintaining stability in one or more extracellular fluids of an organism; targeting specific cell types; releasing cargo into and/or around one or more target cells; and the like.

As used herein, an "enriched exosome" refers to a naturally-derived exosome that has been enriched for one or more polypeptides and/or one or more lipids described herein, e.g., one or more lipids and/or one or more proteins that have increased expression in a stress-induced exosome. Alternatively, an "enriched exosome" refers to a non-naturally derived exosome that includes one or more polypeptides and/or one or more lipids having increased (i.e., upregulated) expression in a stress-induced exosome.

As used herein, a "stress-induced exosome" refers to an exosome produced by a cell that is exposed to one or more stress factors such as, e.g., exposure to one or more of serum deprivation, oxidation, hypoxia, heat shock, radiation (e.g., UV radiation), xenobiotic stress, infection (e.g., interferon (IFN) stress), endoplasmic reticulum (ER) stress and the like. The protein and/or lipid composition of a stress-induced exosome is altered relative to the protein and/or lipid composition of a non-stress-induced exosome.

In certain embodiments, an artificial exosome has a reduced number of immunogenic components compared to a non-artificial exosome. In certain embodiments, an artificial exosome excludes immunogenic components.

As used herein, an "immunogenic component" refers to a polypeptide, a protein, a lipid or other exosomal component that elicits an immune response in a subject.

In certain embodiments, a single artificial exosome of the disclosure may comprise about 50 to about 1000 molecules of a particular lipid. An artificial exosome may comprise at least about 50, at least about 100, at least about 200, at least about 300, at least about 400, at least about 500, at least about 600, at least about 700, at least about 800, at least about 900, or at least about 1000 molecules of a particular lipid. In certain embodiments, an artificial exosome of the disclosure may comprise about 100 molecules of a particular lipid. In certain embodiments, an artificial exosome of the disclosure may comprise about 100 molecules of a cardiolipin or variant thereof (e.g., dilysocardiolipin).

An artificial exosome of the disclosure may comprise 1 to 200 different lipids. In certain embodiments, an artificial exosome may comprise 1 to 100 different lipids. In certain embodiments, an artificial exosome may comprise 100 to 200 different lipids. In certain embodiments, an artificial exosome may comprise 10 to 50 different lipids. In certain embodiments, an artificial exosome may comprise no more than 1, 2, 3, 4, 5, 6, 7, 8, 9, 10, 15, 20, 25, 30, 35, 40, 45, 50, 55, 60, 65, 70, 75, 80, 85, 90, 95, or 100 different lipids. In certain embodiments, an artificial exosome of the disclosure may comprise 100 or fewer different polypeptides and/or 100 or fewer different lipids.

In certain embodiments, a single artificial exosome of the disclosure may comprise about 50 to about 1000 molecules of a particular polypeptide (e.g., protein). An artificial exosome may comprise at least about 50, at least about 100, at least about 200, at least about 300, at least about 400, at least about 500, at least about 600, at least about 700, at least about 800, at least about 900, or at least about 1000 molecules of a particular polypeptide (e.g., protein). In certain embodiments, an artificial exosome of the disclosure may comprise about 100 copies of a particular polypeptide (e.g., protein). In certain embodiments, an artificial exosome of the disclosure may comprise about 100 copies of one or more of rab7, desmoplakin, and AHSG.

An artificial exosome of the disclosure may comprise 1 to 200 different polypeptides (e.g., proteins). An artificial exosome may comprise 1 to 100 different polypeptides (e.g., proteins). An artificial exosome may comprise 100 to 200 different polypeptides (e.g., proteins). An artificial exosome may comprise 10 to 50 different polypeptides. An artificial exosome may comprise no more than 1, 2, 3, 4, 5, 6, 7, 8, 9, 10, 15, 20, 25, 30, 35, 40, 45, 50, 55, 60, 65, 70, 75, 80, 85, 90, 95, or 100 different polypeptides (e.g., proteins).

As used herein, a "liposome base composition" refers to a composition of one or more lipids that may be used to generate a liposome into which one or more polypeptide and/or lipids may be incorporated to generate an artificial exosome of the disclosure. The liposome base composition may comprise various mixtures of lipids suitable for the generation of a liposome. Liposomes are typically generated from phospholipids and cholesterol. Liposome properties may differ with lipid composition, surface charge, size, and the method of preparation (see, Akbarzadeh et al. Nanoscale Res. Lett. 8(1): 102 (2013).

In certain embodiments, the liposome base composition may comprise one or more of the following lipids: sterols, such as cholesterol and variants thereof, phosphatidylcholine, phosphatidylglycerol, cardiolipin and variants thereof, distearoylphosphatidylcholine, distearoylphosphatidylglycerol, lecithin, β,γ-dipalmitoyl-α-lecithin, sphingomyelin, phosphatidylserine, phosphatidic acid, N-(2,3-di(9-(Z)-octadecenyloxy))-prop-1-yl-N,N,N-trimethylammonium chloride, phosphatidylethanolamine, lysolecithin, lysophosphatidylethanolamine, phosphatidylinositol, cephalin, cerebrosides, dicetylphosphate, dioleoylphosphatidylcholine, dipalmitoylphosphatidylcholine, dipalmitoylphosphatidylglycerol, dioleoylphosphatidylglycerol, palmitoyl-oleoyl-phosphatidylcholine, di-stearoyl-phosphatidylcholine, stearoyl-palmitoyl-phosphatidylcholine, di-palmitoyl-phosphatidylethanolamine, di-stearoyl-phosphatidylethanolamine, di-myrstoyl-phosphatidylserine, di-oleyl-phosphatidylcholine, and the like. Non-phosphorus containing lipids may also be used in the liposome base of the artificial exosomes of the present disclosure. These include, e.g., stearylamine, docecylamine, acetyl palmitate, fatty acid amides, and the like. Additional lipids suitable for use in the liposome base of the artificial exosomes of the present disclosure are well known to persons of skill in the art and are cited in a variety of well-known sources, e.g., McCutcheon's Detergents and Emulsifiers and McCutcheon's Functional Materials, Allured Publishing Co., Ridgewood, N.J., both of which are incorporated herein by reference. In an exemplary embodiment, the liposome base composition comprises dioleoylphosphatidylcholine (DOPC) and cholesterol.

Lipids to be incorporated into the liposome base composition to generate artificial exosomes may include any one or more of the above recited lipids. The one or more lipids to be incorporated are determined by identifying lipids that confer an activity upon the artificial exosome, such as enhanced stability or enhanced delivery of cargo to a target cell. In certain embodiments, an artificial exosome lipid is a cardiolipin or variant thereof. Variants of cardiolipin may enhance the stability or enhance the delivery of cargo of an artificial exosome to a target cell (e.g., neuronal cell). Variants of cardiolipin may include, but are not limited to, monolysocardiolipin and dilysocardiolipin. In an exemplary embodiment, an artificial exosome lipid comprises dilysocardiolipin.

The liposome base composition and/or artificial exosome may comprise various ratios or % weight amounts of lipids used in their formulation. Suitable amounts of each lipid within a liposome base composition and/or within an artificial exosome may be readily determined by those of skill in the art through routine optimization based on the disclosure provided herein. A particular lipid within a liposome base composition and/or within an artificial exosome may be about 0.1% weight/weight (w/w) to about 99.9% w/w. A particular lipid within a liposome base composition and/or within an artificial exosome may be about 10% w/w to about 90% w/w. A particular lipid within a liposome base composition and/or within an artificial exosome may be about 10% w/w to about 50% w/w. A particular lipid within a liposome base composition and/or within an artificial exosome may be about 50 w/w to about 90% w/w. A particular lipid within a liposome base composition and/or within an artificial exosome may be about 0.1% w/w, about 0.5% w/w, about 1.0% w/w, about 1.5% w/w, about 2.0% w/w, about 2.5% w/w, about 3.0% w/w, about 3.5% w/w, about 4.0% w/w, about 4.5% w/w, about 5.0% w/w, about 5.5% w/w, about 6.0% w/w, about 6.5% w/w, about 7.0% w/w, about 7.5% w/w, about 8.0% w/w, about 8.5% w/w, about 9.0% w/w, about 9.5% w/w, about 10.0% w/w, about 15% w/w, about 20% w/w, about 25% w/w, about 30% w/w, about 35% w/w, about 40% w/w, about 45% w/w, about 50% w/w, about 55% w/w, about 60% w/w, about 65% w/w, about 70% w/w, about 75% w/w, about 80% w/w, about 85% w/w, about 90% w/w, about 95% w/w, about 95.5% w/w, about 96.0% w/w, about 96.5% w/w, about 97.0% w/w, about 97.5% w/w, about 98.0% w/w, about 98.5% w/w, about 99.0% w/w, or about 99.9% w/w. In certain embodiments, the liposome base composition and/or artificial exosome comprises DOPC and cholesterol at a ratio of about 70%: 30% w/w DOPC:cholesterol. In an exemplary embodiment, the liposome base composition and/or artificial exosome comprises DOPC, cholesterol, and dilysocardiolipin at a ratio of about 40%:30%:30% w/w DOPC:cholesterol:dilysocardiolipin.

The artificial exosomes of the disclosure further comprise one or more polypeptides (e.g., proteins). The polypeptides (e.g., proteins) of the artificial exosomes confer various functional properties, such as cell targeting or stability. In certain embodiments, the polypeptides (e.g., proteins) are from an endosomal pathway (such as Rab family proteins, including Rab5 and Rab7) (see, Kummel et al. Curr. Opin. Cell Biol. 29: 61-66 (2014)), are involved in plasma membrane budding (such as ARRDC1) (see, Nabhan et al. Proc. Natl. Acad. Sci. 109: 4146-4151 (2012), are secreted proteins that interact with membranes (such as dermcidin) (see, Paulmann et al. J. Biol. Chem. 287: 8434-8443 (2012)), are desmosome proteins (such as desmocollin and desmoplakin) (see, Delva et al. Cold Spring Harb. Perspect. Biol. 1: a002543 (2009)), and/or are nucleo-extracellular shuttles (such as alpha 2-HS glycoprotein and histone 1) (see, Watson et al. FEBS Lett. 586: 3458-3463 (2012)). In certain embodiments, the polypeptides (e.g., proteins) are any one or more of rab7, desmoplakin, and alpha 2-HS glycoprotein (AHSG).

In certain embodiments, a polypeptide (e.g., a protein) to be incorporated in an artificial exosome is modified to facilitate incorporation. A polypeptide may comprise a "lipid anchor" or "membrane anchor" to facilitate incorporation. In certain embodiments, a polypeptide (e.g., a protein) is modified with an acyl group or acylation tag. In certain embodiments, a polypeptide (e.g., a protein) may be myristoylated. In certain embodiments, a polypeptide (e.g., a protein) may be palmitoylated. In certain embodiments, a polypeptide (e.g., a protein) may be prenylated. In certain embodiments, a polypeptide (e.g., a protein) may be glypiated (glycophosphatidylinositol or GPI tagged).

Acylation, such as palmitoylation and myristoylation, prenylation, and glypiation may be done chemically. For example, but in no way limiting, the lipid anchor may be modified to contain an amine-reactive crosslinker, such as an N-hydroxysuccinimide ester (NHS) crosslinker. This lipid anchor-NHS compound may be incubated with the polypeptides, which will react with lysines on said polypeptides and form a covalent bond. By way of further example, the polypeptides may be incubated with Palmitic acid N-hydroxysuccinimide ester (palmitoyl-NHS) to palmitoylate the polypeptides. The polypeptide sequence may also be modified to incorporate a peptide signal that triggers the incorporation of the acylation, prenylation, or glypiation tag when expressed in a cell. Non-limiting examples of peptide signals or peptide motifs that trigger any of the above modifications include CCKVL (dual prenylation/palmitoylation tag), CKVL (prenylation tag), QPARV (palmitoylation tag), GXXX(S/T/C) (myristoylation tag). Additional examples and disclosure may be found in Aicart-Ramos et al. BBA-Biomembranes. 1808(12): 2981-2994 (2011).

In addition to the above recited lipid anchor modifications, the polypeptide lipid anchor may comprise a transmembrane domain fusion, a phosphatidylinositol-(4,5)-bisphosphate ($PIP_2$)-binding domain, or a phosphatidylinositol-(3,4,5)-trisphosphate (PIPS)-binding domain. Non-limiting examples of fusion domains include PDZ domains, and pleckstrin homology (PH) domains. Additional examples and disclosure regarding lipid anchors may be found in Shen et al. J. Biol. Chem. 286(16): 14383-14395 (2011) and Baumann et al. Biochemistry of Lipids, Lipoproteins, and Membranes, Ch, 2 (2002).

In certain embodiments, an artificial exosome of the disclosure may be free of select protein markers that are commonly found in naturally-derived exosomes. In certain embodiments, protein markers are excluded from the artificial exosomes if they do not provide a functional advantage. In certain embodiments, an artificial exosome is free of one or any combination of CD9, CD37, CD63, CD81, CD82, Tsg101, and Alix.

An artificial exosome of the disclosure may be free of immunogenic components. Naturally-derived exosomes may be used for therapeutic purposes; however they are often isolated from human cells and may contain components that elicit immune responses which, in turn, may contribute to toxicities or enhanced exosome clearance (see, Quah et al. Blood Cells Mol. Dis. 35(2): 94-110 (2005); Zhu et al. J. Extracell Vesicles 6(1): 1324730 (2017)). An artificial exosome of the disclosure can be designed to exclude immunogenic components, such as immunogenic polypeptides and/or immunogenic lipids, that may be found in naturally-derived exosomes. Accordingly, the artificial exosomes of the disclosure may be more efficacious for therapeutic uses because they may not elicit immune responses.

An artificial exosome of the disclosure may comprise exogenously-derived cargo. As used herein, the terms "exogenous cargo" or "exogenously-derived cargo" refer to one or more compounds that may be loaded into the artificial exosomes that are not found in naturally-derived exosomes.

Synthesis and Isolation of Artificial Exosomes

The artificial exosomes of the disclosure may be synthesized using any common method known in the art for liposome synthesis.

Persons of skill will appreciate that the artificial exosomes of the present disclosure may be synthesized by a variety of methods, such as described in, e.g., U.S. Pat. Nos. 4,186,183; 4,217,344; 4,261,975; 4,485,054; 4,774,085; 4,946,787; PCT Publication No. WO 91/17424, Deamer and Bangham, Biochim. Biophys. Acta, 443:629-634 (1976); Fraley et al., Proc. Natl. Acad. Sci. USA, 76:3348-3352 (1979); Hope et al., Biochim. Biophys. Acta, 812:55-65 (1985); Mayer et al., Biochim. Biophys. Acta, 858:161-168 (1986); and Williams et al., Proc. Natl. Acad. Sci., 85:242-246 (1988), each of which is incorporated herein by reference. Suitable methods include, e.g., sonication, extrusion, high pressure/homogenization, micro-fluidization, detergent dialysis, calcium-induced fusion of small liposome vesicles, and ether-infusion methods, all well known in the art.

Generally, an artificial exosome may be prepared by dissolving lipid components into an organic solvent, e.g., chloroform, a chloroform:methanol mixture, tertiary butanol, or cyclohexane. If lipid-soluble cargo is to be loaded into the artificial exosome, said cargo may be included at this step. After complete homogenization of the lipids in the organic solvent, the solvent is removed to produce a dry lipid film. The organic solvent may be removed by evaporation, such as with a nitrogen or argon stream in a fume hood, or by rotary evaporation. A vacuum pump may be used to fully dry the resulting lipid film. The resulting dry lipid film is rehydrated in a suitable aqueous buffer. If water-soluble cargo is to be loaded into the artificial exosome, said cargo may be included at this step. Suitable aqueous buffers include, but are not limited to, Phosphate Buffered Saline (PBS), 4-(2-hydroxyethyl)-1-piperazineethanesulfonic acid (HEPES), and tris(hydroxymethyl)aminomethane (Tris). The rehydration generally produces multilamellar vesicles. Unilamellar vesicles are prepared by sonication or extrusion.

Sonication is generally performed with a tip sonifier, such as a Branson tip sonifier, in an ice bath. Typically, the suspension is subjected to several sonication cycles (see, Mendez et al. "Sonication-Based Basic Protocol for Liposome Synthesis" Lipidomics. Methods in Molecular Biology, vol. 1609 (2017)). Extrusion may be carried out by biomembrane extruders, such as the Lipex Biomembrane Extruder or the Avanti Polar Lipids Mini-Extruder. Extrusion is performed through a membrane or filter containing pores of appropriate size to produce the artificial exosomes. For example, but in no way limiting, the extrusion may be performed through a 50-nm pore sized polycarbonate membrane. Defined pore size in the extrusion filters may generate unilamellar artificial exosomes of specific sizes. The artificial exosomes may also be formed by extrusion through an asymmetric ceramic filter, such as a Ceraflow Microfilter, commercially available from the Norton Company, Worcester Mass.

The polypeptides incorporated into the artificial exosomes of the disclosure may be added during the lipid film rehydrating step with the aqueous buffer or they may be added after the sonication or extrusion step. In either event, the artificial exosomes may then be isolated by any method known in the art for liposomes. For example, but in no way limiting, the artificial exosomes may be isolated by centrifugation. The centrifugation may be performed at about 100,000 g for a time appropriate to pellet the artificial exosomes.

Cargo for Loading Exosomes

Artificial exosomes of the disclosure may be loaded with one or more cargo agents for delivery. As used herein, "cargo," "cargo molecule," or "cargo agent" refers to a compound that may be loaded into an artificial exosome of the disclosure. Cargo-loaded artificial exosomes may be used to deliver said cargo to certain cell types in vitro, ex vivo, or in vivo. Cargo that may be loaded into an artificial exosome of the disclosure includes, but is not limited to, a peptide, a polypeptide, a nucleic acid, a virus, a small molecule, and a fluorophore, or any combinations thereof. In certain embodiments, cargo for use in therapeutic purposes, e.g., for delivery of a chemotherapeutic agent, or for diagnostic purposes, may be loaded into an artificial exosome of the disclosure. In certain embodiments, the cargo molecule is a heterologous cargo molecule, i.e., the cargo molecule is not naturally occurring in an exosome. For example, but in no way limiting, the heterologous cargo molecule may be a heterologous peptide, a heterologous polypeptide, a heterologous nucleic acid, a heterologous virus, a heterologous small molecule, a heterologous fluorophore, or any combinations thereof.

The cargo may be further modified to contain a hydrophobic moiety, such as a sterol, GM1, a lipid, a vitamin, a small molecule, or a peptide, or a combination thereof. The hydrophobic moiety may facilitate loading of the cargo into the artificial exosomes of the disclosure.

Oligonucleotide Cargo

As used herein, an "oligonucleotide" refers to a nucleic acid agent which may be loaded into an artificial exosome of the disclosure as cargo. The nucleic acid may DNA or RNA and may comprise one or more modifications. Non-limiting examples of oligonucleotide molecules which can be loaded into artificial exosomes as described herein include siRNA, siRNA-GalNAc, antisense molecules, locked nucleic acids (LNAs), hairpin siRNA, phosphorodiamidate morpholino oligomers (PMOs), miRNA, and oligonucleotide miRNA inhibitors. In some embodiments, the oligonucleotide molecules are plasmid DNA, which can be modified with a hydrophobic modification post-transcriptionally. In an exemplary embodiment, an oligonucleotide cargo is an siRNA. In another exemplary embodiment, an oligonucleotide cargo is a hairpin siRNA. In another exemplary embodiment, an oligonucleotide cargo is an miRNA.

In certain embodiments, the oligonucleotide cargo is capable of modifying gene expression in a target cell. For example, the oligonucleotide cargo may reduce or inhibit expression of one or more genes in a target cell. This can occur by way of direct targeting of DNA or RNA through Watson-Crick base pairing. By way of example, cargo molecules capable of reducing or inhibiting expression of one or more genes in a target cell can include siRNA, siRNA-GalNAc, antisense, Locked Nucleic Acids (LNAs), hairpin siRNA, phosphorodiamidate morpholino oligomers (PMOs), miRNA, and oligonucleotide miRNA inhibitors. In other embodiments, the oligonucleotide cargo may increase expression of one or more genes in a target cell. By way of example, cargo molecules capable of increasing expression of one or more genes in a target cell include expression vectors and oligonucleotide miRNA inhibitors.

In some embodiments, the oligonucleotide cargo is a therapeutic oligonucleotide. A therapeutic oligonucleotide is useful in treating or ameliorating the signs and symptoms of a disease or disorder when administered to a subject. For example, a therapeutic oligonucleotide can target a gene involved in a disease process, thereby reducing the symptoms of the disease in a subject to whom the therapeutic oligonucleotide is administered. In order to facilitate artificial exosomal loading, oligonucleotide cargo contains one or more hydrophobic modifications. Hydrophobic modifications increase the hydrophobicity of the oligonucleotide cargo, as compared to native (non-modified) oligonucleotides. In certain embodiments, the hydrophobic modifications increase the hydrophobicity of the oligonucleotide by at least two orders of magnitude (e.g., at least 3, 4, 5, 6, 7, 8, 9, 10 or more orders of magnitude) relative to native (non-modified) oligonucleotides. In other embodiments, the hydrophobic modifications increase the hydrophobicity of the oligonucleotide by at least 10 orders of magnitude relative to native (non-modified) oligonucleotides. In other embodiments, the hydrophobic modifications increase the hydrophobicity of the oligonucleotide by at least two orders of magnitude (e.g., at least 3, 4, 5, 6, 7, 8, 9, 10 or more orders of magnitude) relative to the unmodified oligonucleotide. In other embodiments, the hydrophobic modifications increase the hydrophobicity of the oligonucleotide by at least ten orders of magnitude relative to the unmodified oligonucleotide. Increases in hydrophobicity can be assessed using any suitable method. For example, hydrophobicity can be determined by measuring the percentage solubility in an organic solvent, such as octanol, as compared to solubility in an aqueous solvent, such as water.

In some embodiments, the hydrophobic character of oligonucleotide cargo can be increased by increasing the proportion of nucleotides within the oligonucleotide molecule that are hydrophobically modified. For example, in one embodiment, 20% or more of the nucleotides in an oligonucleotide molecule are hydrophobically modified, e.g., 25% or more, 30% or more, 40% or more, 50% or more, 60% or more, 70% or more, 80% or more, 90% or more, 95% or more, 99% or more, etc. of the nucleotides in an oligonucleotide molecule are hydrophobically modified. In one embodiment, 100% of the nucleotides in an oligonucleotide molecule are hydrophobically modified. In an exemplary embodiment, 30% or more of the nucleotides in an oligonucleotide molecule contain hydrophobic modifications.

Increasing the proportion of hydrophobically modified nucleotides in an oligonucleotide molecule can be useful when, for example, the hydrophobic modification is weakly hydrophobic, for example, a 2'O-methyl modification. In embodiments where a strongly hydrophobic modification is employed, for example, a sterol, a lipid, etc., a single hydrophobic modification can be sufficient to facilitate artificial exosomal loading.

Hydrophobic modifications of nucleic acid molecules can include, for example, backbone modifications, sugar modifications, base modifications and/or conjugate modifications, and combinations thereof.

Backbone modifications involve alterations to the phosphate ester linkages in the nucleic acid molecule. Examples of suitable backbone modifications include, but are not limited to, phosphorothioate modifications, phosphorodithioate modifications, p-ethoxy modifications, methylphosphonate modifications, methylphosphorothioate modifications, alkyl- and aryl-phosphates (in which the charged phosphonate oxygen is replaced by an alkyl or aryl group), alkylphosphotriesters (in which the charged oxygen moiety is alkylated), peptide nucleic acid (PNA) backbone modifications, locked nucleic acid (LNA) backbone modifications, and the like. These modifications may be used in combination with each other and/or in combination with phosphodiester backbone linkages.

In one embodiment, the hydrophobic modification is a phosphorothioate (PS) modification, where one of the non-bridging phosphate oxygen atoms is replaced by sulfur to give a PS group (see, for example, Eckstein, Biochimie. 2002, 84, 841-848). This modification provides significant resistance to nuclease degradation and has favorable pharmacokinetic properties (Bumcrot et al, Nat. Chem. Biol. 2006, 2, 711-719). PS linkages can readily incorporated into oligonucleotide molecules using standard techniques, such as solid-phase oligonucleotide synthesis (Sanghvi, Current Protocols in Nucleic Acid Chemistry, 2011, 4.1.1-4.1.22). In another embodiment, the hydrophobic modification is a phosphonate modification, in which one nonbridging oxygen is replaced with an alkyl group. In other embodiments, the hydrophobic modification is a peptide nucleic acid (PNA) modification. PNAs are oligonucleotide mimics that have a peptide backbone with a neutral charge, as compared with the highly charged sugar-phosphate backbone of native RNA and DNA (see, for example, Nielsen et al, Science 1991, 254, 1497-1500; Demidov et al, Biochem Pharmacol, 1994, 48, 1310-1313). In other embodiments, the hydrophobically modified nucleic acid molecule is a phosphorodiamidate morpholino oligonucleotide (PMO).

In other embodiments, oligonucleotide cargo molecules may be hydrophobically modified at the sugar moiety (e.g., ribose, deoxyribose, etc.). Sugar modifications often occur at the 2' position of the sugar ring, where, for example, the 2' moiety can be modified or substituted with a hydrophobic moiety, such as a halo, alkoxy, aminoalkoxy, alkyl, azido or amino group. In non-limiting examples, sugar modifications can include O-methyl, F, methoxy-ethyl, and 2'-deoxy-2'-fluoroarabinonucleotide (FANA). Other 2' modifications include, for example, 2'O-allyl, 2'O-ethylamine, and 2'O-cyanoethyl modifications. In addition, modifications can be made at other sites including the 4' position of the sugar (see, for example, Deleavey, et al, Chem Bio, 2012, 19, 937-954).

In other embodiments, oligonucleotide cargo molecules may contain hydrophobic base modifications. In exemplary embodiments, these modifications include phenyl, naphthyl, and isobutyl. Other embodiments include C-5 propynyl modified bases, 5-methylcytosine, 2-aminopurine, 2-amino-6-chloropurine, 2,6-diaminopurine, and hypoxanthine. In addition to increasing the hydrophobic character of the oligonucleotide cargo, the foregoing backbone, sugar, and base modifications increase the stability of the oligonucleotides in the presence of artificial exosomes, and minimize any degradation that may occur during loading. Hydrophobic moieties can also be chemically conjugated to oligonucleotide cargo to enhance its hydrophobic character. In exemplary embodiments, the moiety is a sterol (e.g., cholesterol), GM1, a lipid, a vitamin, a small molecule, a peptide, or a combination thereof. In some embodiments, the moiety is a lipid. For example, in certain embodiments, the moiety is palmitoyl. In some embodiments, the moiety is a sterol, e.g., cholesterol. Additional hydrophobic moieties include, for example, phospholipids, vitamin D, vitamin E, squalene, and fatty acids. In another exemplary embodiment, the oligonucleotide cargo is conjugated to myristic acid, or a derivative thereof (e.g., myristoylated oligonucleotide cargo). In some embodiments, the hydrophobic moiety is conjugated at the termini of the oligonucleotide cargo (i.e., "terminal modification"). In other embodiments, the hydrophobic moiety is conjugated to other portions of the oligonucleotide molecule.

In one embodiment, the oligonucleotide cargo is stabilized by incorporation of one or more backbone modifications, sugar modifications, and/or base modifications as described herein, and additionally is conjugated to a hydrophobic moiety.

In certain embodiments, the oligonucleotide cargo can contain one or more backbone modifications, sugar modifications, and/or base modifications to at least 30%, at least 35%, at least 40%, at least 45%, at least 50%, at least 55%, at least 60%, at least 65% or more of the nucleotides, and further is conjugated to a hydrophobic moiety as described herein, e.g., conjugated to a sterol, GM1, a lipid, a vitamin, a small molecule, or a peptide, or a combination thereof. In an exemplary embodiment, the oligonucleotide cargo is conjugated to a sterol, e.g., cholesterol. In another exemplary embodiment, the oligonucleotide cargo is conjugated to GM1. In another exemplary embodiment, the oligonucleotide cargo is conjugated to myristic acid, or a derivative thereof. In one embodiment, the oligonucleotide cargo is an siRNA that contains a short duplex region (for example, 14-16 base pairs, e.g., 15 base pairs), and a single-stranded fully phosphorothioated tail. In this exemplary construct, pyrimidines are modified with 2'-fluoro and 2'-O-methyl modifications. The 3' end of the passenger strand of this exemplary construct is conjugated to cholesterol.

In some embodiments, the hydrophobically modified oligonucleotide can include a detectable label. Exemplary labels include fluorescent labels and/or radioactive labels. In embodiments where hydrophobically modified oligonucleotides are fluorescently labeled, the detectable label can be, for example, Cy3. Adding a detectable label to hydrophobically modified oligonucleotides can be used as a way of labeling exosomes, and following their biodistribution. In other embodiments, a detectable label can be attached to artificial exosomes directly, for example, by way of labeling an artificial exosomal lipid and/or an artificial exosomal protein.

Nucleic acids can be synthesized using any number of procedures known in the art. A number of automated nucleic acid synthesizers are commercially available for this purpose. In an exemplary embodiment, the nucleic acid cargo is a synthetic oligonucleotide. In other embodiments, nucleic acids can be prepared using, for example, restriction enzymes, exonucleases, or endo nucleases.

Oligonucleotides may be hydrophobically modified for loading into the artificial exosomes of the disclosure. Currently, a predominant obstacle to the commercialization of exosomes as a delivery vehicle for oligonucleotides is highly inefficient loading. This obstacle can be overcome by hydrophobically modifying nucleic acid cargo prior to loading the cargo into artificial exosomes. As described herein, hydrophobic modification of oligonucleotide cargo facilitates loading of oligonucleotides into artificial exosomes. Without wishing to be bound by theory, it is proposed that hydrophobic modification of oligonucleotide cargo allows self-assembly of the cargo into the artificial exosomes. Hydrophobic modification of oligonucleotide cargo permits exosomal loading in the absence of electroporation, and without the use of transfection reagents, e.g., cationic liposome transfection reagents. Hydrophobic modification of oligonucleotide cargo also permits exosomal loading without the need for ultracentrifugation (however, in some embodiments, ultracentrifugation may nonetheless be useful for purification of artificial exosomes prior to or after loading).

Hydrophobically modified oligonucleotide cargo can be loaded into exosomes with significantly improved efficiency relative to that which is generally reported for methods of loading exosomes by traditional methods, for example, electroporation, lipid-mediated transfection, or ultracentrifugation.

Accordingly, in some embodiments, the disclosure features a method of loading artificial exosomes with oligonucleotide cargo by incubating a hydrophobically modified oligonucleotide with a population of artificial exosomes for a period of time sufficient to permit loading of the artificial exosomes with the hydrophobically modified oligonucleotide.

In other embodiments, the disclosure features a method of loading artificial exosomes with oligonucleotide cargo, by introducing one or more hydrophobic modifications into the oligonucleotide cargo, and incubating the hydrophobically modified oligonucleotide with a population of artificial exosomes for a period of time sufficient to permit loading of the artificial exosomes with the hydrophobically modified oligonucleotide.

The duration of time sufficient to permit loading of the artificial exosomes with hydrophobically modified oligonucleotide cargo can be optimized for the particular type of cargo and the type of modification. Generally, an incubation of 1 hour or less is sufficient to permit efficient loading of artificial exosomes with hydrophobically modified cargo. In many instances, hydrophobically modified cargo is efficiently loaded into artificial exosomes in a very rapid period of time, for example, within 5 minutes. Accordingly, in some embodiments, efficient loading takes place during an incubation period of 5 minutes or less, e.g., from 1-5 minutes. In further embodiments, efficient loading takes place during an incubation period of 5 minutes, 10 minutes, 15 minutes, 20 minutes, 30 minutes, etc. In other embodiments, efficient loading may take place within 1 hour, within 2 hours, within 3 hours, within 4 hours, within 5 hours, within 6 hours, within 7 hours, within 8 hours, within 9 hours, within 10 hours, within 12 hours, within 24 hours, etc.

Loading of artificial exosomes with hydrophobically modified oligonucleotides is not highly temperature dependent. In certain embodiments, artificial exosomes are loaded at or around 37° C. In other embodiments, artificial exosomes can be loaded at or around room temperature. In other embodiments, artificial exosomes can be loaded at or around 4° C.

Gene Editing Complex Cargo

As used herein, "gene editing complex" refers to a biologically active molecule (e.g., a protein, one or more proteins, a nucleic acid, one or more nucleic acids, or any combination of the foregoing) configured for adding, disrupting or changing genomic sequences (e.g., a gene sequence) by causing a genetic lesion (e.g., double stranded break (DSB) or single stranded break (SSB)) in a target DNA or other target nucleic acid, which may be loaded into an artificial exosome of the disclosure as cargo. The genetic lesion may be introduced in a number of ways known in the art. Examples of gene editing complexes include but are not limited nucleases such as transcription activator-like effector nucleases (TALENs), zinc finger nucleases (ZFNs), engineered meganuclease re-engineered homing endonucleases, the CRISPR/Cas system, and meganucleases (e.g., Meganuclease I-SceI). In some embodiments, a gene editing complex comprises proteins or molecules (e.g., components) related to the CRISPR system, including but not limited to Cas9, Cas6, dCas9, CRISPR RNA (crRNA), trans-activating crRNA (tracrRNA), and variants thereof. In some embodiments, the Cas protein is a Cpf1 protein, or a variant thereof.

As used herein, the terms "endonuclease" and "nuclease" refer to an enzyme that cleaves a phosphodiester bond or bonds within a polynucleotide chain. Nucleases may be naturally occurring or genetically engineered. Genetically engineered nucleases are particularly useful for genome editing and are generally classified into four families: zinc finger nucleases (ZFNs), transcription activator-like effector nucleases (TALENs), meganucleases (e.g., engineered meganucleases) and RNA guides nucleases such as the CRISPR-associated proteins (Cas nucleases).

Meganucleases

A meganuclease, such as a homing endonuclease, refers to a double-stranded endonuclease having a polynucleotide recognition site of 14-40 base pairs, which can be either monomeric or dimeric, which may be loaded into an artificial exosome of the disclosure as cargo. Meganucleases can be designed and predicted according to the procedures in US 2014/0121115 can be used in the present methods. A "custom-made meganuclease" refers to a meganuclease derived from a parental meganuclease that possesses recognition and/or cleavage that is altered from the parental meganuclease. Exemplary meganucleases include, but are not limited to, I-Sce I, I-Chu I, I-Dmo I, I-Cre I, I-Csm I, PI-Sce I, PI-Tli I, PI-Mtu I, I-Ceu I, I-Sce II, I-Sce III, HO, PI-Civ I, PI-Ctr I, PI-Aae I, PI-Bsu I, PI-Dha I, PI-Dra I, PI-May I, PI-Mch I, PI-Mfu I, PI-Mfl I, PI-Mga I, PI-Mgo I, PI Min I, PI-Mka I, PI-Mle I, PI-Mma I, PI-Msh I, PI-Msm I, PI-Mth I, PI-Mtu I, PI-Mxe I, PI-Npu I, PI-Pfu I, PI-Rma I, PI-Spb I, PI-Ssp I, PI-Fac I, PI-Mja I, PI-Pho I, PI-Tag I, PI-Thy I, PI-Tko I, and PI-Tsp I. Particular exemplary meganucleases include I-Sce I, I-Chu I, I-Dmo I, I-Cre I, I-Csm I, PI-Sce I, PI-Pfu I, PI-Tli I, PI-Mtu I, and I-Ceu I. Other particular exemplary meganucleases include I-Dmo I, I-Cre I, PI-Sce I, and PI-Pfu I. Homing endonucleases generally cleave their DNA substrates as dimers, and do not have distinct binding and cleavage domains.

Zinc Finger Nucleases

Zinc finger nucleases (ZFNs) are enzymes having a DNA cleavage domain and a DNA binding zinc finger domain, which may be loaded into an artificial exosome of the disclosure as cargo. ZFNs may be made by fusing the nonspecific DNA cleavage domain of an endonuclease with site-specific DNA binding zinc finger domains. Such nucleases are powerful tools for gene editing and can be assembled to induce double strand breaks (DSBs) site-specifically into genomic DNA. ZFNs allow specific gene disruption as during DNA repair, the targeted genes can be disrupted via mutagenic non-homologous end joint (NHEJ) or modified via homologous recombination (HR).

Zinc finger proteins can be designed and predicted according to the procedures in WO 98/54311, U.S. Pat. Nos. 9,187,758, 9,206,404 and 8,771,985 can be used in the present methods. WO 98/54311 discloses technology which allows the design of zinc finger protein domains that bind specific nucleotide sequences that are unique to a target gene. It has been calculated that a sequence comprising 18 nucleotides is sufficient to specify a unique location in the genome of higher organisms. Typically, therefore, the zinc finger protein domains are hexadactyl, i.e., contain 6 zinc fingers, each with its specifically designed alpha helix for interaction with a particular triplet. However, in some instances, a shorter or longer nucleotide target sequence may be desirable. Thus, the zinc finger domains in the proteins may contain at least 3 fingers, or from 2-12 fingers, or 3-8 fingers, or 3-4 fingers, or 5-7 fingers, or even 6 fingers. In one aspect, the ZFP contains 3 zinc fingers; in another aspect, the ZFP contains 4 zinc fingers. Additional description on ZFNs and their design for genome editing may be found in US 20120329067A1, incorporated herein by reference.

Transcription Activator Like Effector Nucleases (TALENs)

Transcription activator-like effector nucleases (TALENs) are artificial restriction enzymes generated by fusing the TAL effector DNA binding domain to a DNA cleavage domain, which may be loaded into an artificial exosome of the disclosure as cargo. These reagents enable efficient, programmable, and specific DNA cleavage and represent powerful tools for genome editing in situ. Transcription activator-like effectors (TALEs) can be quickly engineered to bind practically any DNA sequence. The term TALEN, as used herein, is broad and includes a monomeric TALEN that can cleave double stranded DNA without assistance from another TALEN. The term TALEN is also used to refer to one or both members of a pair of TALENs that are engineered to work together to cleave DNA at the same site. TALENs that work together may be referred to as a left-TALEN and a right-TALEN, which references the handedness of DNA. See U.S. Ser. No. 12/965,590; U.S. Ser. No. 13/426,991 (U.S. Pat. No. 8,450,471); U.S. Ser. No. 13/427,040 (U.S. Pat. No. 8,440,431); U.S. Ser. No. 13/427,137 (U.S. Pat. No. 8,440,432); and U.S. Ser. No. 13/738,381, and U.S. Pat. No. 9,393,257, all of which are incorporated by reference herein in their entirety.

TAL effectors are proteins secreted by *Xanthomonas* bacteria. The DNA binding domain contains a highly conserved 33-34 amino acid sequence with the exception of the 12th and 13th amino acids. These two locations are highly variable (repeat variable di-residue (RVD)) and show a strong correlation with specific nucleotide recognition. This simple relationship between amino acid sequence and DNA recognition has allowed for the engineering of specific DNA binding domains by selecting a combination of repeat segments containing the appropriate RVDs.

The non-specific DNA cleavage domain from the end of the Fok1 endonuclease can be used to construct hybrid nucleases that are active in a yeast assay. These reagents are also active in plant cells and in animal cells. Initial TALEN studies used the wild-type Fok1 cleavage domain, but some subsequent TALEN studies also used Fok1 cleavage domain variants with mutations designed to improve cleavage specificity and cleavage activity. The Fok1 domain functions as a dimer, requiring two constructs with unique DNA binding domains for sites in the target genome with proper orientation and spacing. Both the number of amino acid residues between the TALEN DNA binding domain and the Fok1 cleavage domain and the number of bases between the two individual TALEN binding sites are parameters for achieving high levels of activity. The number of amino acid residues between the TALEN DNA binding domain and the Fok1 cleavage domain may be modified by introduction of a spacer (distinct from the spacer sequence) between the plurality of TAL effector repeat sequences and the Fok1 endonuclease domain. The spacer sequence may be 12 to 30 nucleotides.

The relationship between amino acid sequence and DNA recognition of the TALEN binding domain allows for designable proteins. In this case artificial gene synthesis is problematic because of improper annealing of the repetitive sequence found in the TALE binding domain. One solution to this is to use a publicly available software program (DNAWorks) to calculate oligonucleotides suitable for assembly in a two-step PCR; oligonucleotide assembly followed by whole gene amplification. A number of modular assembly schemes for generating engineered TALE constructs have also been reported. Both methods offer a systematic approach to engineering DNA binding domains that is conceptually similar to the modular assembly method for generating zinc finger DNA recognition domains.

Once the TALEN genes have been assembled they are inserted into plasmids; the plasmids are then used to transfect the target cell where the gene products are expressed and enter the nucleus to access the genome. TALENs can be used to edit genomes by inducing double-strand breaks (DSB), which cells respond to with repair mechanisms. In this manner, they can be used to correct mutations in the genome which, for example, cause disease.

In certain embodiments, the TALEN is a MegTALEN or MegaTAL. MegaTALs are fusion proteins that combine homing endonucleases with modular DNA binding domains of TALENs, resulting in improved DNA sequence targeting and increased gene editing efficiencies. N-terminal fusions of TAL anchors can be employed to increase the specificity and activity of a gene-targeted endonuclease, including one or more homing endonucleases such as one or more of the I-HjeMI, I-CpaMI, and I-Onul homing endonucleases. MegaTALs can be constructed using the Golden Gate assembly strategy described by Cermak et al, Nucl. Acids Res. 39:e82-e82 (2011), using, e.g., an RVD plasmid library and destination vector. MegaTALs can be designed and predicted according to the procedures in WO 2013/126794 and WO 2014/191525 can be used in the present methods.

RNA-Guide Nucleases

RNA-guided nucleases according to the present disclosure include, without limitation, naturally-occurring Class II CRISPR nucleases such as Cas9 (Type II) or Cas12a/Cpf1 (Type V), as well as other nucleases derived or obtained therefrom, which may be loaded into an artificial exosome of the disclosure as cargo. Exemplary Cas9 nucleases that may be used in the present invention include, but are not limited to, *S. pyogenes* Cas9 (SpCas9), *S. aureus* Cas9 (SaCas9), *N. meningitidis* Cas9 (NmCas9), *C. jejuni* Cas9 (CjCas9), and *Geobacillus* Cas9 (GeoCas9). In functional terms, RNA-guided nucleases are defined as those nucleases that: (a) interact with (e.g., complex with) a gRNA; and (b) together with the gRNA, associate with, and optionally cleave or modify, a target region of a DNA that includes (i) a sequence complementary to the targeting domain of the gRNA and, optionally, (ii) an additional sequence referred to as a "protospacer adjacent motif," or "PAM," which is described in greater detail below. As the following examples will illustrate, RNA-guided nucleases can be defined, in broad terms, by their PAM specificity and cleavage activity, even though variations may exist between individual RNA-guided nucleases that share the same PAM specificity or cleavage activity. Skilled artisans will appreciate that some aspects of the present disclosure relate to systems, methods and compositions that can be implemented using any suitable RNA-guided nuclease having a certain PAM specificity and/or cleavage activity. For this reason, unless otherwise specified, the term RNA-guided nuclease should be understood as a generic term, and not limited to any particular type (e.g., Cas9 vs. Cpf1), species (e.g., *S. pyogenes* vs. *S. aureus*) or variation (e.g., full-length vs. truncated or split; naturally-occurring PAM specificity vs. engineered PAM specificity).

Various RNA-guided nucleases may require different sequential relationships between PAMs and protospacers. In general, Cas9s recognize PAM sequences that are 5' of the protospacer as visualized relative to the top or complementary strand. In addition to recognizing specific sequential orientations of PAMs and protospacers, RNA-guided nucleases generally recognize specific PAM sequences. *S. aureus* Cas9, for example, recognizes a PAM sequence of NNGRRT, wherein the N sequences are immediately 3' of the region recognized by the gRNA targeting domain. *S. pyogenes* Cas9 recognizes NGG PAM sequences. It should also be noted that engineered RNA-guided nucleases can have PAM specificities that differ from the PAM specificities of similar nucleases (such as the naturally occurring variant from which an RNA-guided nuclease is derived, or the naturally occurring variant having the greatest amino acid sequence homology to an engineered RNA-guided nuclease). Modified Cas9s that recognize alternate PAM sequences are described below.

RNA-guided nucleases are also characterized by their DNA cleavage activity: naturally-occurring RNA-guided nucleases typically form DSBs in target nucleic acids, but engineered variants have been produced that generate only SSBs (discussed above; see also Ran et al. Nature Protocols, 8(11): 2281-2308 (2013), incorporated by reference herein), or that do not cut at all.

RNA-guided nucleases include nickase variants, such as a Cas9 nickase. Various RNA-guided nickases or CRISPR nickases are known in the art, such as an *S. pyogenes* Cas9 with a D10A mutation. A dual-nickase approach may be employed, wherein two nicks on opposite strands of a sequence of interest that are offset by one or more nucleotides are introduced. When the two nicks are introduced, a double stranded break is created.

Accordingly, one of skill in the art would be able to select the appropriate nuclease for the present invention.

Guide RNA

As used herein, the term "guide RNA" or "gRNA" refer to any nucleic acid that promotes the specific association (or "targeting") of an RNA-guided nuclease such as a Cas9 to a target sequence (e.g., a genomic or episomal sequence) in a cell, which may be loaded into an artificial exosome of the disclosure as cargo.

As used herein, a "modular" or "dual RNA" guide comprises more than one, and typically two, separate RNA molecules, such as a CRISPR RNA (crRNA) and a trans-activating crRNA (tracrRNA), which are usually associated with one another, for example by duplexing. gRNAs and their component parts are described throughout the literature (see, e.g., Briner et al. Mol. Cell, 56(2), 333-339 (2014), which is incorporated by reference), which may be loaded into an artificial exosome of the disclosure as cargo.

As used herein, a "unimolecular gRNA," "chimeric gRNA," or "single guide RNA (sgRNA)" comprises a single RNA molecule, which may be loaded into an artificial exosome of the disclosure as cargo. The sgRNA may be a crRNA and tracrRNA linked together. For example, the 3' end of the crRNA may be linked to the 5' end of the tracrRNA. A crRNA and a tracrRNA may be joined into a single unimolecular or chimeric gRNA, for example, by means of a four nucleotide (e.g., GAAA) "tetraloop" or "linker" sequence bridging complementary regions of the crRNA (at its 3' end) and the tracrRNA (at its 5' end).

As used herein, a "repeat" sequence or region is a nucleotide sequence at or near the 3' end of the crRNA which is complementary to an anti-repeat sequence of a tracrRNA.

As used herein, an "anti-repeat" sequence or region is a nucleotide sequence at or near the 5' end of the tracrRNA which is complementary to the repeat sequence of a crRNA.

Additional details regarding guide RNA structure and function, including the gRNA/Cas9 complex for genome editing may be found in, at least, Mali et al. Science, 339(6121), 823-826 (2013); Jiang et al. Nat. Biotechnol. 31(3). 233-239 (2013); and Jinek et al. Science, 337(6096), 816-821 (2012); which are incorporated by reference herein.

As used herein, a "guide sequence" or "targeting sequence" refers to the nucleotide sequence of a gRNA, whether unimolecular or modular, that is fully or partially complementary to a target domain or target polynucleotide within a DNA sequence in the genome of a cell where editing is desired. Guide sequences are typically 10-30 nucleotides in length, e.g., 16-24 nucleotides in length (for example, 16, 17, 18, 19, 20, 21, 22, 23 or 24 nucleotides in length), and are at or near the 5' terminus of a Cas9 gRNA.

As used herein, a "target domain" or "target polynucleotide sequence" is the DNA sequence in a genome of a cell that is complementary to the guide sequence of the gRNA.

In addition to the targeting domains, gRNAs typically include a plurality of domains that influence the formation or activity of gRNA/Cas9 complexes. For example, as mentioned above, the duplexed structure formed by first and secondary complementarity domains of a gRNA (also referred to as a repeat: anti-repeat duplex) interacts with the recognition (REC) lobe of Cas9 and may mediate the formation of Cas9/gRNA complexes (Nishimasu et al. Cell 156: 935-949 (2014); Nishimasu et al. Cell 162(2), 1113-1126 (2015), both incorporated by reference herein). It should be noted that the first and/or second complementarity domains can contain one or more poly-A tracts, which can be recognized by RNA polymerases as a termination signal. The sequence of the first and second complementarity domains are, therefore, optionally modified to eliminate these tracts and promote the complete in vitro transcription of gRNAs, for example through the use of A-G swaps as described in Briner 2014, or A-U swaps. These and other similar modifications to the first and second complementarity domains are within the scope of the present disclosure.

Along with the first and second complementarity domains, Cas9 gRNAs typically include two or more additional duplexed regions that are necessary for nuclease activity in vivo but not necessarily in vitro (Nishimasu 2015, supra). A first stem-loop near the 3' portion of the second complementarity domain is referred to variously as the "proximal domain," "stem loop 1" (Nishimasu 2014, supra; Nishimasu 2015, supra) and the "nexus" (Briner 2014, supra). One or more additional stem loop structures are generally present near the 3' end of the gRNA, with the number varying by species: S. pyogenes gRNAs typically include two 3' stem loops (for a total of four stem loop structures including the repeat: anti-repeat duplex), while S. aureus and other species have only one (for a total of three). A description of conserved stem loop structures (and gRNA structures more generally) organized by species is provided in Briner 2014, which is incorporated herein by reference. Additional details regarding guide RNAs generally may be found in WO2018026976A1, which is incorporated herein by reference.

The RNA-guided nucleases may be combined with guide RNAs to form a gene editing complex. The RNA-guided nucleases may be combined with the guide RNAs to form a ribonucleoprotein (RNP) complex that may be loaded as cargo in the artificial exosomes of the disclosure for delivery to a cell where genome-editing is desired. The RNA-guided nucleases and guide RNAs may be expressed from one or more polynucleotides such as a vector. The RNA-guided nuclease may alternatively be expressed from a synthetic mRNA. In either case, the polynucleotide encoding the RNA-guided nucleases and/or guide RNAs may be loaded as cargo in the artificial exosomes of the disclosure for delivery to a cell where genome-editing is desired.

Small Molecule Cargo

As used herein, a "small molecule" or "small molecule drug" refers to a compound with a low molecular weight, often 1 kilodalton (KDa) or less, which may be loaded into an artificial exosome of the disclosure as cargo. Small molecules are generally not biological molecules such as polypeptides, large polysaccharides, or nucleic acids.

In certain embodiments, the small molecule is a chemotherapeutic agent. Chemotherapeutic agents useful for loading into the artificial exosomes of the disclosure include, but are not limited to, azacitidine, bendamustine, busulfan, cabazitaxel, capecitabine, carboplatin, carmustine, chlorambucil, cisplatin, cladribine, clofarabine, cytarabine, dacarbazine, dactinomycin, daunorubicin, docetaxel, doxorubicin, epirubicin, eribulin, etoposide, fludarabine, fluorouracil (5FU), gemcitabine, hydroxycarbamide, idarubicin, ifosfamide, irinotecan, leucovorin, lomustine, melphalan, mercaptopurine, mesna, methotrexate, mitomycin, mitotane, mitoxantrone, nab-paclitaxel, oxaliplatin, paclitaxel, pemetrexed, pentostatin, procarbazine, raltitrexed, streptozocin, temozolomide, thiotepa, tioguanine, topotecan, trabectedin, treosulfan, trifluridine-tipiracil hydrochloride, vinblastine, vincristine, vinorelbine, or any combination thereof.

Viral Cargo

The artificial exosomes of the disclosure may be loaded with a virus. In certain embodiments, the virus is an adenovirus. In certain embodiments, the virus is an adeno associated virus (AAV). Numerous AAV serotypes are known in the art and may be used as cargo for the artificial exosomes. In certain embodiments, the AAV is selected from AAV1, AAV2, AAV3, AAV4, AAV5, AAV6, AAV7, AAV8, AAV9, AAV10, and AAV11. In certain embodiments, the AAV is an engineered variant of an AAV. In an exemplary embodiment, the AAV is AAV9 or a variant thereof.

Fluorophore Cargo

The artificial exosomes of the disclosure may be loaded with a fluorophore. Exemplary fluorophores include, but are not limited to, long-chain dialkylcarbocyanines dyes and dialkylaminostyryl dyes, such as 1,1-dioctadecyl-3,3,3,3-tetramethylindotricarbocyanine iodide (DiR iodide), 1,1'-Dioctadecyl-3,3,3',3'-Tetramethylindocarbocyanine Perchlorate (DiI), 3,3'-Dioctadecyloxacarbocyanine Perchlorate (DiO or $DiOC_{18}(3)$), DiD, and DiR.

Delivery of Artificial Exosomes

Artificial exosomes of the disclosure may be used to deliver agents or cargo to cells. In one embodiment, artificial exosomes described herein may be used to deliver cargo to cells in culture. In another embodiment, artificial exosomes described herein may be used to deliver cargo to cells in a subject, e.g., a human. In some embodiments, artificial exosomes can be specifically targeted to a desired cell type or tissue type, e.g., damaged or diseased tissues. For example, artificial exosomes can be specifically targeted to a desired cell type or tissue type by attachment of a targeting peptide on the artificial exosome surface. The targeting peptide can bind to a moiety present on the surface of a desired target cell. For example, a specific cell-surface marker can be attached on the surface of the artificial exosome, which results in specific interaction with a receptor on a desired target tissue.

Suitable targeting peptides include those which bind to cell surface moieties, such as receptors or their ligands, found on the cell surface of the cell to be targeted.

Examples of suitable targeting moieties are short peptides, scFv and complete proteins, optionally with a targeting peptide attached on the surface of the artificial exosome. In some embodiments, targeting peptides are full-length proteins. In other embodiments, targeting peptides are fragments of full-length proteins. In some examples, targeting peptides are than 100 amino acids in length, for example less than 50 amino acids in length, less than 30 amino acids in length, to a minimum length of 10, 5 or 3 amino acids.

Targeting peptides can be selected to target particular tissue types such as muscle, brain, liver, pancreas and lung for example, or to target a diseased tissue such as a tumor. In a particular embodiment, the artificial exosomes are targeted to neuronal tissue, such as brain tissue. This can be achieved using a targeting peptide that interacts with a neuronal cell surface marker. Exemplary neuronal cell surface markers include, but are not limited to GM1, NeuN, and the like. Rabies virus glycoprotein peptides and the peptide portions of tetanus or cholera toxins can also be used in some embodiments to specifically target artificial exosomes to neurons.

Methods of Treatment with Artificial Exosomes

Artificial exosomes of the disclosure may be used therapeutically in subjects, e.g., humans. Artificial exosomes may be used therapeutically through the delivery of a therapeutic cargo. Suitable therapeutic cargo includes, but is not limited to, oligonucleotides, polypeptides, and small molecules. Therapeutic cargo can be used for the treatment or prevention of a disease or disorder in the subject.

Diseases and disorders of the present disclosure that may be treated with artificial exosomes include, but are not limited to, Crohn's disease, ulcerative colitis, rheumatoid arthritis, multiple sclerosis, systemic lupus erythematosus, sarcoidosis, idiopathic pulmonary fibrosis, psoriasis, tumor necrosis factor (TNF) receptor-associated periodic syndrome (TRAPS), deficiency of the interleukin-1 receptor antagonist (DIRA), endometriosis, autoimmune hepatitis, scleroderma, myositis, stroke, acute spinal cord injury, vasculitis, Guillain-Barre syndrome, acute myocardial infarction, ARDS, sepsis, meningitis, encephalitis, liver failure, kidney failure, graft-vs-host disease, Duchenne muscular dystrophy and other muscle diseases, neurodegenerative disease including Alzheimer's disease, Parkinson's disease, Huntington's disease, ALS, cancer-induced cachexia, anorexia, diabetes mellitus type 2, and cancers. According to certain embodiments, cancers that may be treated with artificial exosomes described herein include, but are not limited to, acute lymphoblastic leukemia (ALL), acute myeloid leukemia, adrenocortical carcinoma, AIDS-related cancers, AIDS-related lymphoma, anal cancer, appendix cancer, astrocytoma, cerebellar or cerebral, basal cell carcinoma, bile duct cancer, bladder cancer, bone tumor, brain stem glioma, brain cancer, brain tumor (cerebellar astrocytoma, cerebral astrocytoma/malignant glioma, ependymoma, medulloblastoma, supratentorial primitive neuroectodermal tumors, visual pathway and hypothalamic glioma), breast cancer, bronchial adenomas/carcinoids, Burkitt's lymphoma, carcinoid tumor (e.g., childhood, gastrointestinal), carcinoma of unknown primary, central nervous system lymphoma, cerebellar astrocytoma/malignant glioma, cervical cancer, chronic lymphocytic leukemia, chronic myelogenous leukemia, chronic myeloproliferative disorders, colon cancer, cutaneous T-cell lymphoma, desmoplastic small round cell tumor, endometrial cancer, ependymoma, esophageal cancer, extracranial germ cell tumor, extrahepatic bile duct cancer, eye cancer (e.g., intraocular melanoma, retinoblastoma), gallbladder cancer, gastric (e.g., stomach) cancer, gastrointestinal carcinoid tumor, gastrointestinal stromal tumor (GIST), germ cell tumor (e.g., extracranial, extragonadal, ovarian), gestational trophoblastic tumor, glioma (e.g., glioma of the brain stem, cerebral astrocytoma, visual pathway and hypothalamic glioma), gastric carcinoma, hairy cell leukemia, head and neck cancer, heart cancer, hepatocellular (liver) cancer, Hodgkin lymphoma, hypopharyngeal cancer, intraocular melanoma, islet cell carcinoma (e.g., endocrine, pancreas), Kaposi sarcoma, kidney cancer (renal cell cancer), laryngeal cancer, leukemias (e.g., acute lymphoblastic (also called acute lymphocytic leukemia), acute myeloid (also called acute myelogenous leukemia), chronic lymphocytic (also called chronic lymphocytic leukemia), chronic myelogenous (also called chronic myeloid leukemia), hairy cell leukemia), lip and oral cancer, cavity cancer, liposarcoma, liver cancer (Primary), lung cancer (e.g., non-small cell, small cell), lymphomas (e.g., AIDS-related lymphoma, Burkitt's lymphoma, cutaneous T-cell lymphoma, Hodgkin lymphoma, non-Hodgkin lymphoma, primary central nervous system lymphoma), medulloblastoma, merkel cell carcinoma, mesothelioma, metastatic squamous neck cancer with occult primary, mouth Cancer, multiple endocrine neoplasia syndrome, multiple myeloma/plasma cell neoplasm, mycosis fungoides, myelodysplastic/myeloproliferative diseases, myelogenous leukemia, chronic myeloid leukemia (e.g., acute, chronic), myeloma, nasal cavity and paranasal sinus cancer, nasopharyngeal carcinoma, neuroblastoma, oral cancer, oropharyngeal cancer, osteosarcoma/malignant fibrous histiocytoma of bone, ovarian cancer, ovarian epithelial cancer (Surface epithelial-stromal tumor), ovarian germ cell tumor, ovarian low malignant potential tumor, pancreatic cancer, pancreatic islet cell cancer, parathyroid cancer, penile cancer, pharyngeal cancer, pheochromocytoma, pineal astrocytoma, pineal germinoma, pineoblastoma and supratentorial primitive neuroectodermal tumors, pituitary adenoma, pleuropulmonary blastoma, prostate cancer, rectal cancer, renal cell carcinoma (kidney cancer), retinoblastoma, rhabdomyosarcoma, salivary gland cancer, sarcoma (e.g., Ewing family of tumors sarcoma, Kaposi sarcoma, soft tissue sarcoma, uterine sarcoma), Sezary syndrome, skin cancer (e.g., non-melanoma, melanoma), small intestine cancer, squamous cell, squamous neck cancer, stomach cancer, supratentorial primitive neuroectodermal tumor, testicular cancer, throat cancer, thymoma and thymic carcinoma, thyroid cancer, transitional cell cancer of the renal pelvis and ureter, urethral cancer, uterine cancer, uterine sarcoma, vaginal cancer, vulvar cancer, Waldenstrom macroglobulinemia, and/or Wilm's tumor (kidney cancer).

In exemplary embodiments, the disease or disorder is a neurological disease or disorder. Non-limiting examples of such disease or disorders include: acute disseminated encephalomyelitis, agnosia, Alpers' disease, Angelman syndrome, Asperger syndrome, Alzheimer's disease, amyotrophic lateral sclerosis, aneurysm, attention deficit hyperactivity disorder, autism, Bell's palsy, Batten disease, bipolar disorder, brain cancer, canavan disease, concussion, coma, cerebral hypoxia, cerebral palsy, Creutzfeldt-Jakob disease, dementia, depression, Dravet syndrome, dyslexia, epilepsy, encephalitis, Farber's disease, febrile seizures, Friedreich's ataxia, Gaucher disease, Huntinton's disease, hypersomnia, migraine, multiple sclerosis, narcolepsy, Parkinson's disease, schizophrenia, stroke, and traumatic brain injury, tremor, and Wallenberg's syndrome.

The artificial exosomes described herein can be administered to a subject by any suitable means. For example, appropriate routes of administration include parenteral, intramuscular, intracerebral, intravascular, subcutaneous, or transdermal. A physician will be able to determine the mode of administration appropriate for a given subject.

Artificial exosome administration may be by local or systemic administration. Local administration, depending on the tissue to be treated, may in some embodiments be achieved by direct administration to a tissue (e.g., direct injection, such as intratumoral injection, intramyocardial injection, or injection into neuronal cells or tissue). Local administration may also be achieved by, for example, lavage of a particular tissue (e.g., intra-intestinal or peritoneal lavage). In several embodiments, systemic administration is used and may be achieved by, for example, intravenous and/or intra-arterial delivery. In certain embodiments, intracoronary delivery is used.

In some embodiments, subcutaneous or transcutaneous delivery methods are used. Due to the relatively small size, artificial exosomes are particularly advantageous for certain types of therapy because they can pass through blood vessels down to the size of the microvasculature, thereby allowing for significant penetration into a tissue. In some embodiments, this allows for delivery of the artificial exosomes directly to central portion of the damaged or diseased tissue (e.g., to the central portion of a tumor or an area of infarcted cardiac tissue). In addition, in several embodiments, use of artificial exosomes is particularly advantageous because artificial exosomes can deliver their cargo (e.g., oligonucleotides, polypeptides, and/or small molecules) across the blood brain barrier, which has historically presented an obstacle to many central nervous system therapies. In certain embodiments, however, artificial exosomes may be delivered to the central nervous system by injection through the blood brain barrier.

In some embodiments, artificial exosomes are directly infused into the tissue of interest. For example, artificial exosomes can be directly infused into the brain, e.g., by intra-striatal injection. The artificial exosomes can delivered as a composition, e.g., a pharmaceutical composition, as described herein. The composition may be formulated for parenteral, intramuscular, intracerebral, intravascular (including intravenous), subcutaneous, or transdermal administration. Compositions for parenteral administration may include sterile aqueous solutions which may also contain buffers, diluents and other suitable additives. Artificial exosomes of the disclosure may be formulated in a pharmaceutical composition, which may include pharmaceutically acceptable carriers, thickeners, diluents, buffers, preservatives, and other pharmaceutically acceptable carriers or excipients and the like in addition to the artificial exosomes.

As used herein, a "pharmaceutically acceptable carrier" (excipient) is a pharmaceutically acceptable solvent, suspending agent or any other pharmacologically inert vehicle for delivering artificial exosomes to a subject. Typical pharmaceutically acceptable carriers include, but are not limited to: binding agents (e.g., pre-gelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrates (e.g., starch, sodium starch glycolate, etc.); wetting agents (e.g., sodium lauryl sulfate, etc.) and the like.

The compositions provided herein may additionally contain other adjunct components conventionally found in pharmaceutical compositions. Thus, for example, the compositions may contain additional compatible pharmaceutically-active materials or may contain additional materials useful in physically formulating various dosage forms of the composition of present invention, such as dyes, flavoring agents, preservatives, antioxidants, opacifiers, thickening agents and stabilizers. However, such materials, when added, should not unduly interfere with the biological activities of the components of the compositions provided herein.

In certain embodiments, one or more therapeutically effective doses of artificial exosomes are administered to subjects. A dose may be determined according to various parameters, especially according to the severity of the condition, age, and weight of the patient to be treated; the route of administration; and the required regimen. A physician will be able to determine the required route of administration and dosage for any particular patient using this disclosure as a guide. Optimum dosages may vary depending on the relative potency of individual constructs, and can generally be estimated based on EC50s found to be effective in vitro and in in vivo animal models.

The dose of artificial exosomes administered, depending on the embodiment, ranges from about $1.0 \times 10^5$ to about $1.0 \times 10^9$ artificial exosomes, including about $1.0 \times 10^5$ to about $1.0 \times 10^6$, about $1.0 \times 10^6$ to about $1.0 \times 10^7$, about $1.0 \times 10^7$ to about $5.0 \times 10^7$, about $5.0 \times 10^7$ to about $1.0 \times 10^8$, about $1.0 \times 10^8$ to about $2.0 \times 10^8$, about $2.0 \times 10^8$ to about $3.5 \times 10^8$, about $3.5 \times 10^8$ to about $5.0 \times 10^8$, about $5.0 \times 10^8$ to about $7.5 \times 10^8$, about $7.5 \times 10^8$ to about $1.0 \times 10^9$, and overlapping ranges thereof. In certain embodiments, the artificial exosome dose is administered on a per kilogram basis, for example, about $1.0 \times 10^4$ artificial exosomes/kg to about $1.0 \times 10^9$ artificial exosomes/kg. In additional embodiments, artificial exosomes are delivered in an amount based on the mass of the target tissue, for example about $1.0 \times 10^4$ artificial exosomes/gram of target tissue to about $1.0 \times 10^9$ artificial exosomes/gram of target tissue.

In certain embodiments, artificial exosomes are administered based on a ratio of the number of artificial exosomes to the number of cells in a particular target tissue, for example artificial exosome: target cell ratio ranging from about $10^9$:1 to about 1:1, including about $10^8$:1, about $10^7$:1, about $10^6$:1, about $10^5$:1, about $10^4$:1, about $10^3$:1, about $10^2$:1, about 10:1, and ratios in between these ratios. In additional embodiments, artificial exosomes are administered in an amount about 10-fold to an amount of about 1,000,000-fold greater than the number of cells in the target tissue, including about 50-fold, about 100-fold, about 500-fold, about 1000-fold, about 10,000-fold, about 100,000-fold, about 500,000-fold, about 750,000-fold, and amounts in between these amounts.

In certain embodiments, the dosage of artificial exosomes is from about 0.01 mg/kg to about 100 mg per kg of body weight. For example, a daily dose can range from about 0.1 to about 50 mg per kg, e.g., from about 0.1 mg/kg to about 10 mg/kg of body weight, according to the potency of the specific artificial exosome cargo, the age, weight and condition of the subject to be treated, the severity of the disease and the frequency and route of administration.

Different dosages of the artificial exosomes may be administered depending on whether administration is by intramuscular injection or systemic (intravenous or subcutaneous) injection. In an exemplary embodiment, a dose of a single intramuscular injection is in the range of about 5 to about 20 μg. In another exemplary embodiment, the dose of single or multiple systemic injections is in the range of about 10 to about 100 mg/kg of body weight.

In several embodiments, artificial exosomes are delivered in a single bolus dose. In some embodiments, however, multiple doses of artificial exosomes may be delivered. In certain embodiments, artificial exosomes can be infused (or otherwise delivered) at a specified rate over time. Due to artificial exosome and artificial exosome cargo clearance (and breakdown of any targeted molecule), the patient may have to be treated repeatedly, for example once or more daily, weekly, monthly or yearly. Persons of ordinary skill in the art can easily estimate repetition rates for dosing based on measured residence times and concentrations of the artificial exosome and artificial exosome cargo in bodily fluids or tissues.

Methods of Isolating and Enriching Exosomes

Artificial exosomes, enriched exosomes or natural-derived exosomes of the disclosure may be isolated, purified and/or quantitated from a sample containing a population of exosomes, such as, e.g., cell culture medium, a bodily fluid or mesenchymal stem cells. In certain embodiments, a method of purification comprises contacting the solution with one or more agents that binds to a polypeptide and/or lipid of a particular artificial exosome or naturally-derived exosome that one wishes to enrich and/or quantitate. In certain embodiments, a method of enriching and/or quantitating comprises contacting a sample with a rab7 binding agent. In certain embodiments, a method of enriching and/or quantitating comprises contacting a sample with a desmoplakin binding agent. In certain embodiments, a method of enriching and/or quantitating comprises contacting a sample with an AHSG binding agent. In certain embodiments, a method of enriching and/or quantitating comprises contacting a sample with a cardiolipin binding agent. In certain embodiments, a method of enriching and/or quantitating comprises contacting a sample with a combination of one or more of a rab7 binding agent, a desmoplakin binding agent, an AHSG binding agent, and a cardiolipin binding agent.

As used herein, a "binding agent" refers to a molecule that binds to a target of interest. In certain embodiments, the target may be a polypeptide or a lipid. In certain embodiments, the binding agent may be an antibody or fragment thereof. As used herein, the term "antibody" or "antigen binding protein" refers to an immunoglobulin molecule that specifically binds to, or is immunologically reactive with an antigen or epitope, and includes both polyclonal and monoclonal antibodies, as well as functional antibody fragments, including but not limited to fragment antigen-binding (Fab) fragments, F(ab')2 fragments, Fab' fragments, Fv fragments, recombinant IgG (rIgG) fragments, single chain variable fragments (scFv) and single domain antibodies (e.g., sdAb, sdFv, nanobody) fragments. The term "antibody" includes genetically engineered or otherwise modified forms of immunoglobulins, such as intrabodies, peptibodies, chimeric antibodies, fully human antibodies, humanized antibodies, heteroconjugate antibodies (e.g., bispecific antibodies, diabodies, triabodies, tetrabodies, tandem di-scFv, tandem tri-scFv) and the like. Unless otherwise stated, the term "antibody" should be understood to encompass functional antibody fragments thereof.

The binding agent may also comprise a natural ligand or a fragment thereof that binds to the target of interest.

The binding agent may be immobilized on a solid surface to facilitate isolation and enrichment of the artificial exosomes and naturally-derived exosomes of the disclosure.

Methods of Identifying Components of a Minimal/Artificial Exosome

Components, e.g., polypeptides and/or lipids, that may be used to produce an artificial exosome or a minimal exosome may be identified using screening methods disclosed herein. In certain embodiments, the method comprises subjecting a population of cells to a stress to produce a population of stress-induced exosomes. The stress-induced exosomes are then isolated from the cells and analyzed to determine their polypeptide and/or lipid content. The polypeptide and/or lipid content of the stress-induced exosomes are then compared to exosomes produced from the same cells that were not subjected to the same stress. Polypeptides and/or lipids that are upregulated in the stress-induced exosomes versus the non-stress-induced exosomes may be useful to produce artificial exosomes.

Without wishing to be bound by theory, the introduction of a stress factor (e.g., serum deprivation) into exosome-producing cells improves exosome activity by altering polypeptide and lipid composition. The polypeptides and lipids that are increased in the stress-induced exosomes may be incorporated into a liposome based composition to generate artificial exosomes of the disclosure. These artificial exosomes are validated for contribution to enhanced vesicle trafficking to target cells.

The stress applied to the cell population may be any cellular stress known in the art. Examples of cellular stress include, but are not limited to, serum deprivation, oxidation, hypoxia, heat shock, UV radiation, xenobiotic stress, infection (e.g., interferon (IFN) stress), and endoplasmic reticulum (ER) stress.

The method of analyzing the polypeptide and/or lipid content of the exosomes may be any proteomic and/or lipidomic method known in the art. Generally, specific polypeptides and lipids in the exosomes are identified by mass spectrometry.

Methods of Assaying Artificial Exosome Quality

The artificial exosomes of the disclosure may be assayed to measure quality. The quality of an artificial exosome may be based on the activity of the artificial exosome and/or the presence and/or abundance of certain polypeptides and/or lipids within the artificial exosome. In certain embodiments, activity may be determined by measuring the amount of cargo that is taken up by the artificial exosomes. In certain embodiments, activity may be determined by measuring the amount of cargo retained by the artificial exosomes after cargo loading. In certain embodiments, activity may be determined by measuring the amount of cargo delivered to a target cell by the artificial exosomes, e.g., the amount of cargo delivered to neuronal cells by the artificial exosomes. In certain embodiments, activity may be determined by measuring the effect of cargo delivered to a target cell by the artificial exosomes, e.g., measuring mRNA silencing mediated by an siRNA cargo delivered to neuronal cells by the artificial exosomes or measuring tumor cell killing mediated by a chemotherapeutic small molecule cargo delivered to the tumor cells by the artificial exosome. In certain embodiments, the presence and/or abundance of certain polypeptides within the artificial exosome may be measured by Western blot. In certain embodiments, the presence and/or abundance of certain polypeptides and/or lipids within the artificial exosome may be measured by immunofluorescence. In certain embodiments, the presence and/or abundance of certain polypeptides and/or lipids within the artificial exosome may be measured by mass spectrometry.

It will be readily apparent to those skilled in the art that other suitable modifications and adaptations of the methods described herein may be made using suitable equivalents without departing from the scope of the embodiments disclosed herein. Having now described certain embodiments in detail, the same will be more clearly understood by reference to the following examples, which are included for purposes of illustration only and are not intended to be limiting.

EXAMPLES

Example 1—Experimental Procedures

Oligonucleotides

The siRNAs used in this disclosure were synthesized using standard phosphoramidite chemistry as described previously (Alterman et al. Mol. Ther. Nucleic Acids 4, e266 (2015); Haraszti et al. Nucleic Acids Res. 45, 7581-7592 (2017); Nikan et al. Mol. Ther. Nucleic Acids 5, e344, (2016), incorporated herein by reference). siRNAs were conjugated to cholesterol at the 3' end of the passenger strand via a TEG linker, and were fully chemically modified with 5'-vinylphosphonate on the guide strand and an alternating pattern of 2'-O-methyls and 2'-fluoros on both strands (Haraszti, supra). PNA oligos were purchased from PNA Bio (PNA Bio, Newbury Park, Calif.).

Cell Culture

Umbilical cord, Wharton's jelly-derived mesenchymal stem cells (PCS-500-010, ATCC, Manassas, Va.), adipose tissue-derived mesenchymal stem cells (PCS-500-011, ATCC, Manassas, Va.), and bone marrow-derived mesenchymal stem cells (POETICS™, PT-2501, Lonza, Basel, Switzerland) were cultured in appropriate stem cell medium (PCS-500-030, ATCC, Manassas, Va., for umbilical cord and adipose tissue derived cells, and MSCGM™, PT-3238, Lonza, Basel, Switzerland for bone marrow derived cells) in the presence of supplements containing serum and growth factors (PCS-500-040, ATCC, Manassas, Va. and PT-3001, Lonza, Basel, Switzerland) at 37° C., 5% $CO_2$. Media was changed every three days, and cells were expanded until passage 12, to reach a total of 3000 $cm^2$ surface in T500 triple flasks. For serum deprivation, media was changed to RPMI (GIBCO™ RPMI 1640, Thermo Fisher Scientific) with no FBS or other supplements added for 24 hours.

Extracellular Vesicle (EV) Isolation and Characterization

Media on umbilical cord-derived mesenchymal stem cells was changed to extracellular vesicle (EV)-depleted medium (centrifuged at 100,000 g for at least 17 hours) or to RPMI (GIBCO™ RPMI 1640, Thermo Fisher Scientific) with no FBS or other supplements added and incubated for 24 hours. EVs were then isolated from this conditioned medium via differential ultracentrifugation as described previously (Didiot et al. Molecular Therapy, 24(10), 1836-1847, (2016)). Briefly, cell debris was pelleted at 300 g (10 min). Larger EVs or microvesicles were pelleted at 10,000 g (30 min), then supernatant filtered through a 0.2 μm membrane (Nalgene® aPES, Thermo Fisher Scientific, Waltham, Mass.) and small EVs or exosomes pelleted at 100,000 g (90 min) using 70 ml polycarbonate bottles (Beckman Coulter, Brea, Calif.; #355622) and Type 45 Ti rotor (Beckman Coulter, Brea, Calif.; #339160). Microvesicle and exosome pellets were then washed once in 1 ml sterile PBS and centrifuged again for 30 minutes at 10,000 g or for 90 minutes at 100,000 g, respectively.

For Western blot analyses, EVs or cell pellets were suspended in RIPA buffer (Pierce® 899000, Thermo Fisher Scientific, Waltham, Mass.) containing PMSF (36978, Thermo Fisher Scientific) and protease inhibitor cocktail (cOmplete Mini, 11836153001, Roche, Indianapolis, Ind.), and samples were sonicated for 15 minutes. Insoluble material was pelleted by centrifugation for 15 minutes at 10,000 g and 4° C. Proteins (50 μg) were loaded onto NuPAGE 4-12% Bis-Tris gels (Thermo Fisher Scientific, Waltham, Mass.). After transfer to PVDF (BioRad, Hercules, Calif.), membranes were incubated with antibodies, washed, and images captured using an Odyssey® system (Li-Cor, Bad Homburg, Germany) according to manufacturer's instructions. Primary antibodies used were Calnexin (C5C9, Cell Signaling, Danvers, Mass.), CD63 (115C6, BD BioSciences, San Jose, Calif.), Tsg101 (4A10, Abcam, Cambridge, Mass.), CD81 (B11, Santa Cruz Biotechnology, Dallas, Tex.), Desmoplakin (ab109445, Abcam, Cambridge, Mass.), AHSG (ab112528, Abcam, Cambridge, Mass.), and Rab7 (ab137029, Abcam, Cambridge, Mass.).

Concentration and size distribution of exosomes were measured by Nanoparticle Tracking Analysis (NanoSight NS300, Malvern). Briefly, samples were diluted in PBS 1:100 to 1:1000, manually injected into the instrument and videos acquired at ambient temperature at camera level 9 for 1 minute per sample, N=3. EVs were then frozen at −80° C. in 0.1 M sucrose and protease inhibitor cocktail (Sigma Aldrich, St. Louis, Mo., #P8340) until further use.

For large-scale exosome production, umbilical cord-derived mesenchymal stem cells were cultured in spinner flasks (250-ml) containing on Star-Plus Microcarriers (Solo-Hill®, Pall Life Sciences, Port Washington, N.Y.) in serum-free and xenofree StemPro® medium was added (A1067501, Life Technologies, Carlsbad, Calif.). Conditioned media was collected after 48 hours. Collection was performed four times, and conditioned media was stored at 4° C. and subsequently pooled together (final volume 1 L). The conditioned media was filtered through a 0.2 μm polyethersulfone (PES) membrane. Conditioned media was then subjected to ultrafiltration (9-fold concentration) in a tangential flow filtration system using a 500 kDa cutoff TFF cartridge (MidiKros® mPES 115 $cm^2$, D02-E500-05-S, Spectrum Labs, Rancho Dominguez, Calif.) and buffer exchanged with 6× volume of PBS. The exosomes were 0.2 µm filtered (PES membrane) and stored in 0.1 M sucrose at −80° C. until further use.

siRNA Loading to EVs and Liposomes

EVs were co-incubated with 10,000 copies of cholesterol-conjugated siRNA per vesicle at 37° C. for one hour in 500 µl PBS. The EV-siRNA mixture was then centrifuged at 100,000 g for 90 minutes (for exosomes) or at 10,000 g for 30 minutes (for microvesicles) and supernatant containing unloaded siRNA removed (supernatant). Pellet was taken up in 300 µl Neural Q medium for treatment of primary neurons and 100 µl PBS per mouse for mouse infusions. At this siRNA-to-EV concentration approximately 3000 siRNAs associate per vesicle. Liposomes and artificial exosomes were loaded identical to exosomes described above, e.g., post-synthesis.

Proteomics

Protein extraction followed the same protocol as for Western blotting. Total protein (50 µg) was applied to an SDS-PAGE gel. Once the entire protein sample entered the stacking gel, electrophoresis was stopped, and the portion of gel containing proteins was excised and stained with Coomassie brilliant blue. The fixed gel fragments were processed by University of Massachusetts Medical School Mass Spectrometry Core as described previously (Haraszti et al. J Extracell. Vesicles 5, 32570 (2016)). Briefly, proteins underwent in-gel trypsin digestion for 21 hours at 37° C., extracted from gels using 80:20 solution of acetonitrile: 1% formic acid, dried in a Speed Vac and pellets re-dissolved in 5% acetonitrile in 0.1% trifluroacetic acid. Digested protein aliquots were injected into a custom packed 2 cm×100 µm C18 Magic 5 µm particle trap column and samples sprayed on a Waters Nano Acquity UPLC system. Data dependent acquisitions were performed on a Q Exactive mass spectrometer (Thermo Fisher Scientific, Waltham, Mass.), full MS scans from 300-1750 m/z were acquired at a resolution of 70,000 followed by 10 MS/MS scans acquired under HCD fragmentation at a resolution of 17,500 and an isolation width of 1.6 Da. Raw data files were processed with Proteome Discoverer (version 1.4) before using Mascot Server (version 2.5) to search against the Uniprot_Human protein database. Applied search parameters were fully tryptic with 2 missed cleavages, parent mass tolerances of 10 ppm and fragment mass tolerances of 0.05 Da. Search results were loaded into the Scaffold Viewer (Proteome Software, Inc.) to quantify and analyze peptides.

Lipidomics

Frozen EV pellets were transferred to BERG LLC (Framingham, Mass.) on dry ice for lipid composition analysis as described before (Haraszti et al. J. Extracell. Vesicles, 5: 32570 (2016)). Briefly, aliquots of each sample were combined with a cocktail of deuterium-labeled and odd chain fatty acid standards. Standards were chosen that represent each lipid class and were at designated concentrations expected to provide the most accurate quantitation of each lipid species. Lipids were extracted with 4 mL of a 1:1 (v/v) solution of chloroform:methanol as previously described (Kiebish et al. J. Lipid Res. 51:2153-2170 (2010)), using an automated custom sequence routine on a Star Hamilton Robotics system (Hamilton, Reno, Nev.). Lipid extracts were dried under nitrogen and pellets were dissolved in 300 µl of a 1:1 (v/v) solution of chloroform: methanol per mg of protein. Samples were flushed with nitrogen and stored at −20° C.

For MS analysis, samples were diluted 50-fold in 3:3:3:1 (v/v/v/v) isopropanol:methanol:acetonitrile:water containing 2 mM ammonium acetate to enhance ionization efficiency in positive and negative modes. Electrospray ionization-MS was performed on a SCIEX TripleTOF® 5600' (SCIEX) coupled to a customized direct injection loop system on an Ekspert microLC200 system. 50 µl of sample was injected at a flowrate of 6 µl/min. Lipids were analyzed using a customized data independent analysis strategy on the TripleTOF® 5600+ allowing for MS/MS$^{ALL}$ high resolution and high mass accuracy analysis as previously described (Simon et al. Metabolites, 2: 195-213 (2012)). Lipids were quantified using an in-house library on MultiQuant™ software.

Liposome and Artificial Exosome Preparation

Conventional liposomes: Dioleoyl-phosphatidylcholine (DOPC) (#850375, Avanti Polar Lipids, Alabaster, Ala.) and cholesterol (#700000, Avanti Polar Lipids, Alabaster, Ala.) were diluted in chloroform at a concentration of 50 mg/ml. 35 µl of DOPC and 15 µl of cholesterol was transferred into a glass vial and chloroform was evaporated under argon flow. The resulting lipid film was rehydrated in 500 µl of PBS (#21-031-CV, Dulbecco's Phosphate Buffered Saline, Corning, Manassas, Va.), sonicated for 15 minutes in water bath (#BB5510, Branson ultrasonic cleaner 40 kHz, Cleanosonic, Richmond Va.), and the extruded using Mini-Extruder (#610000, Avanti Polar Lipids, Alabaster, Ala.) through a 50-nm pore sized polycarbonate membrane (#WHA800308, Whatman® Nucleopore™, MilliporeSigma, St Louis, Mo.). Liposomes were always used fresh, never frozen.

Cardiolipin containing liposomes: Cardiolipin (#840012, Avanti Polar Lipids, Alabaster, Ala.), monolysocardiolipin (#850081, Avanti Polar Lipids, Alabaster, Ala.) and dilysocardiolipin (#850082, Avanti Polar Lipids, Alabaster, Ala.) were diluted in chloroform at a concentration of 10 mg/ml. 20 µl DOPC, 15 µl cholesterol and 75 µl cardiolipin, or monolysocardiolipin or dilysocardiolipin were mixed together and liposomes prepared as for conventional liposomes above. This composition is equivalent to 40:30:30 w/w ratio of DOPC:cholesterol:cardiolipin/monolysocardiolipins/dilysocardiolipin.

Proteoliposomes: Purified proteins were purchased as follows: Rab7 (TP301776, OriGene, Rockville, Md.), AHSG (TP723089, OriGene, Rockville, Md.), Rab5 (TP303873, OriGene, Rockville, Md.), Desmocollin (TP322207, OriGene, Rockville, Md.), ARRDC1 (TP307160, OriGene, Rockville, Md.), Dermcidin (TP309352, OriGene, Rockville, Md.), Histone 1 (TP301249, OriGene, Rockville, Md.), Desmoplakin (RPU51172, Biomatik, Wilmington, Del.). Lyophilized proteins (AHSG and Desmoplakin) were dissolved in 0.1M sodium bicarbonate in PBS (pH=8.5). Proteins delivered in Tris-based buffers (Rab5, Desmocollin, ARRDC1, Dermcidin and Histone 1) underwent buffer exchange using 2K MWCO cutoff membrane dialysis devices (Slide-A-Lyzer™ Mini, #69553, Thermo Fisher Scientific, Waltham, Mass.) 10 µl of sample against 1 L of 0.1M sodium bicarbonate in PBS (pH=8.5) at 4° C. overnight. Palmitic acid N-hydroxysuccinimide ester (palmitoyl-NHS) (P1162, Sigma-Aldrich, St. Louis, Mo.) was added to protein samples in a 1:1 molar ratio to the amount of lysines (lysine frequency was estimated to be 7%) and incubated on a rotating wheel at 4° C. overnight. Palmitoyl-NHS-protein reaction mixture (equivalent of 1 µg protein) was then incubated with pre-formed conventional liposomes or dilysocardiolipin liposomes for 1 hour at 37° C. and proteoliposome samples centrifuged at 100,000 g for 70 minutes to remove non-loaded proteins. To prepare artificial exosomes, palmitoylated Rab7, AHSG and Desmoplakin were combined and loaded together to dilysocardiolipin liposomes.

Primary Neuron Culture

Primary cortical neurons were isolated from E15.5 mouse embryos of wild-type FVBNj mice. Pregnant females were anesthetized by intraperitoneal injection of Ketamine (100 mg/kg, KETASET®, Zoetis, Kalamazoo, Mich.)-Xylazine (10 mg/kg, AnaSed®, AKORN, Laker Forest, Ill., #NDC59399-111-50) followed by cervical dislocation. Embryos were removed and transferred to ice-cold DMEM/F12 medium (Invitrogen, Carlsbad, Calif.; #11320). Brains were removed and meninges were carefully detached. Cortices were isolated and transferred into pre-warmed papain solution for 25 minutes at 37° C., 5% $CO_2$ to dissolve the tissue. Papain (Worthington, Lakewood, N.J.; #54N15251) was dissolved in 2 ml Hibernate E (Brainbits, Springfield, Ill.; #HE) and supplemented with 0.25 ml of 10 mg/ml DNase 1 (Worthington, Lakewood, N.J.; #54M15168) in Hibernate E. After a 30-minute incubation, the papain solution was removed and 1 ml NeuralQ (Sigma-Aldrich, St. Louis, Mo., #N3100) supplemented with 2.5% FBS was added to the tissue. Tissues were then dissociated by trituration through a fire-polished, glass Pasteur pipet. Neurons were counted and diluted at $10^6$ cells/ml. $10^5$ neurons per well were plated on 96-well plates pre-coated with poly-L-lysine (BD BIOCOAT, Corning, N.Y.; #356515). After overnight incubation at 37° C., 5% $CO_2$, an equal volume of NeuralQ supplemented with anti-mitotics, 0.484 µl/ml of 5' UtP (Sigma, St Louis, Mo.; #U6625) and 0.2402 µl/ml of 5' FdU (Sigma, St Louis, Mo.; #F3503) was added to prevent the growth of non-neuronal cells. Half of the volume of media was replaced with fresh NeuralQ containing anti-mitotic every 48 hours until the experiments were performed. Neurons were treated with siRNA-loaded EVs or liposomes (resuspended in NeuralQ medium) and incubated for 7 days at 37° C., 5% $CO_2$ post-treatment.

Confocal Microscopy

For the analysis of siRNA-loaded exosome uptake in vitro, primary neurons were plated in poly-L-lysine (Sigma, St Louis, Mo.; #P4707) coated 35 mm glass bottom dishes (MatTek, Ashland, Mass., #P35G-1.5-10-C) were stained with NUCBLUE™ live cell stain (Thermo Fisher Scientific, Waltham, Mass., #R37605), and neurons were treated with exosomes containing fluorescently labeled siRNA targeting Huntingtin gene. Images were acquired with a Leica DM 1RE2 (Leica Microsystems Inc., Buffalo Grove, Ill.) confocal microscope using a 40× oil-immersion objective and DAPI channel (exposure time 50 ms) as well as mCherry channel (exposure time 200 ms). Images were processed using ImageJ software69 (NIH, Bethesda, Md.). The relative uptake of siRNA, loaded in control exosomes or stressed exosomes, was estimated based on pixel integrated density of 5 images for each timepoint, and normalized to the number of nuclei per image (nuclei counted manually).

Mouse Surgery

All animal procedures were approved by the University of Massachusetts Medical School Institutional Animal Care and Use Committee (IACUC, protocol number A-2411). ALZET® osmotic pumps (ALZET Osmotic Pump, Cupertino, Calif.; #1003D) were prefilled with 100 µl of sample following manufacturer instructions and primed overnight at 37° C. in a water bath. Osmotic pumps were loaded with either PBS (100 µl per pump), or $6.6×10^{10}$ vesicles loaded with cholesterol-siRNA (3000 copies per vesicle, total dose 0.33 nmol) (100 µl per pump), or equivalent amount of cholesterol-siRNA only (0.33 nmol, 100 µl per pump). Wild-type FVBNj mice were deeply anesthetized with 1.2% Avertin (Sigma, St Louis, Mo.; #T48402). ALZET® osmotic pumps were then placed using a stereotactic device (World Precision Instruments, Sarasota, Fla., #502610) into the right lateral ventricle (coordinates relative to bregma: 0.2 mm posterior, 0.8 mm lateral, 2.5 mm ventral). Pumps delivered their content for 3 days at 1 µl/hour rate. Mice were administered 4 mg/kg of meloxicam SR subcutaneously for pain management. Osmotic pumps were removed 5 days after infusion ended (8 days after placement) and wound closed with 7 mm wound clips. Animals were euthanized 4 weeks after pump placement using isoflurane overdose. Brains were cut in 300 µm thick coronal sections at 4° C. on a vibrotome, and 2 mm punches taken from striatum and motor cortex ipsilateral to the infusion. 3 punches were collected for mRNA quantification (immediately placed in RNAlater® (Thermo Fisher Scientific, Waltham, Mass., #AM7021), and 3 punches were collected for protein quantification (immediately frozen in liquid nitrogen).

Measurement of mRNA Levels

Primary neurons or brain punches were lysed in Quanti-Gene Lysis Mixture (part of QuantiGene Sample Processing Kit for cultured cells, Affymetrix, Thermo Fisher Scientific, Waltham, Mass., #QS0103) or QuantiGene Homogenizing solution (Affymetrix, Thermo Fisher Scientific, Waltham, Mass., #QG0517), respectively. mRNA quantification was performed using the QuantiGene 2.0 assay kit (Affymetrix, Thermo Fisher Scientific, Waltham, Mass., #QS0103) as described previously (Cole et al. Nucleic Acid Ther. 26: 86-92 (2016)). Catalog numbers for probes used in QuantiGene 2.0 assay were as follows: mouse Htt (Affymetrix, #SB-14150), mouse Hprt (Affymetrix, #SB-15463). Data sets were normalized to housekeeping gene Hprt.

Measurement of siRNA Levels siRNA guide strands in neuron cell lysates were quantified using a peptide-nucleic acid (PNA) hybridization assay. PNAs are oligonucleotides in which the sugar-phosphate backbone is replaced with a charge-neutral polyamide backbone. PNAs therefore have a high hybridization energy to RNA. SDS from leftover neuron lysates after mRNA quantification was precipitated with 3 M KCl and pelleted at 4,000 g for 15 minutes. siRNA guide strands in cleared supernatant were hybridized to fully complementary Cy3-labeled PNA strands (PNABio, Thousand Oaks, Calif.). siRNA guide strand-PNA duplexes were injected into HPLC DNAPac® PA100 anion exchange column (Thermo Scientific, Carlsbad, Calif.) and Cy3 fluorescence was monitored and peaks integrated. The mobile phase for HPLC was 50% water 50% acetonitrile, 25 mM Tris-HCl (pH 8.5), 1 mM EDTA and the salt gradient was 0 to 800 mM $NaClO_4$. For the calibration curve, a known amount of siRNA duplex was spiked into cell lysis solution.

Statistical Analysis siRNA uptake, mRNA silencing, cell viability, and lipidomics data were analyzed using GraphPad Prism 7, version 7.04 (GraphPad Software Inc., La Jolla, Calif.). In in vitro siRNA uptake experiments, curves were fitted using "exponential growth equation" (PNA hybridization assay data) or "one phase association" (confocal microscopy data). In in vitro silencing experiments, dose-response curves were fitted using "log(inhibitor) vs. response-variable slope (three parameters)" equation. Curves were compared using two-way ANOVA with Tukey multiple comparison for main column effect. In in vivo silencing experiments and cell viability assay groups were compared using one-way ANOVA with Tukey multiple comparison test. When comparing candidate proteins between control and stressed conditions, two-way ANOVA with multiple comparison for row effect according to the original FDR method of Benjamini and Hochberg. During lipidomics the amount of lipids were normalized to protein content of samples. Lipid classes in control versus stressed EVs or cells were compared using two-way ANOVA with Tukey multiple comparison for compare rows within columns. Fatty acid tail properties were correlated with enrichment score using linear regression.

Label-free quantification of proteins was performed via the iBAQ (intensity-based absolute quantification) method in Scaffold Viewer (Proteome Software Inc.) (see, Wilhelm et al. Nature 509:582-587 (2014)). Briefly, this method normalizes signal to the number of tryptic sites in a protein. Gene Ontology was performed using DAVID version 6.7 (NIH). Volcano plots and heatmaps were generated in $R^2$ using "ggplot2" and "pheatmap" packages. Differences in all comparisons were considered significant at p-values <0.05.

Figure 1B:
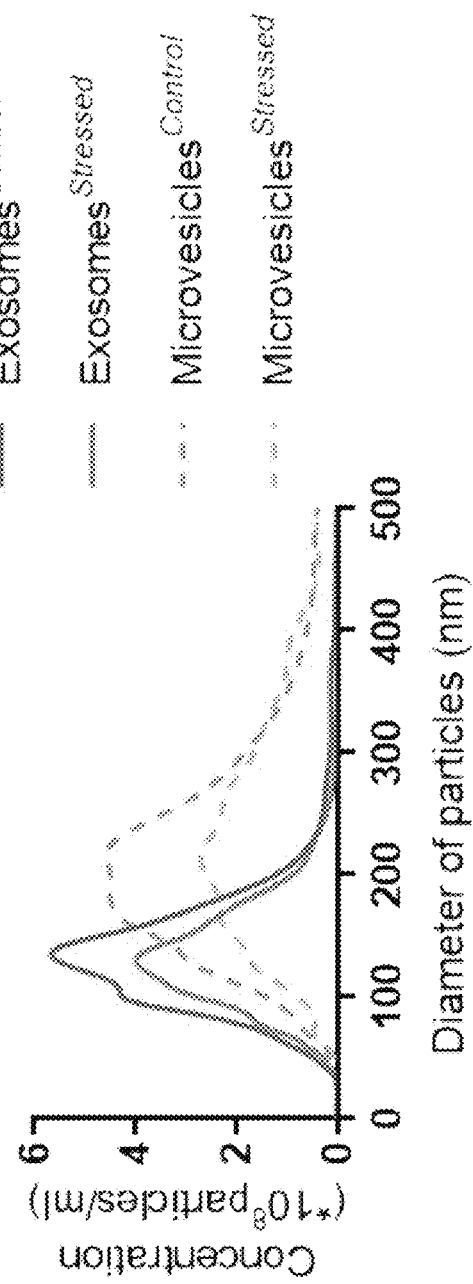
Figure 1C:
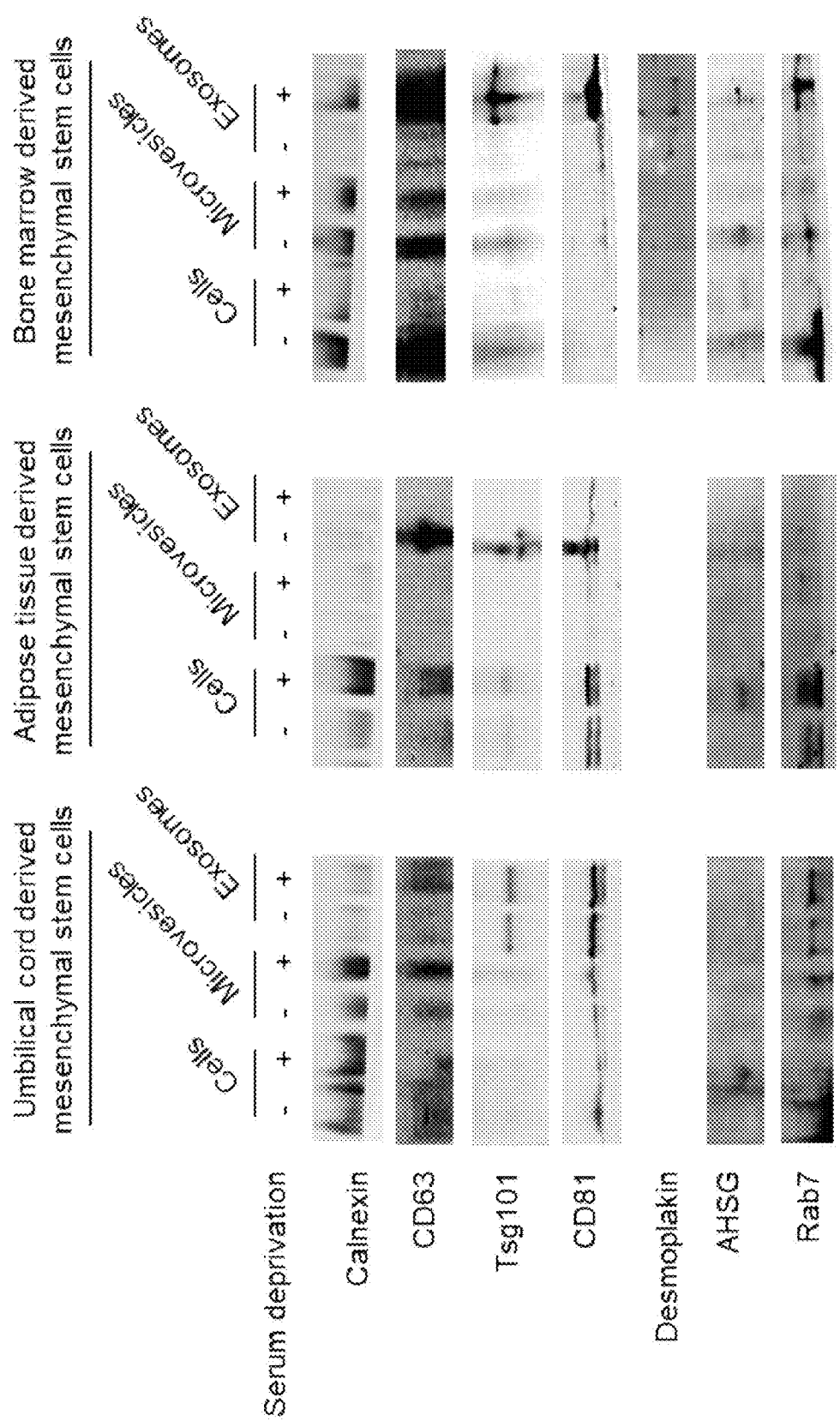
Figure 2A:
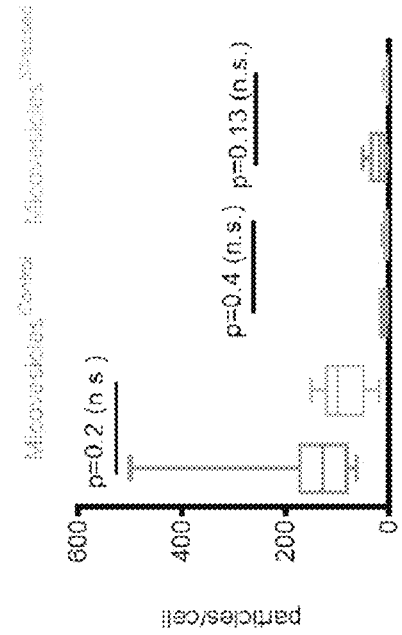
FIG. 2A-FIG. 2F depict the effect of serum deprivation of cells on yield and protein-to-vesicle ratio of extracellular vesicles.
Figure 2C:
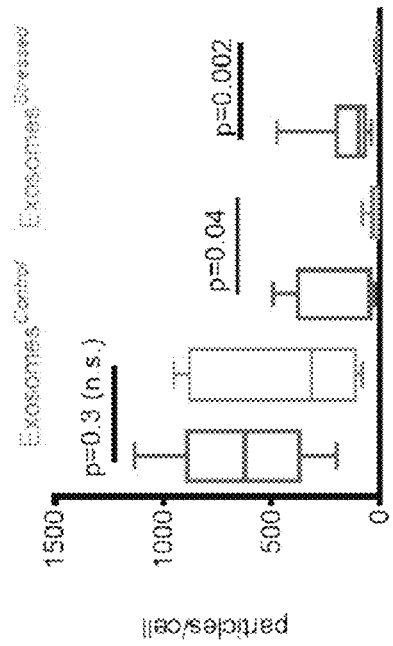
Figure 2B:
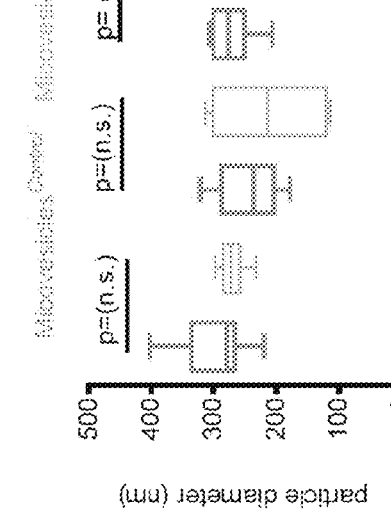
Figure 2D:
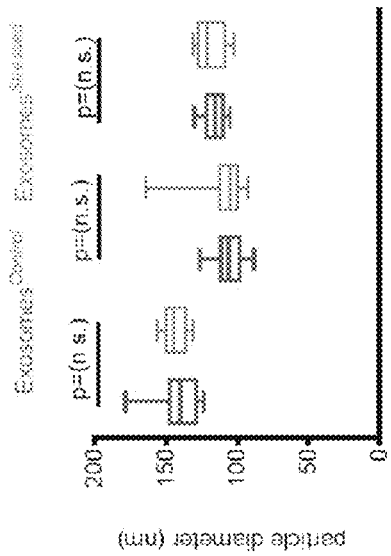
Figure 2F:
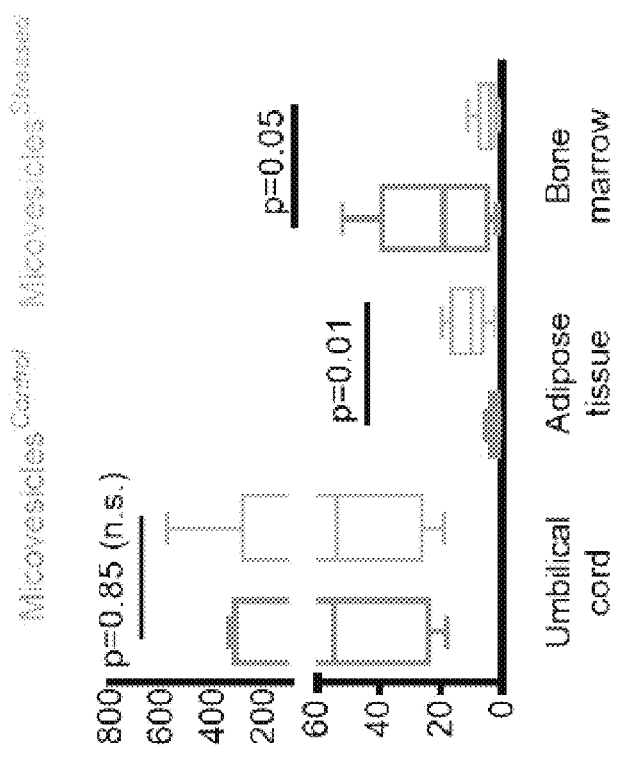
Figure 2E:
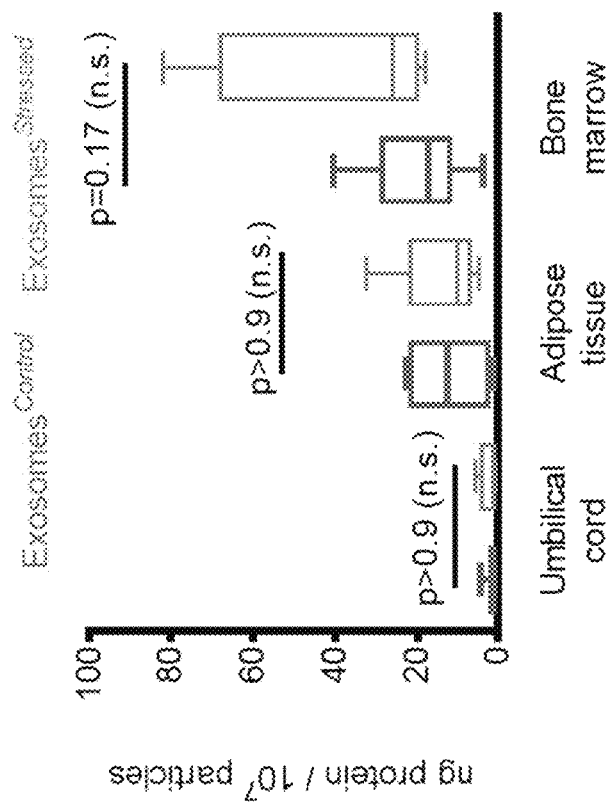

Example 2—Characterization of Extracellular Vesicles (EVs) Produced from Control and Serum-Deprived Mesenchymal Stem Cells Mesenchymal stem cells derived from umbilical cord, adipose tissue, and bone marrow were incubated in either the recommended stem cell medium depleted of EVs (control) or serum-free RPMI medium for 24 hours (stressed). Differential ultracentrifugation was used to generate two EV populations, small and large EVs, enriched based on their sedimentation properties (see, Thery et al. Curr. Protoc. Cell Biol. Chapter 3, Unit 3.22 (2006)). EVs from a 10,000×g pellet are referred to herein as microvesicles, and EVs from the 100,000 g pellet are referred to herein as exosomes. Stressed conditions were compared with control conditions within the same sample type throughout the examples: stressed cells versus control cells, microvesicles from stressed versus from control cells, and exosomes from stressed versus from control cells. Mesenchymal stem cells tolerated serum deprivation for up to 4 days (FIG. 1A) without loss of viability. EVs showed homogenous size distribution (FIG. 1B). Exosomes and microvesicles isolated from both the control or stressed (serum deprived for 24 hours) conditions displayed positive protein markers and were devoid of negative protein markers of EVs (FIG. 1C). Serum deprivation did not affect the exosome yield from umbilical cord-derived cells (p=0.3) but significantly decreased the exosome yield from both adipose- and bone marrow-derived cells (6-fold, p=0.04 and 10-fold, p=0.002 respectively, (FIG. 2A). Serum deprivation did not alter the amount of microvesicles (FIG. 2B). Exosomes derived from umbilical cord mesenchymal stem cells were slightly larger than exosomes from either adipose tissue or bone marrow cells (142±14 nm, 110±19 nm, and 117±10 nm, respectively). Serum deprivation did not affect EV size (FIG. 2C and FIG. 2D). Protein-to-particle ratio varied substantially between vesicles from different sources and was affected by serum deprivation for some EV populations (FIG. 2E and FIG. 2F). Umbilical cord-derived exosomes had the lowest protein-to-particle ratio, which remained unchanged upon serum deprivation (FIG. 2E and FIG. 2F).

Example 3—Serum-Deprived Mesenchymal Stem Cells Release Exosomes which are More Efficient in Delivery of siRNA Extracellular vesicles transport RNA between cells (Valadi et al. Nat. Cell Biol. 9: 654-659 (2007); Zomer et al. Cell 161: 1046-1057 (2015); Yang et al. Mol. Ther. Nucleic Acids 7: 278-287 (2017)). It has been previously shown that exosomes can productively transfer loaded cholesterol-conjugated siRNAs to neurons (Didiot et al. Molecular Therapy, 24(10), 1836-1847, (2016)). Here, Huntingtin-targeting, cholesterol-conjugated siRNAs (Alterman et al. Mol. Ther. Nucleic Acids 4, e266 (2015)) were loaded into exosomes and used to treat primary neurons as a model for exosome trafficking. The rates of exosome uptake to neurons were evaluated using confocal microscopy, and the level of guide strand accumulation and target mRNA silencing in neurons was quantified.

Figure 4A:
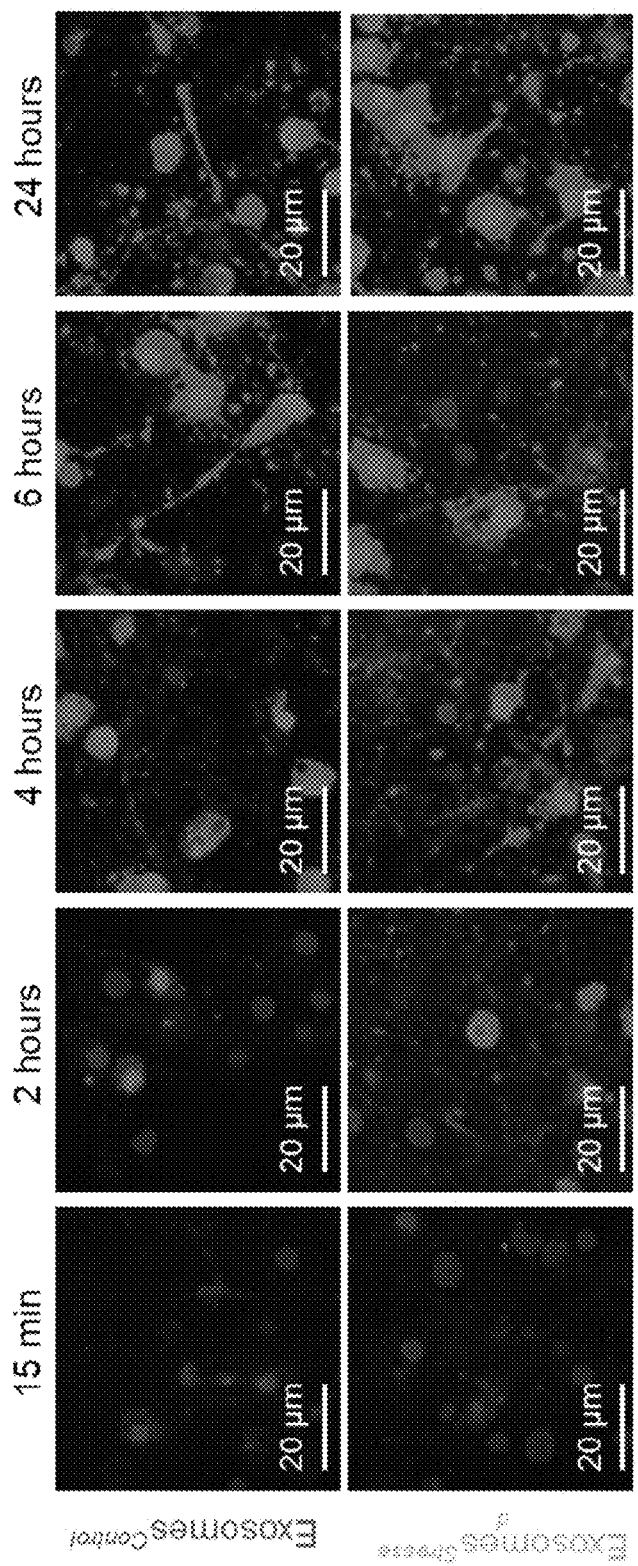
FIG. 4A-FIG. 4B depict neuronal uptake of control and stressed exosomes. Primary cortical neurons were cultures on glass bottom plates and treated with fluorescent siRNA containing stressed or control exosomes.
Figure 4B:
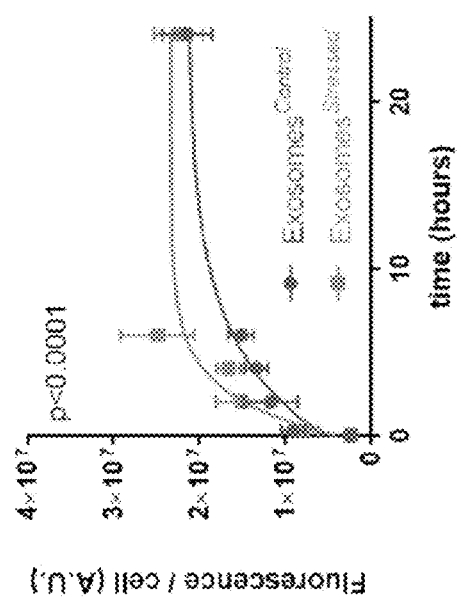

First, exosomes isolated from serum-deprived cells (stressed exosomes) delivered more siRNA to target neurons compared to control exosomes across all mesenchymal stem cell origins tested (FIG. 3A to FIG. 3C). Second, when loaded with fluorescently labeled siRNA, stressed exosomes showed an approximately two-fold faster neuronal uptake kinetic (half-time 1.7 versus 3.8 hours, p<0.0001) (FIG. 4A and FIG. 4B). Finally, siRNA-containing stressed exosomes were five- to twenty-two-fold more efficient at inducing Huntingtin mRNA silencing than control exosomes (FIG. 3D to FIG. 3D).

Interestingly, stress-dependent enhancement in activity was characteristic of exosomes and not of microvesicles, where serum deprivation impaired activity (FIG. 3G to FIG. 3I). These data indicated that activity enhancement upon stress depended on an exosome-specific characteristic.

Figure 5A:
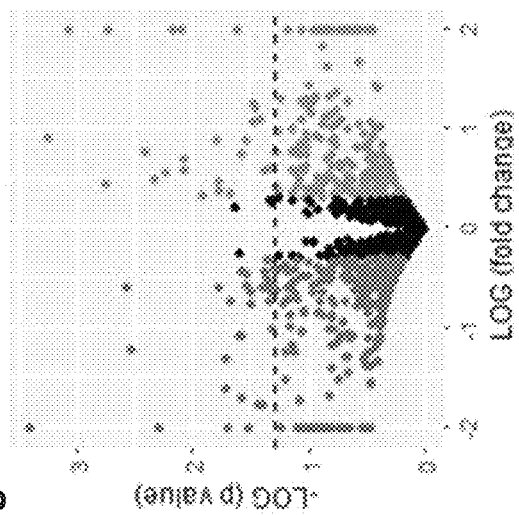
FIG. 5A-FIG. 5I depict the effect of serum deprivation of mesenchymal stem cells on protein content of exosomes, microvesicles, and cells. Exosomes, microvesicles and cells derived from control conditions or stress conditions (serum deprivation) underwent LC-MS/MS proteomics analysis. N=3 biological replicates were analyzed and label-free quantification carried out using intensity-based absolute quantification method.
Figure 5B:
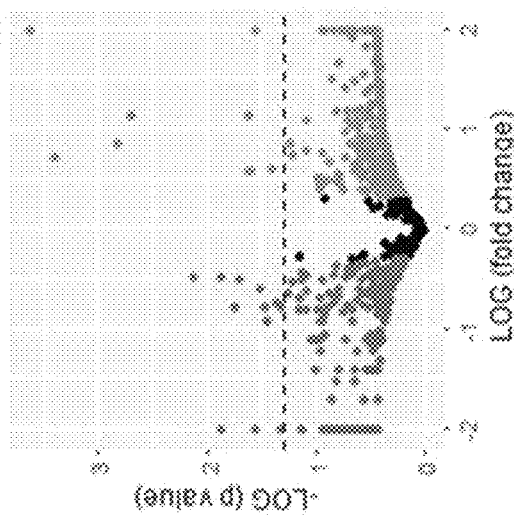
Figure 5C:
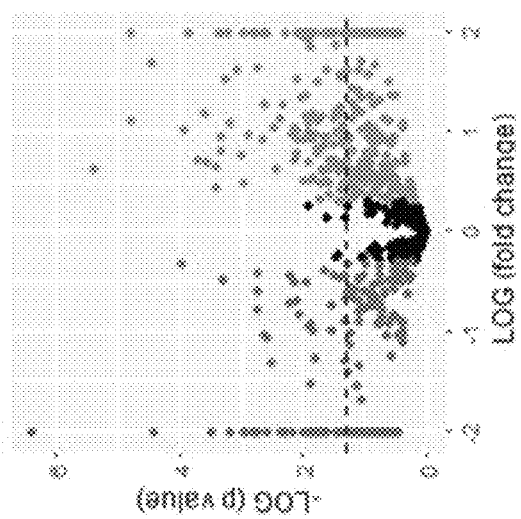
Figure 5D:
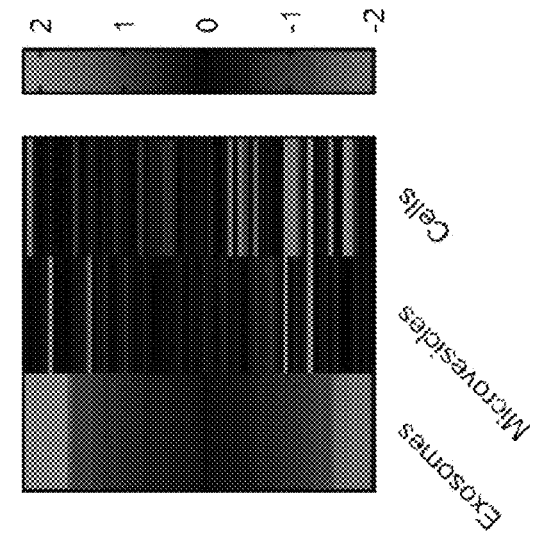
Figure 5E:
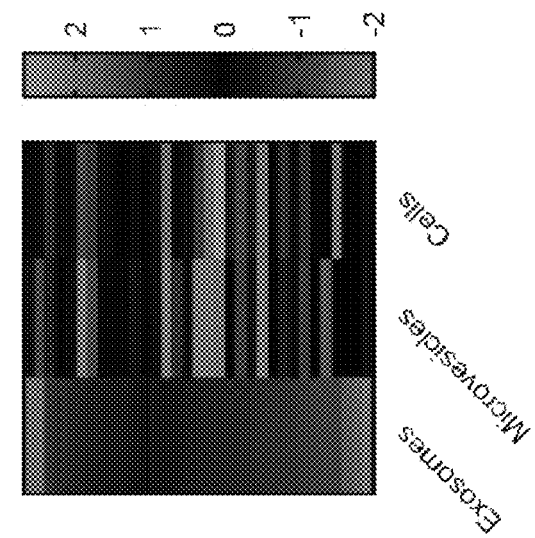
Figure 5F:
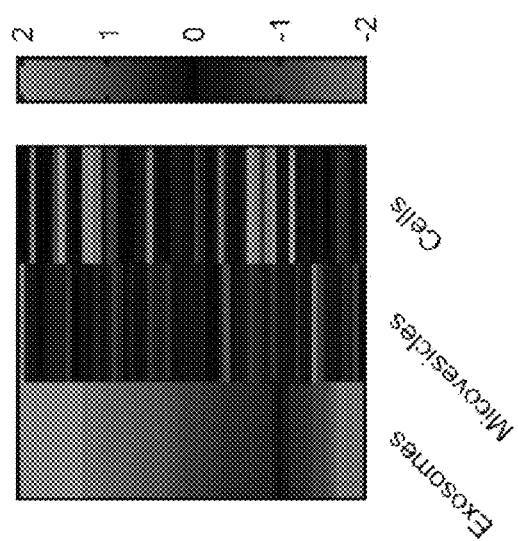

Example 4—Serum-Deprivation of Mesenchymal Stem Cells Alters Protein Composition of Exosomes Protein composition is one characteristic that differs between exosomes and microvesicles (Kowal et al. Proc. Natl. Acad. Sci. 113(8): E968-977 (2016); Haraszti et al. J Extracell. Vesicles 5, 32570 (2016)), and so it was investigated further. To evaluate serum deprivation-induced changes in the protein composition of exosomes, LC-MS/MS proteomic analysis was performed. Data was collected from three independent repeats of: (1) control or serum-deprived mesenchymal stem cells (derived from umbilical cord, adipose tissue, or bone marrow); (2) microvesicles from control or serum-deprived cells; and (3) exosomes from control or serum-deprived cells. The results show that serum deprivation had a profound effect on the proteome of cells, microvesicles, and exosomes, consistent in biological replicates (FIG. 5A to FIG. 5C). Protein composition differed substantially between exosomes and microvesicles. Proteins enriched in stressed exosomes were either unchanged or depleted in corresponding microvesicles and source cells (FIG. 5D to FIG. 5F).

Figures 5G, 5H, 5I:
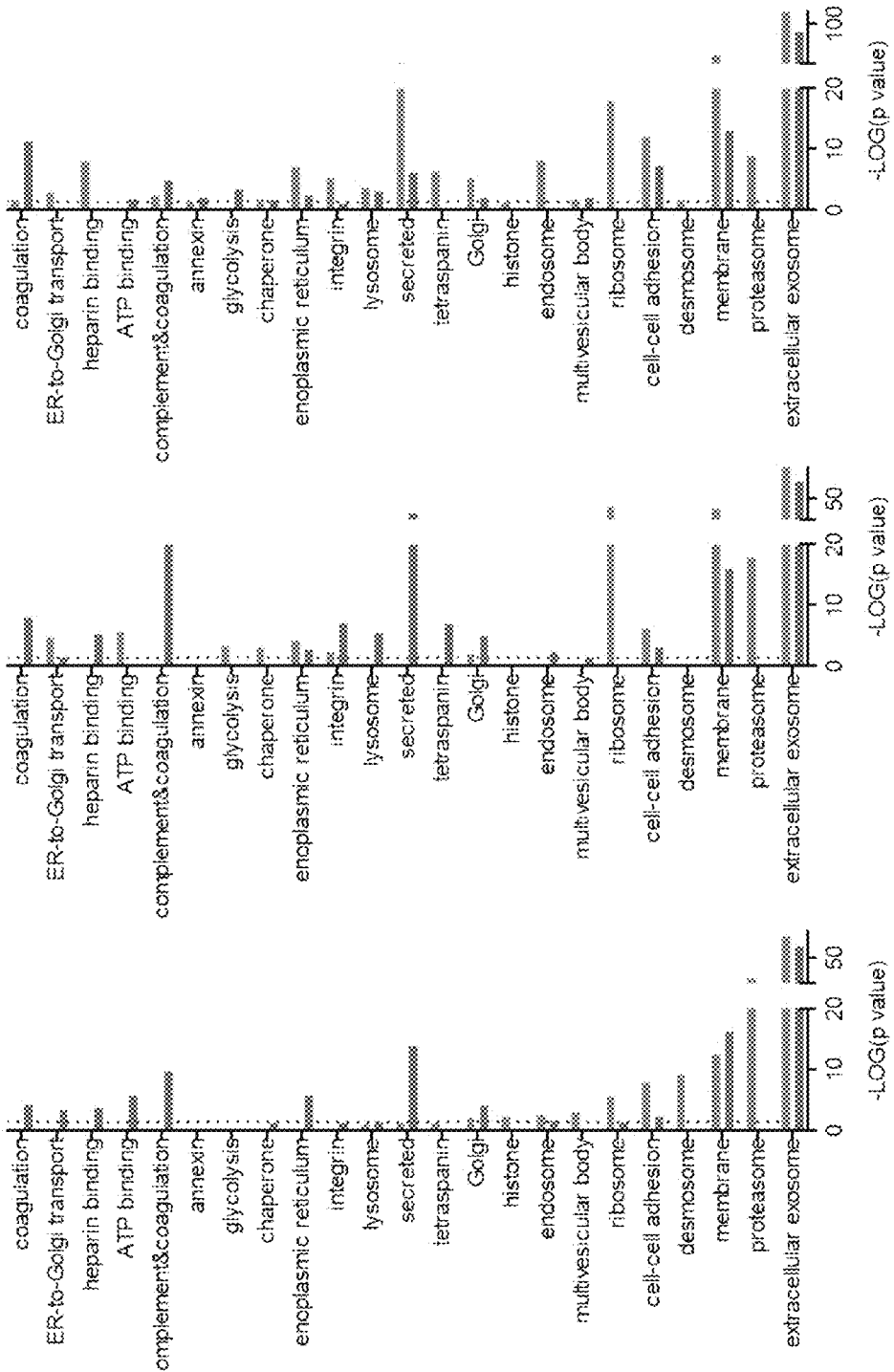

Gene Ontology analysis showed enrichment of extracellular exosome, proteasome, membrane, desmosome, cell-cell adhesion, ribosome, and Golgi proteins in stressed exosome fractions throughout all cell sources tested (FIG. 5G to FIG. 5I). In addition, multivesicular body, endosome, histone, tetraspanin, endoplasmic reticulum, ER-to-Golgi transport, and chaperone proteins were enriched in stressed exosomes derived from at least two of three cell sources tested (FIG. 5G to FIG. 5I).

Figure 6A:
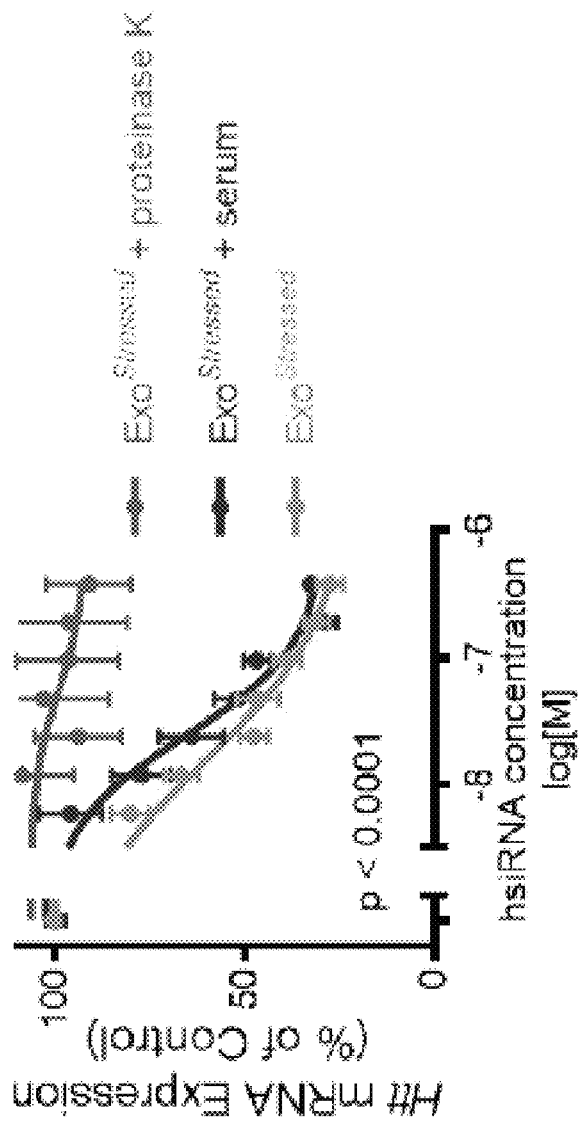
FIG. 6A-FIG. 6D depict the effect of proteins enriched in stressed exosomes in siRNA transfer to neurons. Exosomes were enriched from serum starved (FIG. 6A) or control (FIG. 6B) umbilical cord derived mesenchymal stem cells and either not further treated or treated with proteinase K or EV-depleted serum containing medium (serum). Primary neurons were then treated with the above exosome variants containing siRNAs and mRNA levels in neurons quantified after seven days of incubation. N=5, mean±SEM, curves compared using two-way ANOVA.
Figure 6B:
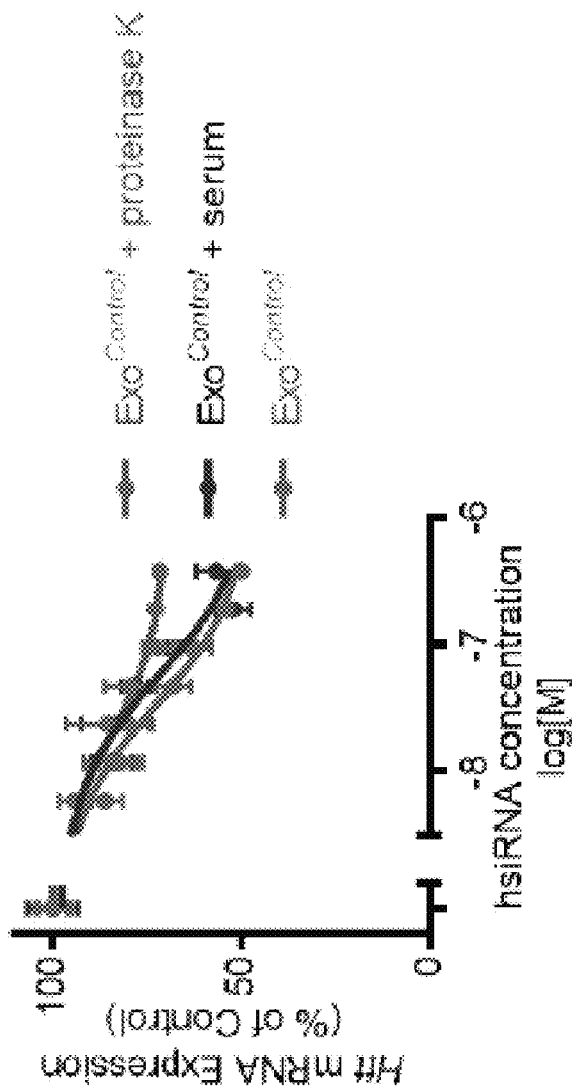

Example 5—Proteins Enriched in Stressed Exosomes Contribute to Improved siRNA Transfer to Neurons Without intending to be bound by scientific theory, altered surface protein composition can explain the enhanced activity of stressed exosomes. Proteinase K treatment (degrades surface proteins) impaired the exosome-mediated siRNA transfer and resulted in Huntingtin silencing (FIG. 6A and FIG. 6B), confirming that exosome surface proteins are essential for the delivery of cargo into neurons. The difference in the activity of stressed exosomes over control exosomes is not related to potential inhibition by serum proteins present, as incubation with serum-containing (EV-depleted) media had no effect on stressed exosome activity (FIG. 6A).

Figure 6D:
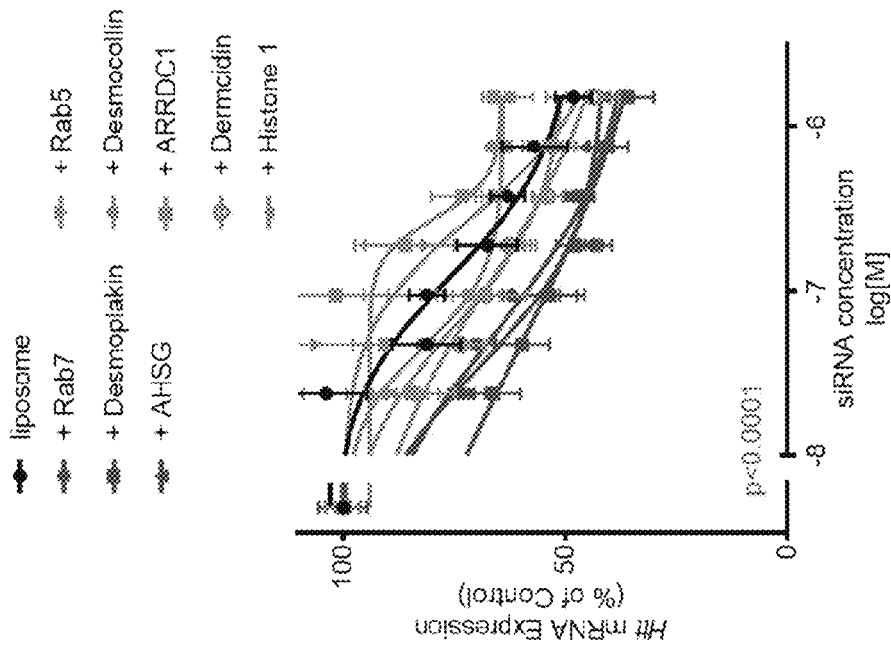
Figure 6C:
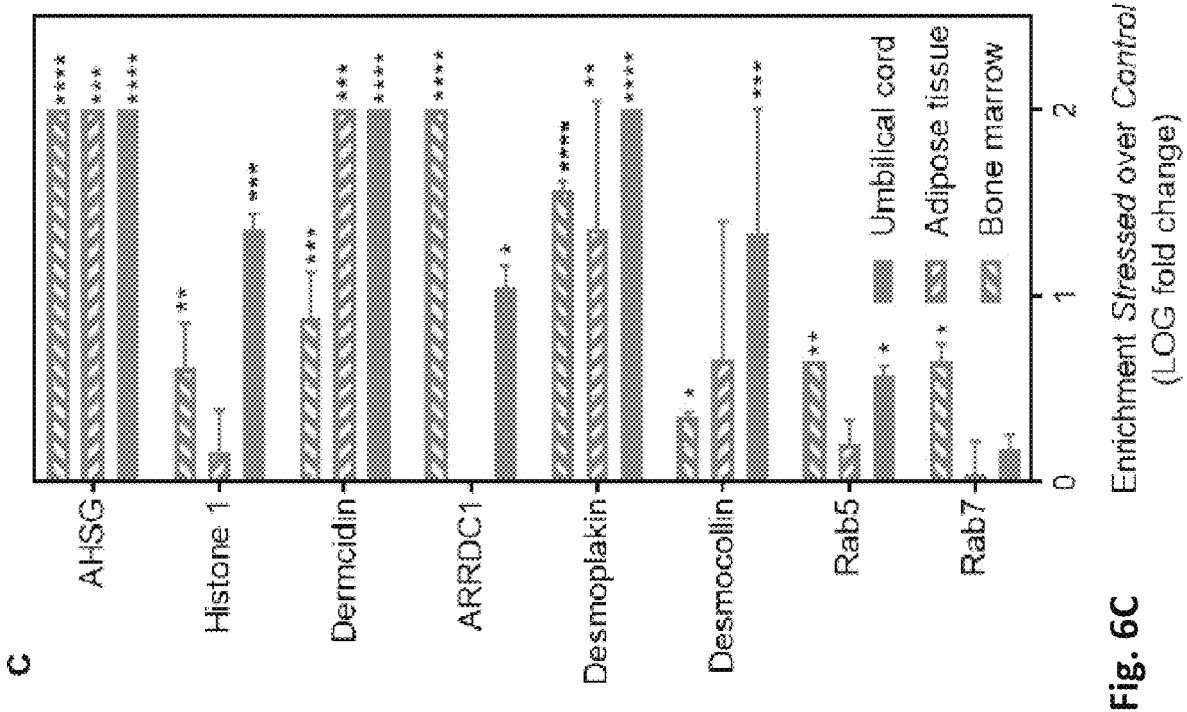

To establish a protein composition-activity relationship in exosomes, proteins were selected that (1) have an established role in vesicle trafficking or membrane adhesion, and (2) were enriched in stressed exosomes derived from at least two of three mesenchymal stem cell sources. Based on these criteria, the shortlist included proteins from endosomal pathways (Rab5 and Rab7) (Kummel et al. Curr. Opin. Cell Biol. 29: 61-66 (2014)), plasma membrane budding (ARRDC1) (Nabhan et al. Proc. Natl. Acad. Sci. 109: 4146-4151 (2012)), secreted proteins interacting with membranes (dermcidin) (Paulmann et al. J. Biol. Chem. 287: 8434-8443 (2012)), desmosome (Desmocollin, Desmoplakin) (Delva et al. Cold Spring Harb. Perspect. Biol. 1: a002543 (2009)), and nucleo-extracellular shuttles (AHSG and Histone 1) (Watson et al. FEBS Lett. 586: 3458-3463 (2012)) (FIG. 6C). AHSG has been reported to shuttle histones from the nucleus to exosomes (Watson, supra) and was consistently enriched in stressed cells (not present in EVs) (FIG. 6C), whereas histones were specifically enriched in stressed exosomes (FIG. 5G to FIG. 5I, FIG. 6C). The enrichment of Desmoplakin and Rab7 in stressed exosomes and AHSG in stressed cells was independently confirmed on Western blots FIG. 1C).

Purified proteins were chemically palmitoylated and co-incubated with neutral liposomes (dioleoyl-phosphatidyl-choline:cholesterol, 7:3) in order associate to the liposome surface. Palmitoylation has been reported as a strategy to enrich proteins associated to exosomal membranes (Lai et al. Nat. Commun. 6: 7029 (2015)). Incorporation of Rab7, desmoplakin, and AHSG improved liposome-mediated siRNA transfer to neurons and improved Huntingtin mRNA silencing (p<0.0001 two-way ANOVA, FIG. 6D). Incorporation of Rab5, desmocollin, ARRDC1, dermcidin, and histone 1 had no effect (FIG. 6D). Thus, incorporation of at least three candidate proteins from the proteomic analysis to the liposome surface affected the efficiency of vesicle transfer to neurons.

Figures 7A, 7B, 7C, 7D:
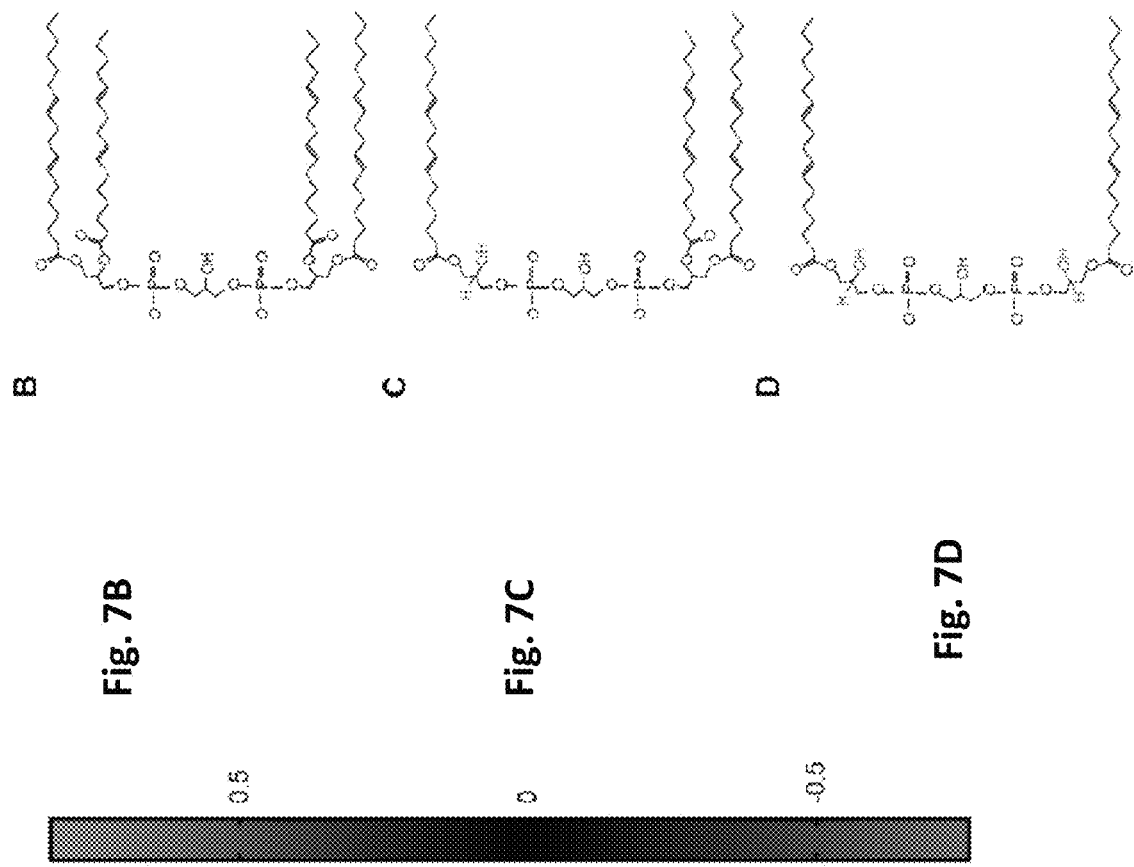
FIG. 7A-FIG. 7F depict the effect of dilysocardiolipin enrichment in stressed exosomes in siRNA for improved trafficking to neurons. Exosomes purified from umbilical cord derived mesenchymal stem cells under control or stress conditions (serum deprivation) underwent MS/MS$^{ALL}$ lipidomics analysis. N=2-5 biological replicates were analyzed per group.
Figure 8A:
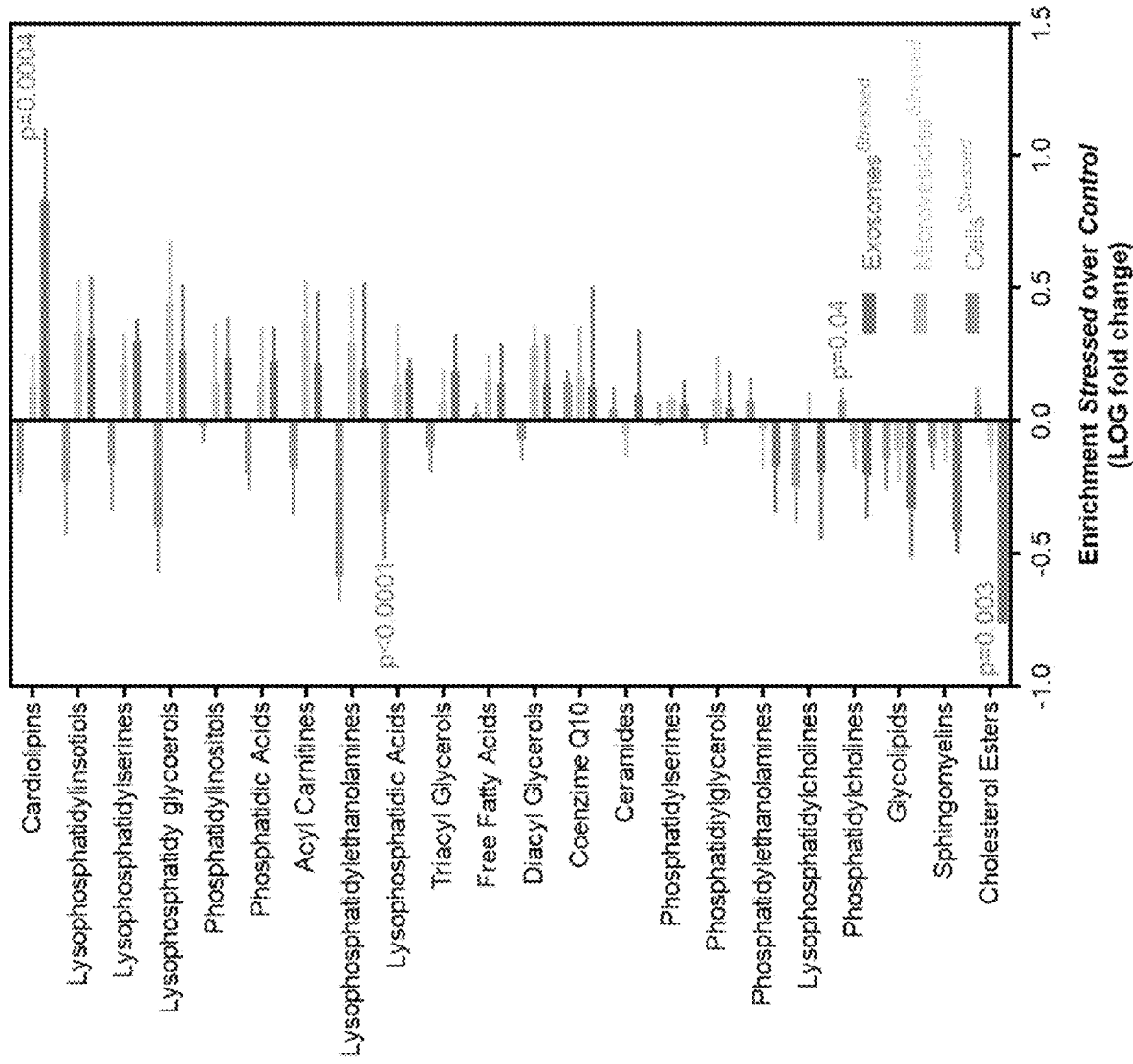
FIG. 8A depicts fluorescence microscopy images. Red: siRNA, Blue: nuclei. The siRNA signal was quantified (FIG. 8B).
Figure 8B:
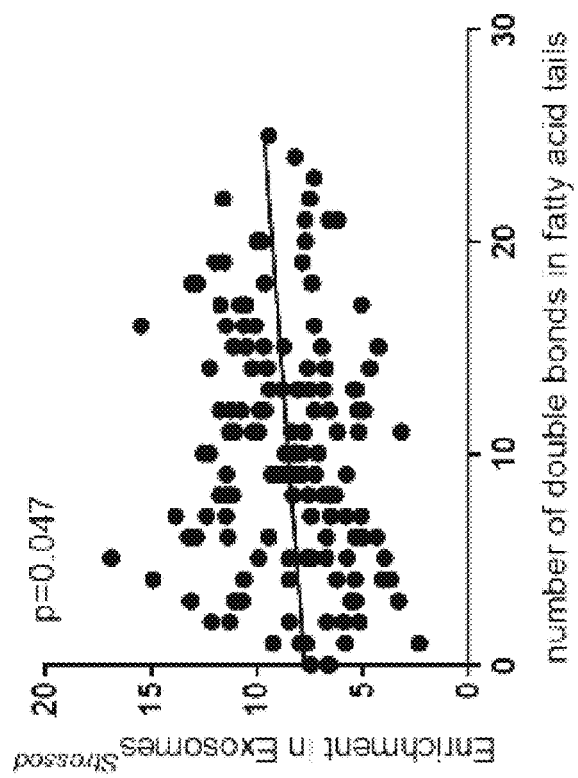
Figure 8C:
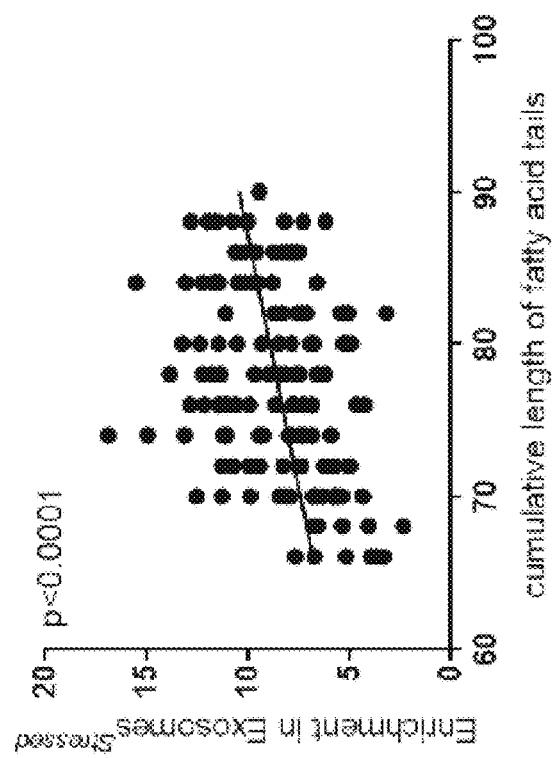

Example 6—Dilysocardiolipin Enrichment in Stressed Exosomes Contributes to Improved Trafficking to Neurons Without intending to be bound by scientific theory, membrane composition is a likely contributor to the enhanced trafficking activity of stressed exosomes. Membrane trafficking is regulated by both proteins and lipids (Ikonen et al. Curr. Opin. Cell Biol. 13: 470-477 (2001); Huijbregts, et al. Traffic 1: 195-202 (2000)). To evaluate the effect of serum deprivation on the lipid composition of exosomes, MS/MS$^{ALL}$ lipidomic analysis was performed. Among all lipid classes detected, only cardiolipins showed significant enrichment in exosomes derived from serum-deprived cells (p=0.004, two-way ANOVA) (FIG. 7A). Similar to protein enrichment, cardiolipin enrichment was specific to stressed exosomes and did not occur in corresponding cells and microvesicles (FIG. 7A and FIG. 8A). In addition, a modest but statistically significant enrichment in unsaturated and long-tailed cardiolipins in stressed exosomes was observed (FIG. 8B and FIG. 8C).

Cardiolipin is a diphosphatidylglycerol lipid with four fatty acid tails (FIG. 7B). Hydrolytic removal of one or two fatty acid tails results in the formation of monolysocardiolipin (FIG. 7C) or dilysocardiolipin (FIG. 7D), known intermediates in cardiolipin remodeling (Cao et al. J. Biol. Chem. 279: 31727-31734 (2004)). Cardiolipin remodeling has been associated with highly curved membranes (Schlame et al. Nat. Chem. Biol. 8: 862-869 (2012)).

Figures 7E, 7F:
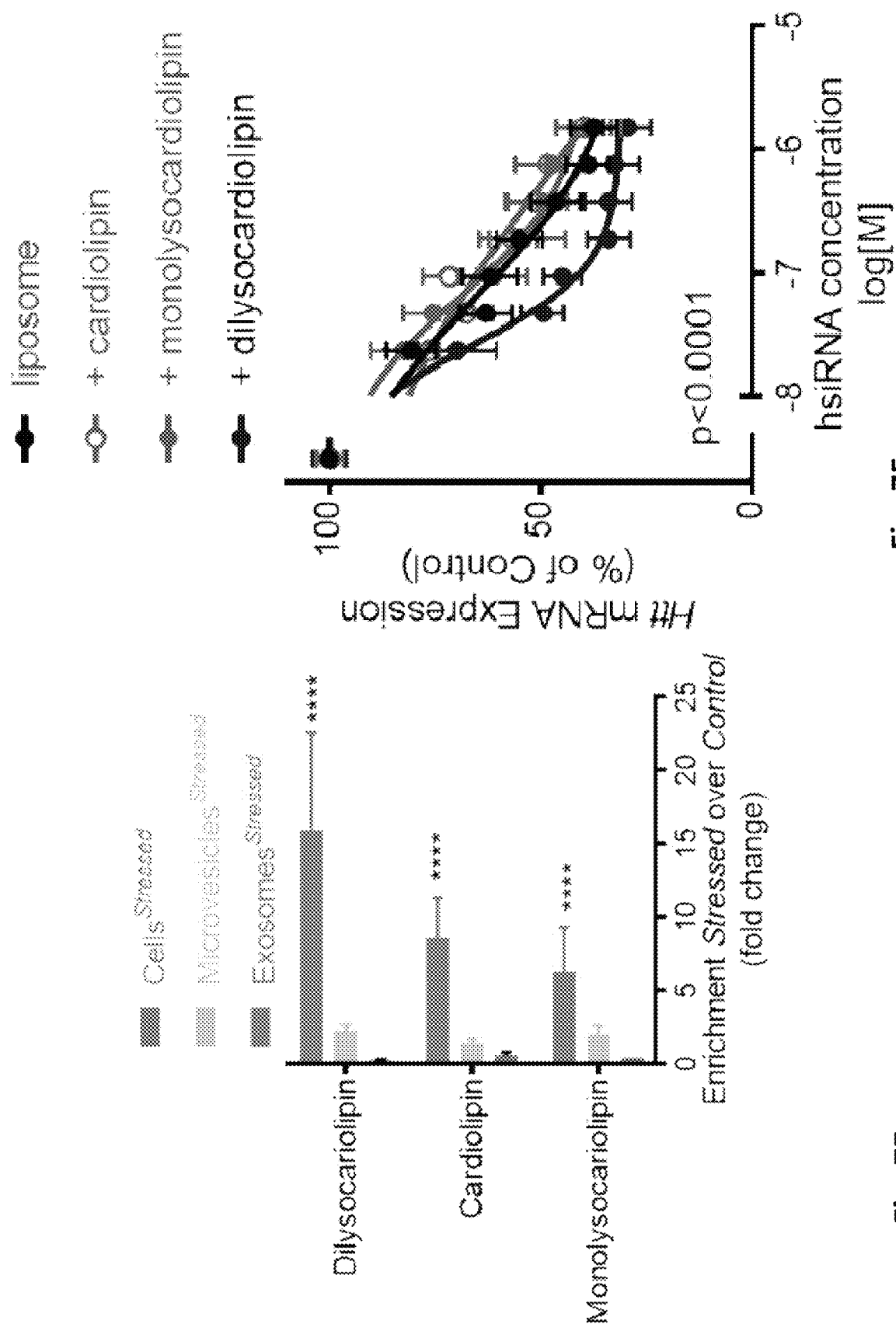

Among different cardiolipin subclasses, dilysocardiolipins showed the highest enrichment in stressed exosomes (sixteen-fold, p<0.0001), followed by intact cardiolipins (nine-fold, p<0.0001), and monolysocardiolipins (six-fold, p<0.0001) (FIG. 7E), compared to control exosomes. Cardiolipin subclass enrichment was specific to stressed exosomes and was not observed in corresponding microvesicles and cells (FIG. 7E).

To test whether cardiolipins play a role in vesicle trafficking to neurons, intact cardiolipin, monolysocardiolipin, or dilysocardiolipin was incorporated (30% of total lipid amount) in conventional liposomes (dioleoyl-phosphatidyl-choline, cholesterol). Incorporation of dilysocardiolipin, but not other variants, into liposomes improved siRNA transfer to neurons and resulted in Huntingtin silencing (p=0.007, two-way ANOVA) (FIG. 7F). Thus, dilysocardiolipin enrichment in stressed exosomes can be a contributing factor to enhanced neuronal uptake.

Example 7—Artificial Exosomes are Active at siRNA Delivery In Vitro and In Vivo

Figure 9B:
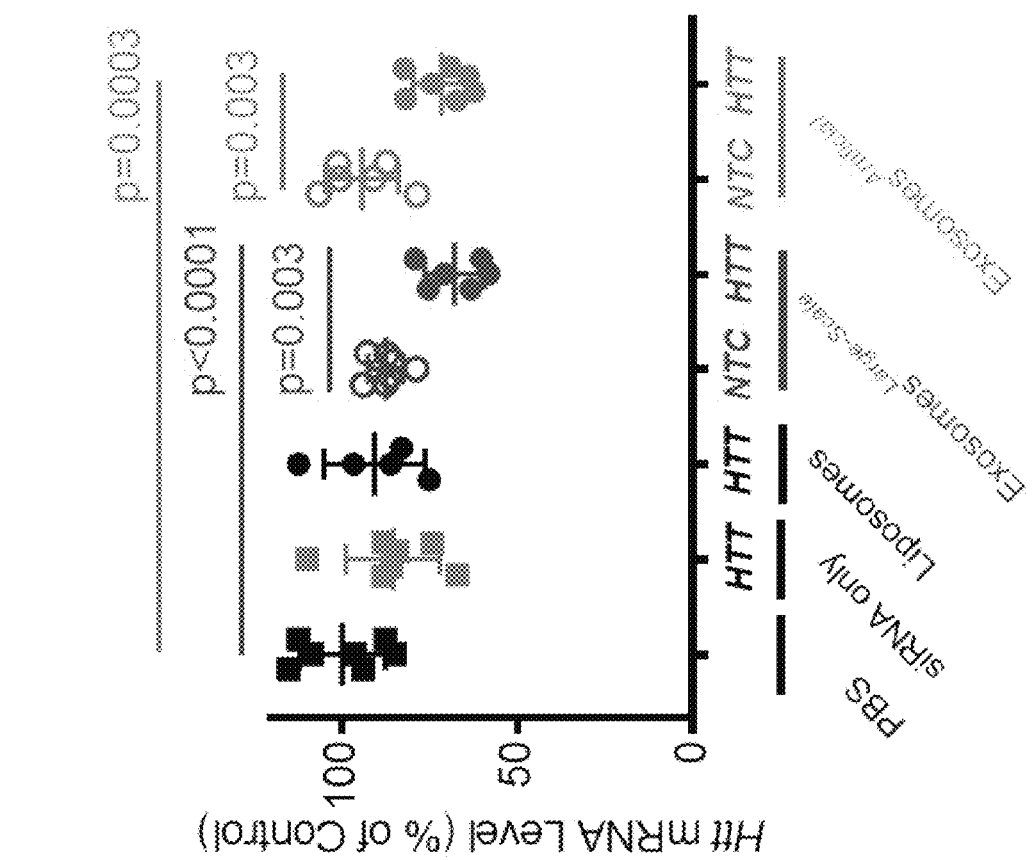
FIG. 9A-FIG. 9D depict the activity of artificial exosomes.
Figure 9A:
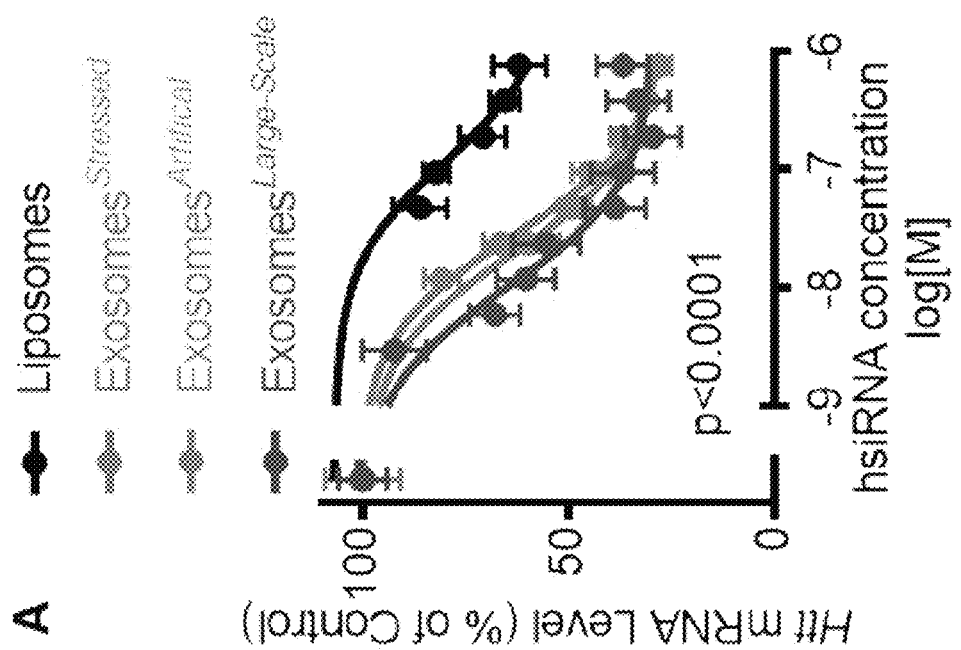

Having identified three proteins and one lipid class to be enriched in stressed exosomes and thereby improve vesicle uptake into neurons, the concept of engineering an artificial exosome displaying similar activity to that of stressed exosomes was explored. Common liposome components (dioleoylphosphatidylcholine and cholesterol) were combined with dilysocardiolipin and palmitoylated Rab7, Desmoplakin, and AHSG in a proteoliposome (i.e., an artificial exosome). Incorporation of three proteins and one lipid in liposomes significantly improved liposome-mediated siRNA transfer to neurons (p<0.0001, two-way ANOVA) (FIG. 9A). The efficiency of siRNA-containing artificial exosomes in Huntingtin silencing was indistinguishable from that of stressed exosomes (FIG. 9A).

Figure 9C:
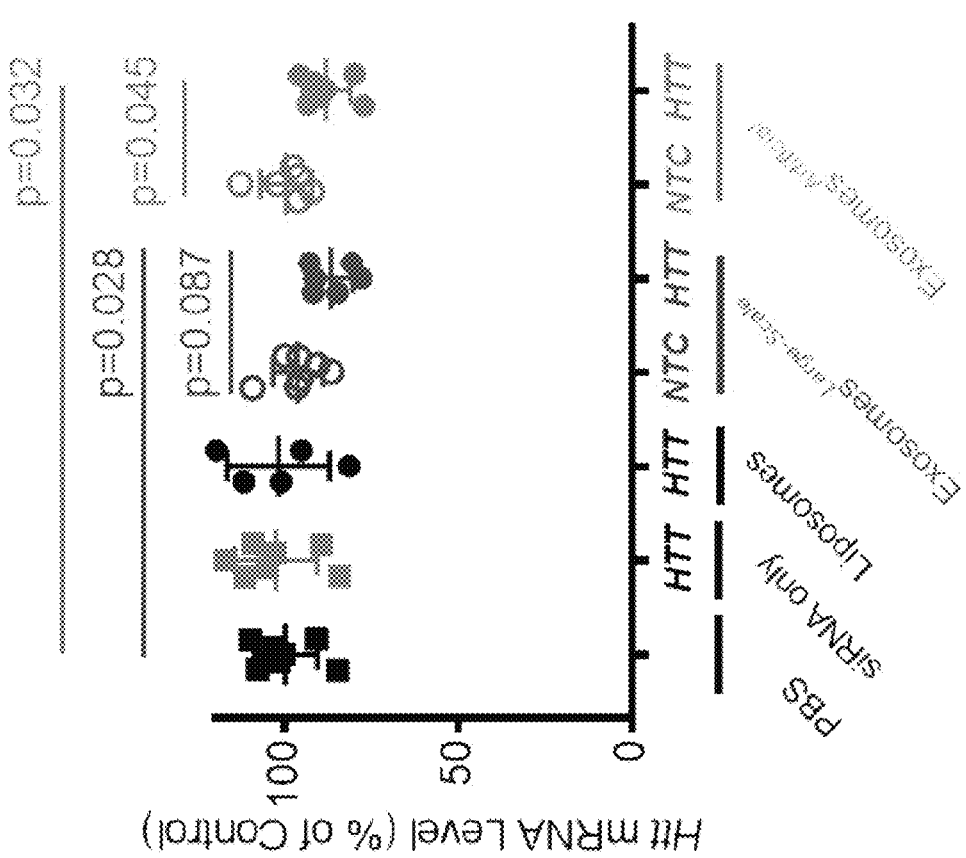

To evaluate if siRNA-containing artificial exosomes would support Huntingtin silencing in vivo, siRNA-containing natural exosomes and artificial exosomes infused into mouse brain were compared. For the in vivo study, natural exosomes were produced using a combination of three-dimensional xenofree mesenchymal stem cell culture and tangential flow filtration-based exosome isolation (Large-Scale Exosomes). This method enabled the collection of a sufficient number of exosomes necessary to power the in vivo studies. Natural exosomes (large-scale exosomes) showed an activity indistinguishable from that of stressed exosomes and artificial exosomes in vitro in primary neurons (FIG. 9A). When infused to the lateral ventricle of the mouse brain, both siRNA containing large-scale exosomes and artificial exosomes induced Huntingtin mRNA silencing (FIG. 9B and FIG. 9C), whereas control liposomes, non-targeting-control siRNA containing vesicles, and non-formulated siRNA were inactive (FIG. 9B and FIG. 9C).

Figure 9D:
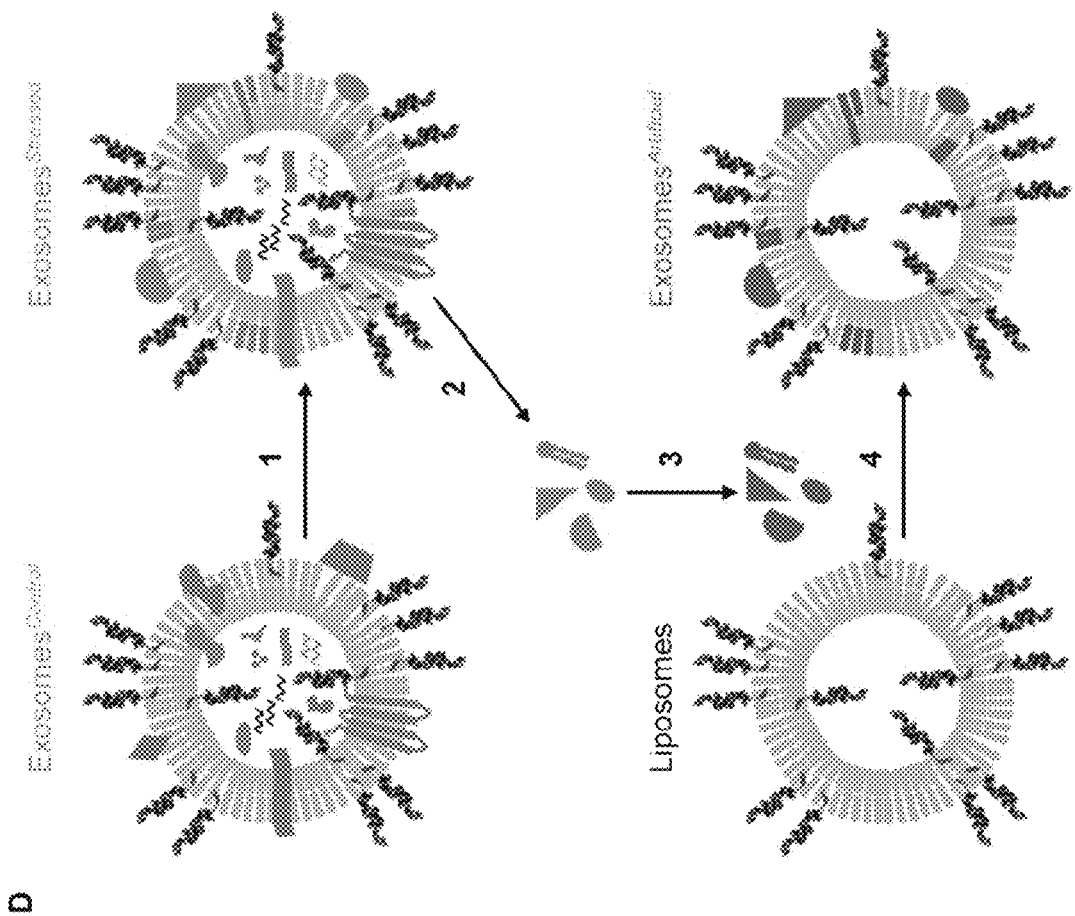

This disclosure introduces the concept of reverse engineering exosomes using mass spectrometry data of exosome composition with different activities (FIG. 9D). First, the introduction of a stress factor (i.e., serum deprivation) into exosome-producing cells improved exosome activity by altering protein and lipid composition. Second, proteins and lipids enriched in stressed exosomes were validated for contribution to enhanced vesicle trafficking to target cells. Finally, purified versions of the proteins and lipids identified in the second step were associated with neutral liposomes. This disclosure introduces a reverse engineering approach to building protein and lipid components into artificial exosomes, which then exhibit the essential biological activity of natural exosomes, similar to the construction of minimal artificial cells.

What is claimed:

1. An artificial exosome comprising:
   (a) one or more proteins comprising rab7, desmoplakin, alpha 2-HS glycoprotein (AHSG), or a mixture thereof, wherein each protein further comprises a lipid anchor; and
   (b) a cardiolipin or a variant thereof,
   wherein the artificial exosome is loaded with exogenously-derived, heterologous cargo selected from the group consisting of a peptide, a polypeptide, a nucleic acid, a virus, a small molecule, a fluorophore, and a combination thereof.

2. The artificial exosome of claim 1, wherein the artificial exosome further comprises dioleoylphosphatidylcholine (DOPC) and cholesterol.

3. The artificial exosome of claim 1, wherein:
   the lipid anchor comprises one or more of a myristoylation, a palmitoylation, a prenylation, and a glypiation; and/or
   the lipid anchor is a transmembrane domain, a $PIP_2$-binding domain, or a $PIP_3$-binding domain.

4. The artificial exosome of claim 1, wherein the cardiolipin or variant thereof is selected from the group consisting of cardiolipin, monolysocardiolipin, and dilysocardiolipin.

5. The artificial exosome of claim 1, wherein the cardiolipin or the variant thereof is dilysocardiolipin.

6. The artificial exosome of claim 1, wherein the cardiolipin or variant thereof comprises about 10% w/w to about 50% w/w of the total lipid content of the artificial exosome.

7. The artificial exosome of claim 1, wherein the cardiolipin or variant thereof comprises about 30% w/w of the total lipid content of the artificial exosome, optionally wherein the artificial exosome comprises a DOPC:cholesterol:cardiolipin ratio of about 40:30:30% w/w.

8. The artificial exosome of claim 1, wherein the exogenously-derived cargo molecule comprises an oligonucleotide.

9. The artificial exosome of claim 8, wherein the oligonucleotide comprises one or more hydrophobic modifications.

10. The artificial exosome of claim 8, wherein the oligonucleotide comprises one or more modified nucleotides comprising a modified ribose group, a modified phosphate group, a modified nucleobase, or a mixture thereof.

11. A method of isolating artificial exosomes comprising an exogenously-derived cargo from a sample comprising a population of exosomes, wherein the method comprises incubating the sample with a binding agent that binds to a protein comprising one or more of rab7, desmoplakin, and alpha 2-HS glycoprotein (AHSG), and a cardiolipin or a variant thereof; wherein each protein further comprises a lipid anchor; wherein the binding agent binds to the one or more proteins of the artificial exosome and thereby isolates the sample, and wherein the artificial exosome is loaded with exogenously-derived, heterologous cargo selected from the group consisting of a peptide, a polypeptide, a nucleic acid, a virus, a small molecule, a fluorophore, and a combination thereof.

12. The method of claim 11, wherein the binding agent is an antibody or an antigen-binding fragment thereof.

13. A method of producing an artificial exosome comprising an exogenously-derived cargo comprising proteins comprising rab7, desmoplakin, and alpha 2-HS glycoprotein (AHSG), and a cardiolipin or variants thereof comprising the steps of:
   a) mixing DOPC, cholesterol, and a cardiolipin or a variant thereof to form a cardiolipin-containing liposome; and
   b) incubating the cardiolipin-containing liposome with rab7, desmoplakin, and AHSG to form an artificial exosome.

14. The method of claim 13, further comprising c) centrifuging the artificial exosome to isolate the artificial exosome.

15. The method of claim 14, wherein the mixing step a) further comprises mixing a cargo molecule to produce a loaded cardiolipin-containing liposome.

16. The method of claim 14, further comprising step d) wherein the isolated artificial exosome is incubated with a cargo molecule to produce a loaded artificial exosome.

17. The method of claim 13, further comprising drying the mixture of step a) to form a dry lipid film and rehydrating the dry lipid film in an aqueous buffer to form the cardiolipin-containing liposome.

18. The method of claim 13, wherein mixing step a) occurs in an organic solvent.

19. The method of claim 13, wherein the incubation step b) occurs for about 1 hour and at about 37° C.

20. A method of delivering a cargo molecule to a neuronal cell, comprising contacting the neuronal cell with an artificial exosome containing the cargo molecule, wherein the artificial exosome comprises one or more proteins comprising rab7, desmoplakin, AHSG, and a cardiolipin or variant thereof; wherein each protein further comprises a lipid anchor; and wherein the cargo molecule is delivered to the neuronal cell.

* * * * *